US010696735B2

(12) United States Patent
Yonan et al.

(10) Patent No.: US 10,696,735 B2
(45) Date of Patent: Jun. 30, 2020

(54) MODULATION OF CHARGE VARIANTS IN A MONOCLONAL ANTIBODY COMPOSITION

(71) Applicant: Outlook Therapeutics, Inc., Cranbury, NJ (US)

(72) Inventors: Chris Yonan, Cranbury, NJ (US); Christine Caroselli, Cranbury, NJ (US); Wiphusanee Dendamrongvit, Cranbury, NJ (US); Scott Gangloff, Cranbury, NJ (US)

(73) Assignee: Outlook Therapeutics, Inc., Cranbury, NJ (US)

( * ) Notice: Subject to any disclaimer, the term of this patent is extended or adjusted under 35 U.S.C. 154(b) by 237 days.

(21) Appl. No.: 15/545,271

(22) PCT Filed: Jan. 21, 2016

(86) PCT No.: PCT/US2016/014252
§ 371 (c)(1),
(2) Date: Jul. 20, 2017

(87) PCT Pub. No.: WO2016/118707
PCT Pub. Date: Jul. 28, 2016

(65) Prior Publication Data
US 2018/0009876 A1 Jan. 11, 2018

Related U.S. Application Data

(60) Provisional application No. 62/105,890, filed on Jan. 21, 2015.

(51) Int. Cl.
| | | |
|---|---|---|
| *C07K 16/24* | (2006.01) | |
| *C07K 1/18* | (2006.01) | |
| *C07K 1/16* | (2006.01) | |
| *C07K 16/00* | (2006.01) | |
| *C07K 1/22* | (2006.01) | |
| *B01D 15/36* | (2006.01) | |
| *B01D 15/38* | (2006.01) | |
| *B01D 15/32* | (2006.01) | |
| *C07K 1/34* | (2006.01) | |

(52) U.S. Cl.
CPC ............ *C07K 16/00* (2013.01); *B01D 15/327* (2013.01); *B01D 15/362* (2013.01); *B01D 15/363* (2013.01); *B01D 15/3809* (2013.01); *B01D 15/3847* (2013.01); *C07K 1/165* (2013.01); *C07K 1/18* (2013.01); *C07K 1/22* (2013.01); *C07K 1/34* (2013.01); *C07K 16/241* (2013.01); *C07K 2317/21* (2013.01); *C07K 2317/40* (2013.01); *C07K 2317/51* (2013.01); *C07K 2317/515* (2013.01); *C07K 2317/76* (2013.01)

(58) Field of Classification Search
None
See application file for complete search history.

(56) References Cited

U.S. PATENT DOCUMENTS

| | | |
|---|---|---|
| 6,090,382 A | 7/2000 | Salfeld et al. |
| 6,258,562 B1 | 6/2001 | Salfeld et al. |
| 7,223,394 B2 | 5/2007 | Salfeld et al. |
| 7,541,031 B2 | 6/2009 | Salfeld et al. |
| 7,863,426 B2 | 1/2011 | Wan et al. |
| 7,919,264 B2 | 4/2011 | Maksymowych et al. |
| 7,935,808 B2 | 5/2011 | Gion et al. |
| 8,034,906 B2 | 10/2011 | Borhani et al. |
| 8,067,547 B2 | 11/2011 | Ewert et al. |
| 8,092,998 B2 | 1/2012 | Stuhlmüller et al. |
| 8,093,045 B2 | 1/2012 | Pla et al. |
| 8,187,836 B2 | 5/2012 | Hsieh et al. |
| 8,206,714 B2 | 6/2012 | Salfeld et al. |
| 8,216,583 B2 | 7/2012 | Kruase et al. |
| 8,231,876 B2 | 7/2012 | Wan et al. |
| 8,258,268 B2 | 9/2012 | Wu et al. |
| 8,372,400 B2 | 2/2013 | Salfeld et al. |
| 8,410,259 B2 | 4/2013 | Gion et al. |
| 8,414,894 B2 | 4/2013 | Salfeld et al. |
| 8,420,081 B2 | 4/2013 | Fraunhofer et al. |
| 8,455,219 B2 | 6/2013 | Hsieh et al. |

(Continued)

FOREIGN PATENT DOCUMENTS

| | | |
|---|---|---|
| CN | 102078608 A | 6/2011 |
| CN | 105779394 A | 7/2016 |

(Continued)

OTHER PUBLICATIONS

GE Healthcare "Ion Exchange Chromatography and chromatofocusing, Principles and Methods" pp. 1-170, copyright 2004-2016 (Year: 2004).*
Van Reis "Bioprocess membrane technology" J Membrane Science 297 (2007) 16-50 (Year: 2007).*
Allen, J.G. et al. (2016) "Facile Modulation of Antibody Fucosylation with Small Molecule Fucostatin Inhibitors and Cocrystal Structure with GDP-Mannose 4,6-Dehydratase" ACS Chem Biol, 11:2734-2743.
Bandyopadhyay, S. et al. (2015) "Physicochemical and functional characterization of a biosimilar adalimumab ZRC-3197" Biosimilars, 5:1-18.
Beck, A. et al. (Apr. 2012) "Biosimilar, Biobetter, and Next Generation Antibody Characterization by Mass Spectrometry" Anal Chem, 84(11):4637-4646.

(Continued)

*Primary Examiner* — Daniel E Kolker
*Assistant Examiner* — James L Rogers
(74) *Attorney, Agent, or Firm* — Cooley LLP; Ivor R. Elrifi; Matthew Pavao

(57) ABSTRACT

Combinations of different chromatography modalities with particularly refined conditions significantly reduce acid charge variants in a preparation of monoclonal antibodies. The process for reducing acid charge variants utilizes a combination of anion exchange and hydrophobic interaction chromatography, followed by cation exchange chromatography polishing, whereby the levels of acidic or basic charge species of the monoclonal antibodies may be modulated to a desired level.

30 Claims, 22 Drawing Sheets

Specification includes a Sequence Listing.

(56) References Cited

U.S. PATENT DOCUMENTS

| | | | |
|---|---|---|---|
| 8,652,474 B2 * | 2/2014 | Harris | C07K 16/065 424/143.1 |
| 8,663,945 B2 | 3/2014 | Pla et al. | |
| 8,679,061 B2 | 3/2014 | Julian et al. | |
| 8,715,664 B2 | 5/2014 | Hoffman et al. | |
| 8,747,854 B2 | 6/2014 | Okun et al. | |
| 8,753,633 B2 | 6/2014 | Salfeld et al. | |
| 8,753,839 B2 | 6/2014 | Fraunhofer et al. | |
| 8,795,670 B2 | 8/2014 | Krause et al. | |
| 8,802,100 B2 | 8/2014 | Krause et al. | |
| 8,802,101 B2 | 8/2014 | Krause et al. | |
| 8,802,102 B2 | 8/2014 | Krause et al. | |
| 8,808,700 B1 | 8/2014 | Hoffman et al. | |
| 8,821,865 B2 | 9/2014 | Neu et al. | |
| 8,846,046 B2 | 9/2014 | Kaymakcalan et al. | |
| 8,883,146 B2 | 11/2014 | Fraunhofer et al. | |
| 8,883,156 B2 | 11/2014 | Wan et al. | |
| 8,889,135 B2 | 11/2014 | Fischkoff et al. | |
| 8,889,136 B2 | 11/2014 | Hoffman et al. | |
| 8,895,009 B2 | 11/2014 | Wan et al. | |
| 8,895,709 B2 | 11/2014 | Hickman et al. | |
| 8,906,372 B2 | 12/2014 | Wan et al. | |
| 8,906,373 B2 | 12/2014 | Banerjee et al. | |
| 8,906,646 B2 | 12/2014 | Pla et al. | |
| 8,911,737 B2 | 12/2014 | Fischkoff et al. | |
| 8,911,741 B2 | 12/2014 | Krause et al. | |
| 8,911,964 B2 | 12/2014 | Pla et al. | |
| 8,916,153 B2 | 12/2014 | Wan et al. | |
| 8,916,157 B2 | 12/2014 | Krause et al. | |
| 8,916,158 B2 | 12/2014 | Krause et al. | |
| 8,932,591 B2 | 1/2015 | Krause et al. | |
| 8,940,305 B2 | 1/2015 | Krause et al. | |
| 8,961,973 B2 | 2/2015 | Hoffman et al. | |
| 8,961,974 B2 | 2/2015 | Hoffman et al. | |
| 8,974,790 B2 | 3/2015 | Fischkoff et al. | |
| 8,986,693 B1 | 3/2015 | Hoffman et al. | |
| 8,992,926 B2 | 3/2015 | Fischkoff et al. | |
| 8,999,337 B2 | 4/2015 | Medich et al. | |
| 9,017,680 B2 | 4/2015 | Fischkoff et al. | |
| 9,018,361 B2 | 4/2015 | Hickman et al. | |
| 9,061,005 B2 | 6/2015 | Hoffman et al. | |
| 9,062,106 B2 | 6/2015 | Bengea et al. | |
| 9,067,990 B2 | 6/2015 | Wang et al. | |
| 9,067,992 B2 | 6/2015 | Hoffman et al. | |
| 9,072,668 B2 | 7/2015 | Dai et al. | |
| 9,073,987 B2 | 7/2015 | Fischkoff et al. | |
| 9,073,988 B2 | 7/2015 | Pla et al. | |
| 9,085,618 B2 | 7/2015 | Ramasubramanyan et al. | |
| 9,085,619 B2 | 7/2015 | Fraunhofer et al. | |
| 9,085,620 B1 | 7/2015 | Hoffman et al. | |
| 9,086,418 B2 | 7/2015 | Maksymowych et al. | |
| 9,090,688 B2 | 7/2015 | Bengea et al. | |
| 9,090,689 B1 | 7/2015 | Hoffman et al. | |
| 9,090,867 B2 | 7/2015 | Pla et al. | |
| 9,096,666 B2 | 8/2015 | Wan et al. | |
| 9,102,723 B2 | 8/2015 | Wan et al. | |
| 9,109,010 B2 | 8/2015 | Hickman et al. | |
| 9,114,166 B2 | 8/2015 | Krause et al. | |
| 9,150,645 B2 | 10/2015 | Subramanian et al. | |
| 9,180,205 B2 | 11/2015 | Zeng et al. | |
| 9,181,572 B2 | 11/2015 | Subramanian et al. | |
| 9,187,559 B2 | 11/2015 | Hoffman et al. | |
| 9,193,787 B2 | 11/2015 | Chumsae | |
| 9,200,070 B2 | 12/2015 | Ramasubramanyan et al. | |
| 9,220,781 B2 | 12/2015 | Krause et al. | |
| 9,234,032 B2 | 1/2016 | Pla et al. | |
| 9,272,041 B2 | 3/2016 | Krause et al. | |
| 9,272,042 B2 | 3/2016 | Krause et al. | |
| 9,273,132 B2 | 3/2016 | Wan et al. | |
| 9,284,370 B1 | 3/2016 | Medich et al. | |
| 9,289,497 B2 | 3/2016 | Krause et al. | |
| 9,295,725 B2 | 3/2016 | Krause et al. | |
| 9,302,011 B2 | 4/2016 | Krause et al. | |
| 9,320,797 B2 | 4/2016 | Sloey et al. | |
| 9,327,032 B2 | 5/2016 | Krause et al. | |
| 9,328,165 B2 | 5/2016 | Wan et al. | |
| 9,334,319 B2 | 5/2016 | Ramasubramanyan et al. | |
| 9,334,320 B2 | 5/2016 | Okun et al. | |
| 9,340,611 B2 | 5/2016 | Manning et al. | |
| 9,340,612 B2 | 5/2016 | Manning et al. | |
| 9,346,880 B2 | 5/2016 | Manning et al. | |
| 9,359,434 B2 | 6/2016 | Subramanian et al. | |
| 9,365,645 B1 | 6/2016 | Bengea et al. | |
| 9,382,317 B2 | 7/2016 | Manning et al. | |
| 9,393,304 B2 | 7/2016 | Fernandez et al. | |
| 9,452,138 B2 | 9/2016 | Trollsas et al. | |
| 9,669,093 B2 | 6/2017 | Medich et al. | |
| 10,376,582 B2 | 8/2019 | Cini et al. | |
| 2008/0118496 A1 | 5/2008 | Medich et al. | |
| 2008/0166348 A1 | 7/2008 | Kupper et al. | |
| 2009/0028794 A1 | 1/2009 | Medich et al. | |
| 2009/0123378 A1 | 5/2009 | Wong et al. | |
| 2009/0226530 A1 | 9/2009 | Lassner et al. | |
| 2010/0021451 A1 | 1/2010 | Wong | |
| 2010/0111853 A1 | 5/2010 | Hickman et al. | |
| 2010/0278822 A1 | 11/2010 | Fraunhofer et al. | |
| 2011/0059079 A1 | 3/2011 | Babuka et al. | |
| 2011/0076273 A1 | 3/2011 | Adler et al. | |
| 2011/0171227 A1 | 7/2011 | Okun et al. | |
| 2011/0312000 A1 | 12/2011 | Kobayashi et al. | |
| 2012/0122076 A1 | 5/2012 | Lau et al. | |
| 2013/0079272 A1 | 3/2013 | Hui et al. | |
| 2013/0115224 A1 | 5/2013 | Salfeld et al. | |
| 2013/0122018 A1 | 5/2013 | Salfeld et al. | |
| 2013/0243764 A1 | 9/2013 | Ellis et al. | |
| 2013/0330356 A1 | 12/2013 | Salfeld et al. | |
| 2013/0338344 A1 | 12/2013 | Ramasubramanyan et al. | |
| 2014/0141007 A1 | 5/2014 | Fraunhofer et al. | |
| 2014/0141008 A1 | 5/2014 | Fraunhofer et al. | |
| 2014/0170152 A1 | 6/2014 | Hsieh et al. | |
| 2014/0186368 A1 | 7/2014 | Fischkoff et al. | |
| 2014/0186446 A1 | 7/2014 | Trollsas et al. | |
| 2014/0200332 A1 | 7/2014 | Kaymakcalan et al. | |
| 2014/0248215 A1 | 9/2014 | Hoffman et al. | |
| 2014/0271633 A1 | 9/2014 | Hossler | |
| 2014/0275486 A1 | 9/2014 | Chumsae | |
| 2014/0288278 A1 | 9/2014 | Nti-Gyabaah et al. | |
| 2014/0314745 A1 | 10/2014 | Rives et al. | |
| 2014/0329279 A1 | 11/2014 | Wang et al. | |
| 2014/0377275 A1 | 12/2014 | Neu et al. | |
| 2015/0065696 A1 | 3/2015 | Wang et al. | |
| 2015/0110799 A1 * | 4/2015 | Ramasubramanyan | C07K 16/241 424/142.1 |
| 2015/0210735 A1 | 7/2015 | Hickman et al. | |
| 2015/0246968 A1 | 9/2015 | Fischkoff et al. | |
| 2015/0344564 A1 | 12/2015 | Hickman et al. | |
| 2015/0361170 A1 | 12/2015 | Fraunhofer et al. | |
| 2016/0017030 A1 | 1/2016 | Neu et al. | |
| 2016/0046708 A1 | 2/2016 | Subramanian et al. | |
| 2016/0083452 A1 | 3/2016 | Hickman et al. | |
| 2016/0089495 A1 | 3/2016 | Julian et al. | |
| 2016/0185849 A1 | 6/2016 | Hoffman et al. | |
| 2016/0186130 A1 | 6/2016 | Pla et al. | |
| 2016/0207992 A1 | 7/2016 | Bengea et al. | |
| 2016/0235845 A1 | 8/2016 | Cini et al. | |
| 2018/0009876 A1 | 1/2018 | Yonan et al. | |
| 2019/0030163 A1 | 1/2019 | Gutka et al. | |
| 2019/0048070 A1 | 2/2019 | Santoro et al. | |
| 2019/0161543 A1 | 5/2019 | Santoro et al. | |

FOREIGN PATENT DOCUMENTS

| | | |
|---|---|---|
| EP | 0929578 B1 | 5/2003 |
| EP | 2081025 A1 | 7/2009 |
| EP | 2295071 A1 | 3/2011 |
| EP | 2324851 A1 | 5/2011 |
| EP | 2332565 A1 | 6/2011 |
| EP | 2335731 A2 | 6/2011 |
| EP | 2335732 A2 | 6/2011 |
| EP | 2338516 A2 | 6/2011 |
| EP | 1578439 B1 | 7/2011 |
| EP | 2359855 A2 | 8/2011 |
| EP | 2359856 A1 | 8/2011 |

(56) References Cited

FOREIGN PATENT DOCUMENTS

| | | |
|---|---|---|
| EP | 2361637 A1 | 8/2011 |
| EP | 2363144 A1 | 9/2011 |
| EP | 2363145 A1 | 9/2011 |
| EP | 2364731 A1 | 9/2011 |
| EP | 2371859 A2 | 10/2011 |
| EP | 1528933 B1 | 5/2012 |
| EP | 2500037 A2 | 9/2012 |
| EP | 2500413 A1 | 9/2012 |
| EP | 2500414 A1 | 9/2012 |
| EP | 2500415 A1 | 9/2012 |
| EP | 2500416 A1 | 9/2012 |
| EP | 2527425 A1 | 11/2012 |
| EP | 2532737 A1 | 12/2012 |
| EP | 1406656 B1 | 1/2013 |
| EP | 2660328 A1 | 11/2013 |
| EP | 2666472 A2 | 11/2013 |
| EP | 2666478 A2 | 11/2013 |
| EP | 2666479 A2 | 11/2013 |
| EP | 2666480 A2 | 11/2013 |
| EP | 2703010 A2 | 3/2014 |
| EP | 2708242 A2 | 3/2014 |
| EP | 2738178 A1 | 6/2014 |
| EP | 2738179 A1 | 6/2014 |
| EP | 1924287 B1 | 1/2015 |
| EP | 2946765 A1 | 11/2015 |
| EP | 2990485 A1 | 3/2016 |
| EP | 2397494 B1 | 8/2016 |
| EP | 2637690 B1 | 9/2016 |
| EP | 1737491 B1 | 11/2016 |
| EP | 2357200 B1 | 11/2016 |
| EP | 2359856 B1 | 5/2017 |
| WO | WO-92/13876 A1 | 8/1992 |
| WO | WO-9957134 A1 * 11/1999 ............... C07K 1/18 | |
| WO | WO-2006/096461 A2 | 9/2006 |
| WO | WO-2006/125229 A2 | 11/2006 |
| WO | WO-2007/050498 A2 | 5/2007 |
| WO | WO-2008/033517 A2 | 3/2008 |
| WO | WO-2008/154543 A2 | 12/2008 |
| WO | WO-2009/073569 A2 | 6/2009 |
| WO | WO-2009/073805 A2 | 6/2009 |
| WO | WO-2009/118662 A2 | 10/2009 |
| WO | WO-2010/062896 A1 | 6/2010 |
| WO | WO-2010/129469 A1 | 11/2010 |
| WO | WO-2010/141855 A1 | 12/2010 |
| WO | WO-2011/104381 A2 | 9/2011 |
| WO | WO-2012/041768 A1 | 4/2012 |
| WO | WO-2012/051147 A1 | 4/2012 |
| WO | WO-2013/011076 A | 1/2013 |
| WO | WO-2013/114164 A1 | 8/2013 |
| WO | WO-2013/114165 A1 | 8/2013 |
| WO | WO-2013/158279 A1 | 10/2013 |
| WO | WO-2013/186230 A1 | 12/2013 |
| WO | WO-2014/039903 A2 | 3/2014 |
| WO | WO-2014/055370 A1 | 4/2014 |
| WO | WO-2014/099636 A1 | 6/2014 |
| WO | WO 2014-143185 A1 | 9/2014 |
| WO | WO-2014/158231 A1 | 10/2014 |
| WO | WO 2014-207763 A1 | 12/2014 |
| WO | WO-2015/051310 A2 | 4/2015 |
| WO | WO-2015/057910 A1 | 4/2015 |
| WO | WO-2015/140700 A1 | 9/2015 |
| WO | WO-2016/066688 A1 | 5/2016 |
| WO | WO-2016/118707 A1 | 7/2016 |
| WO | WO-2016/120413 A1 | 8/2016 |
| WO | WO-2017/120347 A1 | 7/2017 |
| WO | WO-2017/120359 A1 | 7/2017 |
| WO | WO-2017/136433 A1 | 8/2017 |
| WO | WO-2017/136753 A1 | 8/2017 |

OTHER PUBLICATIONS

Beck, A. et al. (2015) "Cutting-edge mass spectrometry characterization of originator, biosimilar and biobetter antibodies" J Mass Spectrom, 50:285-297.

Butler, M. et al. (2012) "Recent advances in technology supporting biopharmaceutical production from mammalian cells" Appl Microbiol Biotechnol, 96:885-894.

Cleland, J.L. et al. (Mar. 2001) "A specific molar ratio of stabilizer to protein is required for storage stability of a lyophilized monoclonal antibody" J Pharma Sci, 90(3):310-321.

Cole, L. (Apr. 2012) "Screening optimal buffer conditions for a therapeutic antibody using Chirascan™-plus Automated Circular Dichroism" Appl Photophysics, p. 1-8 [online]. Retrieved from the Internet: http://www.photophysics.com/sites/default/files/documents/application_notes/4210Q244_AppNote_ACD.pdf. Retrieved on Jun. 30, 2015.

Costa, A.R. et al. (2013) "The impact of microcarrier culture optimization on the glycosylation profile of a monoclonal antibody" SpringerPlus, 2:25, 10 pages.

Du, Y. et al. (2012) "Chromatographic analysis of the acidic and basic species of recombinant monoclonal antibodies" mAbs, 4(5):578-585.

Fransson, J. et al. (Nov. 1996) "Local Tolerance of Subcutaneous Injections" J Pharm Pharmacol, 48:1012-1015.

Hossler, P. et al. (2015) "Cell Culture Media Supplementation of Bioflavonoids for the Targeted Reduction of Acidic Species Charge Variants on Recombinant Therapeutic Proteins" Biotechnol Prog, 31:1039-1052.

Imai-Nishiya, H. et al. (2007) "Double knockdown of α1,6-fucosyltransferase (FUT8) and GDP-mannose 4,6-dehydratase (GMD) in antibody-producing cells: a new strategy for generating fully non-fucosylated therapeutic antibodies with enhanced ADCC" *BMC Biotechnology*, 7:84, 13 pages.

Kaiser, C. et al. (Sep. 2011) "Injection-site reactions upon Kineret (anakinra) administration: experiences and explanations" Rheumatol International: Clinical and Experimental Investigations, 32(2):295-299.

Kanda, Y. et al. (2007) "Establishment of a GDP-mannose 4,6-dehydratase (GMD) knockout host cell line: a new strategy for generating completely non-fucosylated recombinant therapeutics" J Biotechnol, 130:300-310.

Kawasaki, Nana and Akiko Ishii (Sep. 2012) "Kotai-iyakuhin no Baio-Kouzokuhin no Syorai Tenbou (Japanese) (Future outlook for biosimilars of antibody preparations)" Rinsho to Biseibutsu (Clinical and Microorganisms), vol. 39, No. 5, p. 459-465, with English machine translation, 10 pages.

Lapadula, G. et al. (Jan. 2014) "Adalimumab in the Treatment of Immune-Mediated Diseases" Intl J Immunopathol Pharmacol, 27(1):33-48.

Matsuda, Rieko (1996) "Acids and Bases-Bronsted Setsu wo chushin ni (Japanese) (Focusing on the Bases-Bronsted theory)" Kagaku to Kyouiku (Chemistry & Education). The Chemical Society of Japan, vol. 44, No. 1, p. 44-47, with machine translation, 6 pages.

Mori, K. et al. (2007) "Non-fucosylated therapeutic antibodies: the next generation of therapeutic antifodies" Cytotechnology, 55:109-114.

Rillahan, C.D. et al. (2012) "Global metabolic inhibitors of sialyl- and fucosyltransferases remodel the glycome" Nat Chem Biol, 8:661-668.

Rouiller, Y. et al. (2014) "Modulation of mAb Quality Attributes Using Microliter Scale Fed-Batch Cultures" Biotechnol Prog, 30:571-583.

Satoh, M. et al. (2006) "Non-fucosylated therapeutic antibodies as next-generation therapeutic antibodies" Expert Opin Biol Ther, 6(11):1161-1173.

Serrato, J.A. et al. (2007) "Differences in the glycosylation profile of a monoclonal antibody produced by hybridomas cultured in serum-supplemented, serum-free or chemically defined media" Biotechnol Appl Biochem, 47:113-124.

Schmelzer, A.E. and W.M. Miller (2002) "Hyperosmotic Stress and Elevated pCO2 Alter Monoclonal Antibody Charge Distribution and Monosaccharide Content" Biotechnol Prog, 18:346-353.

Tummala, S. et al. (2013) "Evaluation of Exogenous siRNA Addition as a Metabolic Engineering Tool for Modifying Biopharmaceuticals" Biotechnol Prog, 29(2):415-424. NIH Public Access Author Manuscript; available in PMC Nov. 10, 2014, 19 pages.

(56) References Cited

OTHER PUBLICATIONS

Von Horsten, H.H. et al. (2010) "Production of non-fucosylated antibodies by co-expression of heterologous GDP-6-deoxy-D-lyxo-4-hexulose reductase" Glycobiology, 20(12):1607-1618.

Wang, W. (Aug. 1999) "Instability, stabilization, and formulation of liquid protein pharmaceuticals" Intl J Pharma, 185(2):129-188.

Wang, W. et al. (2007) "Antibody Structure, Instability and Formulation" J Pharma Sci, 96(1):1-26.

Xie, P. et al. (2016) "Elucidating the effects of pH shift on IgG1 monoglonal antibody acidic charge variant levels in Chinese hamster ovary cell cultures" Appl Microbiol Biotechnol, 100:10343-10353.

Yamane-Ohnuki, N. and M. Satoh (2009) "Production of therapeutic antibodies with controlled fucosylation" mAbs, 1(3):230-236.

Zhang, X. et al. (2015) "Culture temperature modulates monoclonal antibody charge variation distribution in Chinese hamster ovary cell cultures" Biotechnol Lett, 37:2151-2157.

Zhou, Q. et al. (Feb. 15, 2008) "Development of a simple and rapid method for producing non-fucosylated oligomannose containing antibodies with increased effector function" Biotechnol Bioeng, 99(3):652-665.

\* cited by examiner

MODULATION OF CHARGE VARIANTS IN A MONOCLONAL ANTIBODY COMPOSITION

CROSS REFERENCE TO RELATED APPLICATIONS

This application is a National Stage Application, filed under 35 U.S.C. §371, of International Application No. PCT/US2016/014252, filed Jan. 21, 2016, which claims the benefit of priority to U.S. Provisional Application No. 62/105,890, filed on Jan. 21, 2015, the contents of each of which are incorporated by reference herein, in their entirety and for all purposes.

REFERENCE TO A SEQUENCE LISTING

This application includes a Sequence Listing submitted electronically as a text file named Adalimumab_ST25.txt, created on Jan. 19, 2016, with a size of 12,000 bytes. The Sequence Listing is incorporated by reference herein.

FIELD OF THE INVENTION

The invention relates generally to the field of protein biochemistry. More particularly, the invention relates to a purification scheme for monoclonal antibodies and other small binding peptides and proteins, which substantially reduces charge variants, thereby producing a more homogenous population of the antibody for patient administration.

BACKGROUND OF THE INVENTION

Various publications, including patents, published applications, accession numbers, technical articles and scholarly articles are cited throughout the specification. Each of these cited publications is incorporated by reference herein, in its entirety and for all purposes.

As part of the Biologics Price Competition and Innovation Act (BPCIA), a biological drug product (produced in or derived from living organisms) may be demonstrated to be "biosimilar" if data show that, among other things, the product is "highly similar" to an already-approved biological product. The biosimilar product should retain at least the biologic function and treatment efficacy of the U.S. Food and Drug Agency-approved biological product.

Monoclonal antibodies (mAbs) may be used as therapeutic proteins. Purified monoclonal antibodies are most often present in a complex heterogeneous mixture based on chemical modifications of selected amino acids sites that range from subtle to significant. Understanding the impact of these modifications is of considerable importance in the biotechnology field. Monoclonal antibodies have charge heterogeneity that optimizes the balance of gaining favorable electrostatic interactions and determines their structure, stability, binding affinity, chemical properties and, hence, their biological activity.

Consistency of a biologic drug product, along with a maximized shelf life of the product are of paramount importance to drug developers and manufacturers. Short shelf life usually translates to manufacturing challenges and high costs of production by manufacturers.

During the cell culture or fermentation process, antibodies and proteins may undergo phenomena known as post-translational modifications. These modifications contribute to several forms of heterogeneity seen in therapeutic proteins. Additionally, there are forms of heterogeneity that occur during the manufacture caused by stresses imparted during the process such as size and charge that can occur due to enzymatic processes or spontaneous degradation and modifications. Monoclonal antibodies undergo chemical modification via several different mechanisms, including oxidation, deamidation, glycation, isomerization and fragmentation, that result in the formation of various charge variants and heterogeneity.

Chemical and enzymatic modifications such as deamidation, and sialylation, result in an increase in the net negative charge on mAbs and cause a decrease in pI values, thereby leading to formation of acidic variants. C-terminal lysine cleavage results in the loss of net positive charge leading to the formation of monoclonal antibody species with greater acidic charge. Another mechanism for generating acidic variants is the formation of various types of covalent adducts, e.g., glycation, where glucose or lactose can react with the primary amine of a lysine or arginine residue during manufacturing in glucose-rich culture media or during storage if a reducing sugar is present in the formulation. Formation of the basic variants can result from the presence of one or more C-terminal lysines or proline amidation, succinimide formation, amino acid oxidation or removal of sialic acid, which introduce additional positive charges or removal of negative charges; both types of modifications cause an increase in pI values.

Although there is substantial knowledge and experience with the degradation pathways that are active during production and formulation, a current challenge is to understand how the heterogeneity described above may affect efficacy, potency, immunogenicity and clearance. Little is known about the effects of charge on the PK of subcutaneously (SC) administered mAbs. Passage through the interstitium to the vascular or lymphatic capillaries can present a barrier to efficient drug absorption after SC administration. Interstitial diffusion of mAbs is likely to be influenced by their charge and their electrostatic interactions with negatively charged constituents of the interstitial area underlying the dermis of the skin.

Recently, the growth and interest in the development of biosimilars has presented several unique challenges to the production of biotherapeutics such as mAbs. The development of innovative molecules allows latitude to define the product quality attributes (PQAs) and, ultimately, the critical quality attributes (CQAs) of a mAb during the natural course of the development process. This paradigm, in turn, permits the implementation of a potentially robust production platform capable of handling the mAbs that a pipeline of candidates may produce with minimal optimization.

The development of biosimilar molecules, by contrast, imposes the confines of a predefined (by the innovator) set of product quality attribute ranges. The impact on process development is that the latitude that a platform process may afford may be significantly reduced by the requirement to fit within a defined range for multiple PQAs. This is especially true for those attributes that are known to be or could potentially be biologically relevant such as the charge variants described above. Purification or reduction of such heterogeneity so as to achieve a more homogenous population poses a significant challenge to process developers. The differences in the species that make up the heterogeneous population of charge variants are often quite subtle and similar in their characteristics to the primary mAb population of interest. Consequently, these unwanted variants are difficult to separate effectively while maintaining a reasonable mAb recovery. There is a need to minimize these unwanted variants toward a more homogenous population of biosimilar mAbs.

SUMMARY OF THE INVENTION

The disclosure features processes for removing both acid charge variants and basic charge variants from a monoclonal antibody preparation. In some aspects, the process comprises a succession of Protein A chromatography, followed by a mixed mode hybrid of anion exchange and hydrophobic interaction chromatography (AEX/HIC), followed by cation exchange chromatography (CEX). Orthogonal virus inactivation steps may be included in the process. The monoclonal antibody pool prepared according to this process, which includes non-variant antibodies and acid charge variants of such antibodies, may be concentrated and formulated for storage and patient administration.

In some detailed aspects, the process comprises loading a mammalian cell-expressed monoclonal antibody onto a support comprising Protein A having an antibody binding capacity of from about 10 g/L to about 60 g/L, and eluting the monoclonal antibody from the Protein A, thereby producing a first eluate comprising the monoclonal antibody; optionally inactivating viruses in the first eluate, loading the first eluate onto an AEX/HIC support and allowing the first eluate to flow through the AEX/HIC support, thereby producing a flow-through pool comprising the monoclonal antibody, loading the flow-through pool comprising the monoclonal antibody onto a CEX support, monitoring the absorbance units and determining when the absorbance units, measured at UV A280, decrease about 7% to about 14% from the peak absorbance units, measured at UV A280, or about 7% to about 14% on a column volume basis, and then washing the CEX support with a wash buffer having a pH of from about 5.8 to about 6.6 and a conductivity target of from about 6.6 mS/cm to about 7.6 mS/cm for a period of time sufficient to remove a desired amount of acidic charge species of the antibody, and then eluting the monoclonal antibody from the CEX chromatography support in step with an elution buffer having a pH of from about 6.0 to about 6.4 and a conductivity target of from about 10 mS/cm to about 14 mS/cm, thereby producing a second eluate comprising the monoclonal antibody and from about 10% to about 20% by weight of acid charge variants of the monoclonal antibody. The percentage of acid charge variants may be determined according to any suitable technique known in the art. Non limiting examples of suitable techniques include imaged capillary isoelectric focusing, cation exchange chromatography, and high performance liquid chromatography.

To remove basic charge variants, the method may further comprise, before eluting the monoclonal antibody according, washing the CEX support with a buffer comprising a pH of from about 6.5 to about 7.0, and then eluting the monoclonal antibody from the CEX support. Following removal of basic charge variants, the second eluate comprises the monoclonal antibody, acid charge variants, and from about 15% to about 25% by weight of basic charge variants of the monoclonal antibody as determined by any suitable technique.

The process is preferably used in accordance with monoclonal antibodies that are expressed by mammalian expression host cells such as CHO or HEK293 cells. The antibodies preferably specifically bind to tumor necrosis factor alpha. The monoclonal antibodies may comprise a heavy chain comprising the amino acid sequence of SEQ ID NO: 1 and a light chain comprising the amino acid sequence of SEQ ID NO: 2. The monoclonal antibodies are preferably adalimumab.

In some aspects, the Protein A support preferably is equilibrated with a buffer comprising about 20 mM sodium phosphate and about 50 mM sodium chloride, and a pH of from about 7 to about 7.4. In some aspects, the Protein A support is equilibrated with a buffer comprising about 20 mM sodium phosphate and about 50 mM sodium chloride, and a pH of from about 7.2. Equilibration precedes loading the expressed-monoclonal antibody preparation onto the support. Following loading and adsorption of monoclonal antibodies to the Protein A substrate, the support may be washed. Thereafter, the monoclonal antibodies may be eluted from the Protein A support with an elution buffer comprising about 80 mM acetic acid or sodium acetate and having a pH of about 3.5, thereby producing the first eluate comprising the monoclonal antibody. Following elution, the support may be re-equilibrated using the original equilibration buffer.

When included, the virus inactivation step may comprise adding citric acid to the eluate from the Protein A support until the pH of the Protein A eluate is from about 3.4 to about 3.6, and then holding the eluate at a temperature of from about 18° C. to about 25° C. for from about 50 to about 70 minutes and, following the holding, increasing the pH of the eluate to from about 7.3 to about 7.7 and then filtering the eluate. In some aspects, virus inactivation may comprise adding citric acid to the Protein A eluate until the pH of the eluate is about 3.5, and then holding the eluate at a temperature of from about 18° C. to about 25° C. for from about 50 to about 70 minutes and, following the holding, increasing the pH of the eluate to from about 7.4 to about 7.6 and then filtering the eluate. Filtering may comprise depth filtration followed by 0.2 micron filtration.

Following virus inactivation, if such inactivation is included, the filtered Protein A eluate (including the monoclonal antibodies as purified to this point) may be loaded onto a mixed mode chromatography support, for example, an AEX/HIC support. A non-limiting example of a suitable AEX/HIC support comprises a N-Benzyl-N-methyl ethanol amine ligand, which may have a binding capacity of from about 50 g/L to about 150 g/L. The support may be equilibrated with a buffer comprising about 50 mM HEPES and about 66 mM sodium chloride and having a pH of from about 7.4 to about 7.6. The loaded eluate is allowed to flow through the support, including the a N-Benzyl-N-methyl ethanol amine ligand. Following material loading, the support may be washed and re-equilibrated using the original equilibration buffer.

Following chromatography through the AEX/HIC support, the flow-through pool comprising the monoclonal antibody may be loaded onto a CEX support. A non-limiting example of a CEX support comprises a sulfopropyl or sulfonate ligand, which may have an antibody binding capacity of from about 25 g/L to about 65 g/L. Following loading and adsorption of monoclonal antibodies to the substrate, the CEX support may be washed, first with a buffer such as the equilibration buffer, and then with a washed with a second wash buffer having a higher conductivity to elute acid charge variants from the substrate, and then washed with a buffer such as the equilibration buffer in order to quench acidic charge elution. The second wash may be carried out for a duration of time sufficient to remove a desired amount of acidic charge species of the antibody. For example, for a biosimilar antibody, the desired amount may be the amount to achieve a level of acidic charge species in the CEX eluate that approximates the amount of acidic charge species in the reference antibody. Thus, in cases where a higher amount of acidic charge species are present in the flow-through pool from the AEX/HIC chromatography step, the duration of the second wash may be longer and, conversely, in cases where a lower of amount of acidic charge species are present in the flow-through pool from the AEX/HIC chromatography step, the duration of the second wash may be shorter.

In some aspects, acidic charge variants may be eluted from the CEX support by washing the support with a buffer having pH of from about 5.9 to about 6.5, or a pH of from about 6 to about 6.4, or a pH of from about 6.1 to about 6.3, or a pH of about 6.2 and/or a conductivity target of from about 6.8 mS/cm to about 7.4 mS/cm, from about 6.9 mS/cm to about 7.3 mS/cm, from about 7 mS/cm to about 7.2 mS/cm, or about 7.2 mS/cm. Such washing proceeds when the absorbance units, measured at UV A280, decrease from about 7% to about 14%, from about 8% to about 12%, from about 9% to about 11%, or about 10% from the peak absorbance units measured at UV A280, with such washing proceeding for a duration of time sufficient to remove a desired amount of acidic charge species of the antibody.

Following the wash to remove acidic charge species of the monoclonal antibody from the CEX support, the monoclonal antibody may be eluted from the CEX support. The antibody may be eluted by contacting the CEX support with an elution buffer that comprises about 100 mM sodium chloride, a pH of from about 6 to about 6.4, from about 6.1 to about 6.3, or about 6.2, and a conductivity target of from about 11 mS/cm to about 14 mS/cm, from about 12 mS/cm to about 14 mS/cm, from about 12 mS/cm to about 13 mS/cm, from about 12.3 mS/cm to about 13.3 mS/cm, from about 12.6 mS/cm to about 13 mS/cm, or about 12.8 mS/cm. The 100 mM sodium chloride may be attained by adding sodium chloride to the elution buffer over a gradient (e.g., increasing the concentration over time). The sodium chloride may be added to the elution buffer via a linear gradient or via a step-wise gradient.

The eluate from the CEX support comprises purified monoclonal antibodies, and from about 9% to about 15% by weight of acid charge variants of the monoclonal antibody. In some aspects, the eluate comprises from about 10% to about 20% by weight of acid charge variants of the monoclonal antibody, as determined by any suitable technique. In some aspects, the eluate comprises from about 11% to about 19% by weight of acid charge variants of the monoclonal antibody, as determined by any suitable technique. In some aspects, the eluate comprises from about 12% to about 19% by weight of acid charge variants of the monoclonal antibody, as determined by any suitable technique. In some aspects, the eluate comprises from about 14% to about 18% by weight of acid charge variants of the monoclonal antibody, as determined by any suitable technique. In some aspects, the eluate comprises from about 15% to about 17% by weight of acid charge variants of the monoclonal antibody, as determined by any suitable technique.

Optionally, the eluate from the CEX support, which comprises the monoclonal antibodies may be filtered. Optionally, the eluate from the CEX support, which comprises the monoclonal antibodies may be concentrated and/or diafiltered.

Compositions comprising monoclonal antibodies and acidic and/or basic charge variants of the monoclonal antibodies prepared according to such methods are provided.

DETAILED DESCRIPTION OF THE INVENTION

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

As used herein, the terms "comprising," "having," and "including" encompass the more restrictive terms "consisting essentially of" and "consisting of."

The terms subject and patient are used interchangeably, and include any animal. Subjects include mammals, including companion and farm mammals, as well as rodents, including mice, rabbits, and rats, and other rodents. Non-human primates preferred subjects. Human beings are highly preferred subjects.

Figure 1:
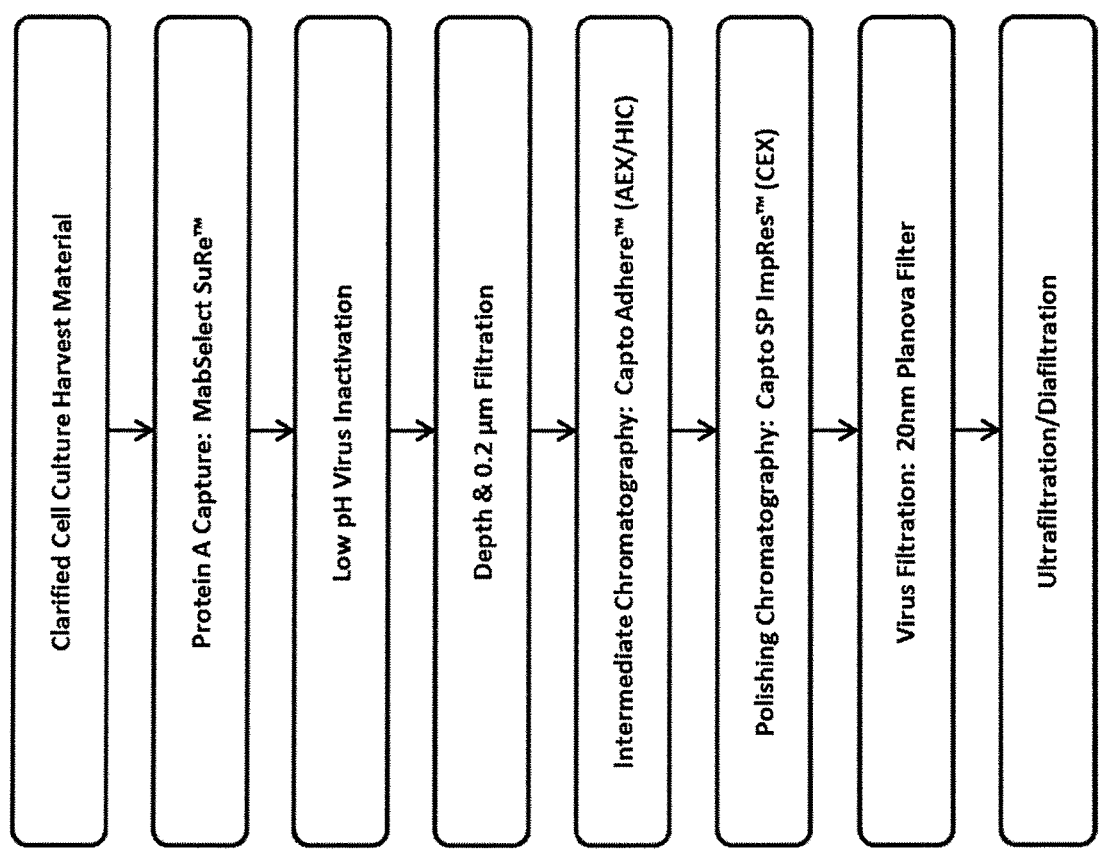
FIG. 1 shows an overview of the purification process.

It has been observed in accordance with the invention that substantial acidic charge variants could be removed from an isolated and purified population of mammalian cell-expressed monoclonal antibodies that bind to tumor necrosis factor (TNF)-alpha. The resulting population of monoclonal antibodies had enhanced homogeneity relative to the initial expression pool of antibodies, including less than about 15% by weight of acid charge variants. The purification process included an initial Protein A capture purification, followed by an intermediate chromatography step using a hybrid of anion exchange and hydrophobic interaction chromatography (AEX/HIC), followed by a polishing chromatography step using cation exchange chromatography (CEX). Notably, CEX is typically used as an intermediate chromatography step, with AEX/HIC typically used as a polishing chromatography step, such that the process inverted the customary antibody preparation protocol. The process also included two orthogonal steps for virus inactivation/removal, as well as concentration and diafiltration steps. An overview of the process is shown in FIG. 1. Accordingly, the invention features methods for removing charge variants, preferably acid charge species but also including basic species, from a monoclonal antibody composition. Compositions of monoclonal antibodies with reduced charge variants, as prepared using such methods, are also featured. The purification process may find use, for example, in the preparation of biosimilar monoclonal antibodies.

Purification processes according to the disclosure are suitable for any monoclonal antibody. In some preferred aspects, the antibody specifically binds to an epitope on TNF-alpha, and the epitope may be linear or conformational.

Preferably, the antibody is a full length monoclonal antibody, comprising both variable and constant regions. In some aspects, the antibody may comprise a derivative or fragment or portion of a full-length antibody that retains the antigen-binding specificity, and also preferably retains most or all of the affinity, of the full length antibody molecule. The antibody may comprise post-translational modifications (PTMs) or moieties, which may impact antibody activity or stability. The antibody may be methylated, acetylated, glycosylated, sulfated, phosphorylated, carboxylated, and/or amidated, and may comprise other moieties that are well known in the art.

In some preferred aspects, the antibody comprises a heavy chain comprising the amino acid sequence of SEQ ID NO: 1. In some preferred aspects, the antibody comprises a light chain comprising the amino acid sequence of SEQ ID NO: 2. Preferably, the antibody comprises a heavy chain constant domain and/or a light chain constant domain. The heavy and light chain amino acid sequences of the antibody may comprise those of U.S. Pat. No. 6,090,382.

In highly preferred aspects, the antibody comprises a heavy chain comprising the amino acid sequence of SEQ ID NO: 1 and a light chain comprising the amino acid sequence of SEQ ID NO: 2, an example of which is adalimumab. adalimumab comprises a molecular mass of about 148 kDa in glycosylated form, and about 145 kDa in de-glycosylated form, and comprises an isoelectric point of about 8.35, and an extinction coefficient (280 nm) of about $1.4$ $M^{-1}$ $cm^{-1}$. adalimumab comprises two kappa light chains di-sulfide-bonded to two gamma heavy chains, and comprises 1330 amino acids.

Common PTMs for adalimumab include N-glycosylation, C-terminal variants (e.g., cleavage of lysine, proline amidation), N-terminal pyro-E formation, oxidation, isomerization, deamidation, succinimide formation, mannosylation, and glycation. Moieties include any chemical group or combinations of groups commonly found on immunoglobulin molecules in nature, or otherwise added to antibodies by recombinant expression systems, including prokaryotic and eukaryotic expression systems.

The production of monoclonal antibodies and other proteins preferably is carried out in host cells such as mammalian or bacterial systems. The monoclonal antibody can be located in different locations within the cell or in some cases secreted from the cell into the media. In the latter case, the cells can be removed and separated from the monoclonal antibody by using centrifugation and/or filtration. The antibody is preferably expressed using mammalian cells. Non-limiting examples of suitable mammalian expression hosts include Chinese Hamster Ovary (CHO) cells and human embryonic kidney 293 (HEK293) cells.

The recombinantly expressed antibody may be clarified from its mammalian host cells by either a two stage depth filtration or centrifugation process. The depth filters may comprise cellulose fiber and diatomaceous earth. Following depth filtration, the material may be passed through a 0.2 μm filter to achieve the clarified cell culture supernatant. The clarified cell culture supernatant can then be purified using the process as described below.

Following expression, the preparation of monoclonal antibodies is purified in order to remove contaminants, including charge variants of the monoclonal antibodies themselves. As a first step, the antibody preparation may be loaded onto a support comprising Protein A, whereby the antibodies interact with the Protein A. The support preferably comprises particles that may be packed into a chromatography column. The Protein A preferably has an antibody binding capacity of from about 10 g/L to about 100 g/L, more preferably from about 10 g/L to about 60 g/L, and more preferably from about 20 g/L to about 50 g/L. MABSELECT SURE® Protein A media is an example of a suitable Protein A support. UNOsphere SUPrA™ media, PROSEP® Ultra Plus Protein A media, and ABSOLUTe® High Cap Protein A media are other examples of suitable Protein A supports. Any suitable Protein A support available in the art may be used.

Prior to loading the antibody preparation onto the Protein A support, the support is preferably equilibrated. The equilibration medium may comprise a buffer. The buffer may comprise from about 5 mM to about 50 mM of sodium phosphate and from about 20 mM to about 80 mM of sodium chloride. The buffer may comprise from about 10 mM to about 30 mM of sodium phosphate, from about 12 mM to about 28 mM of sodium phosphate, from about 15 mM to about 25 mM of sodium phosphate, from about 17 mM to about 23 mM of sodium phosphate, from about 15 mM to about 20 mM of sodium phosphate, from about 20 mM to about 25 mM of sodium phosphate, from about 15 mM to about 30 mM of sodium phosphate, from about 18 mM to about 22 mM of sodium phosphate, from about 19 mM to about 21 mM of sodium phosphate, or about 20 mM of sodium phosphate. The buffer may comprise from about 30 mM to about 70 mM of sodium chloride, from about 35 to about 65 mM of sodium chloride, from about 40 mM to about 60 mM of sodium chloride, from about 42 mM to about 58 mM of sodium chloride, from about 45 to about 55 mM of sodium chloride, from about 40 mM to about 50 mM of sodium chloride, from about 50 to about 60 mM of sodium chloride, from about 48 to about 52 mM of sodium chloride, from about 49 mM to about 51 mM of sodium chloride, or about 50 mM of sodium chloride. In some detailed aspects, the buffer comprises about 20 mM of sodium phosphate and about 50 mM of sodium chloride. As an alternative to sodium phosphate, the buffer may comprise HEPES, Bis-Tris, MES, a succinate salt, or a citrate salt. As an alternative to sodium chloride, the buffer may comprise sodium sulfate or ammonium sulfate. The pH of the buffer may be from about 5 to about 9, preferably from about 6 to about 8, from about 6.8 to about 7.6, from about 6.9 to about 7.5, from about 7.0 to about 7.4, from about 7.1 to about 7.3, or about 7.2. The pH of the buffer may be about 6.8, about 6.9, about 7, about 7.1, about 7.2, about 7.3, about 7.4, about 7.5, or about 7.6.

The conductivity target of the equilibration (mS/cm) may range from about 1 mS/cm to about 40 mS/cm. The conductivity target of the equilibration (mS/cm) is preferably from about 6 mS/cm to about 10 mS/cm. The conductivity target may be from about 6 mS/cm to about 8 mS/cm, from about 7 mS/cm to about 9 mS/cm, from about 7 mS/cm to about 10 mS/cm, from about 8 mS/cm to about 10 mS/cm, from about 8 mS/cm to about 9 mS/cm, or about 8 mS/cm.

Loading of the antibody preparation onto the Protein A support is carried out at a temperature, in a volume, and for a time suitable to allow for maximal adsorption of the monoclonal antibodies to the Protein A ligand. Undesired materials that do not adsorb to the Protein A ligand flow through the support during chromatography. To further remove undesired materials that adhere to the ligand or to the antibody protein, the antibody-adsorbed support is preferably washed. Any suitable number of washes may be used, and the wash may comprise a buffer and sufficient stringency to remove undesired materials but not elute antibodies from the Protein A. The wash medium preferably is the same as the equilibration medium, in terms of make-up (e.g., sodium phosphate and sodium chloride) and pH.

The conductivity target of the wash may range from about 1 mS/cm to about 50 mS/cm. The conductivity target of the wash is preferably from about 6 mS/cm to about 10 mS/cm. The conductivity target may be from about 6 mS/cm to about 8 mS/cm, from about 7 mS/cm to about 9 mS/cm, from about 7 mS/cm to about 10 mS/cm, from about 8 mS/cm to about 10 mS/cm, from about 8 mS/cm to about 9 mS/cm, or about 8 mS/cm.

Following the wash, the monoclonal antibodies are eluted from the Protein A support. Elution may be carried out at a temperature, in a volume, and for a time suitable to allow for maximal elution yield of the monoclonal antibodies from the Protein A ligand. Elution buffer is preferably acidic. The elution buffer may comprise from about 10 mM to about 300 mM, from about 40 mM to about 120 mM acetic acid or sodium acetate, from about 50 mM to about 110 mM acetic acid or sodium acetate, from about 60 mM to about 100 mM acetic acid or sodium acetate, from about 70 mM to about 90 mM acetic acid or sodium acetate, from about 72 mM to about 88 mM acetic acid or sodium acetate, from about 75 mM to about 85 mM acetic acid or sodium acetate, from about 78 mM to about 82 mM acetic acid or sodium acetate, from about 79 mM to about 81 mM acetic acid or sodium acetate, from about 80 mM to about 90 mM acetic acid or sodium acetate, from about 70 mM to about 80 mM acetic acid or sodium acetate, of about 80 mM acetic acid or sodium acetate. As an alternative to acetic acid or sodium acetate, the elution buffer may comprise sodium citrate, sodium formate, or glycine. Sodium acetate is preferred. The elution buffer may comprise a pH of from about 2 to about 4.5, from about 3 to about 4, from about 3.2 to about 3.8, from about 3.3 to about 3.7, from about 3.4 to about 3.6, from about 3.3 to about 3.5, from about 3.5 to about 3.7, about 3.3, about 3.4, about 3.5, about 3.6, of about 3.7. Elution of the monoclonal antibody produces an eluate comprising the monoclonal antibody.

The eluate comprising the monoclonal antibody may be treated to inactivate any viruses present in the eluate. The virus inactivation may comprise acidifying the eluate at a temperature and for a period of time sufficient to inactivate any viruses present in the eluate. The acidification may comprise, for example, adding acetic acid, citric acid, hydrochloric acid, formic acid, or combination thereof to the eluate until a desired pH is achieved. The resultant pH of the acidified eluate may be from about 3 to about 4, from about 3.2 to about 3.8, from about 3.3 to about 3.7, from about 3.4 to about 3.6, from about 3.3 to about 3.5, or from about 3.5 to about 3.7, or about 3.3, about 3.4, about 3.5, about 3.6, or about 3.7. The eluate may be warmed to a temperature of from about 4° C. to about 25° C., and more preferably from about 18° C. to about 25° C. The eluate may be warmed before, during, or after acidification. Once at the desired inactivation temperature, the eluate is preferably maintained at both the pH and temperature for a period of time sufficient to inactivate substantially all latent viruses in the eluate. The eluate may be so maintained for about 10 to about 90 minutes, preferably from about 50 to about 80 minutes, and more preferably from about 60 to about 70 minutes.

After this virus inactivation hold time elapses, the pH of the eluate may be increased, for example, by addition of a suitable basic buffer such as Tris. The resultant pH of the eluate may be from about 7.3 to about 7.7, from about 7.3 to about 7.6, from about 7.3 to about 7.5, from about 7.4 to about 7.7, from about 7.4 to about 7.6, from about 7.4 to about 7.5, or from about 7.5 to about 7.7 or about 7.3, about 7.4, about 7.5, about 7.6, or about 7.7. Following the pH increase, the eluate may be filtered, for example, with a sterilizing grade 0.22 μm filter. Depth filtration may be used to filter the eluate, preferably as a first step of the filtration process. The depth filters may comprise mixed cellulose esters and borosilicate glass. Thus, depth filtration may precede sterilizing with the 0.22 μm filter.

Following the virus inactivation step, or following the Protein A elution if virus inactivation is not included, the monoclonal antibody may be further purified with a second chromatography step. Preferably, the chromatography employed in this step comprises a hybrid of anion exchange and hydrophobic interaction chromatography (AEX/HIC). In some aspects, the chromatography media comprises a support comprising a N-Benzyl-N-methyl ethanol amine ligand. A non-limiting example of a suitable media includes CAPTO® Adhere media. In some aspects, the chromatography media comprises a support comprising a hexylamine ligand. In some aspects, the chromatography media comprises a support comprising a phenylpropylamine ligand. The ligands may be linked to any suitable support, including but not limited to an agarose support or a cross-linked cellulose support.

The eluate from the Protein A chromatography step, which may be the filtered eluate from the virus inactivation step, is preferably loaded onto an AEX/HIC chromatography support. For example, an AEX/HIC chromatography support may comprise a N-Benzyl-N-methyl ethanol amine ligand (or hexylamine, phenylpropylamine, or other suitable ligand) and allowed to flow through the support. The support preferably has a binding capacity of from about 50 g/L to about 150 g/L, from about 60 g/L to about 140 g/L, from about 70 g/L to about 130 g/L, or from about 75 g/L to about 125 g/L.

Mass loading may play a role in the balance of purity versus yield. For adalimumab, from about 90 g/L to about 110 g/L of antibody may be loaded onto the AEX/HIC support. The mass loading of adalimumab may be from about 95 g/L to about 105 g/L, from about 96 g/L to about 104 g/L, from about 97 g/L to about 103 g/L, from about 98 g/L to about 102 g/L, from about 99 g/L to about 101 g/L, from about 95 g/L to about 100 g/L, from about 100 g/L to about 105 g/L, from about 90 g/L to about 105 g/L, from about 90 g/L to about 100 g/L, from about 100 g/L to about 110 g/L, from about 100 g/L to about 105 g/L, or about 100 g/L.

Prior to loading the eluate onto the AEX/HIC support, the support is preferably equilibrated. The equilibration medium may comprise a buffer. The buffer may comprise from about 10 mM to about 150 mM of HEPES, from about 25 mM to about 75 mM of HEPES, from about 30 mM to about 70 mM of HEPES, from about 35 mM to about 65 mM of HEPES, from about 40 mM to about 60 mM of HEPES, from about 45 mM to about 55 mM of HEPES, from about 47 mM to about 53 mM of HEPES, from about 49 mM to about 51 mM of HEPES, or about 50 mM of HEPES. In addition to HEPES, the buffer may comprise from about 40 mM to about 80 mM sodium chloride, from about 45 mM to about 75 mM sodium chloride, from about 50 mM to about 75 mM sodium chloride, from about 55 mM to about 75 mM sodium chloride, from about 55 mM to about 70 mM sodium chloride, from about 60 mM to about 70 mM sodium chloride, from about 64 mM to about 68 mM sodium chloride, from about 65 mM to about 70 mM sodium chloride, from about 65 mM to about 68 mM sodium chloride, from about 65 mM to about 67 mM sodium chloride, or about 66 mM sodium chloride. As an alternative to HEPES, the buffer may comprise sodium phosphate, potassium phosphate, Bis-Tris, MES, or a combination thereof. The pH of the buffer may be from about 6.0 to about 9.0, from about 7.3 to about 7.7, from about 7.3 to about 7.6, from about 7.3 to about 7.5, from about 7.4 to about 7.7, from about 7.4 to about 7.6, from about 7.4 to about 7.5, or from about 7.5 to about 7.7 or about 7.3, about 7.4, about 7.5, about 7.6, or about 7.7.

The conductivity target of the equilibration (mS/cm) may be from about 6 mS/cm to about 12 mS/cm. The conductivity target of the equilibration (mS/cm) is preferably from about 7.5 mS/cm to about 9.5 mS/cm. The conductivity target may be from about 7.7 mS/cm to about 9.3 mS/cm, from about 7.9 mS/cm to about 9.1 mS/cm, from about 8.1 mS/cm to about 8.9 mS/cm, from about 8.2 mS/cm to about 8.8 mS/cm, from about 8.3 mS/cm to about 8.7 mS/cm, from about 8.4 mS/cm to about 8.6 mS/cm, from about 8.0 mS/cm to about 8.5 mS/cm, from about 8.3 mS/cm to about 8.6 mS/cm, from about 8.3 mS/cm to about 8.5 mS/cm, from about 8.4 mS/cm to about 8.8 mS/cm, or about 8.5 mS/cm.

Loading of the eluate onto the AEX/HIC support is carried out at a temperature, in a volume, and for a time suitable to allow for maximal adsorption of impurities to the N-Benzyl-N-methyl ethanol amine ligand. The monoclonal antibodies preferably do not interact with the ligand, such that the monoclonal antibodies flow through the support during chromatography. Allowing the eluate to flow through the AEX/HIC support results in a flow-through pool comprising the monoclonal antibody. This flow-through pool includes fewer contaminating materials (e.g., residual Protein A, host cell proteins, DNA, etc.) relative to the Protein A eluate loaded onto the support.

It is believed that about 10% to about 20% of the acidic charge variants of the monoclonal antibodies may adsorb to the ligand during the AEX/HIC chromatography step. Thus, for example, if there are about 25% by weight of acidic charge variants in the initial monoclonal antibody preparation (as expressed by the cells), there may remain about 20-23% of acid charge variants in the flow-through from the AEX/HIC column.

Following the intermediate purification step (e.g., AEX/HIC chromatography), the monoclonal antibody may be still further purified with a third chromatography step. Preferably, the chromatography employed in this step comprises cation exchange chromatography (CEX). The level of impurities in the AEX/HIC flow through may be determined, and the CEX conditions may be adjusted to attain the desired level of clearance of the remaining impurities. A goal in this regard is to match the level of impurities in the final biosimilar product to the level of impurities in the reference product. For example, the wash conditions in the CEX may be adjusted to clear a higher or lower percentage of charge variants from the AEX/HIC flow through.

The AEX/HIC flow through may be loaded onto a CEX support. In some preferred aspects, the CEX support comprises a sulfapropyl ligand. A non-limiting example of a suitable media includes CAPTO® SP ImpRes media. In some aspects, the chromatography media comprises a support comprising a carboxymethyl, phosphate, sulfoethyl, or sulfonate ligand. The ligand may be linked to any suitable support, which may comprise an agarose, ceramic, hydrophilic polymer, polymeric bead, polystyrene-divinyl benzene, or polyvinyl ether support. In highly preferred aspects, CEX chromatography is used as the polishing purification step, and follows AEX/HIC chromatography, which is used as the intermediate purification step. In some aspects, CEX/HIC chromatography may be used as the polishing purification step. Using CEX or CEX/HIC chromatography as the polishing purification step (following AEX/HIC chromatography) represents an inversion of the customary practice in the art, which is to use CEX chromatography as the intermediate purification step and AEX/HIC chromatography as the polishing chromatography step. It is believed that this inversion provides for enhanced removal of acid charge variants of the monoclonal antibody relative to carrying out the chromatography steps in the customary order, with CEX chromatography before the AEX/HIC chromatography.

The flow-through pool from the AEX/HIC chromatography step is preferably loaded onto the chromatography support comprising a sulfonate ligand (or carboxymethyl, phosphate, sulfoethyl, or sulfonate ligand) and allowed to flow through the support, whereby the antibodies interact with the sulfonate ligand. The support preferably comprises particles that may be packed into a chromatography column. The support preferably has an antibody binding capacity of from about 20 g/L to about 80 g/L, from about 25 g/L to about 75 g/L, from about 30 g/L to about 70 g/L, from about 30 g/L to about 65 g/L, from about 30 g/L to about 60 g/L, from about 30 g/L to about 55 g/L, from about 30 g/L to about 50 g/L, from about 25 g/L to about 65 g/L, from about 20 g/L to about 60 g/L, from about 25 g/L to about 50 g/L, from about 20 g/L to about 50 g/L, or from about 20 g/L to about 60 g/L.

Prior to loading the flow-through pool onto the CEX support, the support is preferably equilibrated. The equilibration medium may comprise a buffer. The buffer may comprise from about 1 mM to about 100 mM of sodium phosphate. The buffer may comprise from about 5 mM to about 50 mM of sodium phosphate. The buffer may comprise from about 10 mM to about 40 mM of sodium phosphate, from about 15 mM to about 35 mM of sodium phosphate, from about 15 mM to about 30 mM of sodium phosphate, from about 17 mM to about 28 mM of sodium phosphate, from about 10 mM to about 30 mM of sodium phosphate, from about 20 mM to about 30 mM of sodium phosphate, from about 20 mM to about 28 mM of sodium phosphate, from about 20 mM to about 25 mM of sodium phosphate, from about 15 mM to about 25 mM of sodium phosphate, or from about 24 mM to about 25 mM of sodium phosphate, or about 25 mM of sodium phosphate. As an alternative to sodium phosphate, the buffer may comprise a citrate salt, a succinate salt, MES, Bis-Tris, HEPES, or histidine. The pH of the buffer may be from about 5.0 to about 7.0, from about 5.2 to about 6.8, from about 5.6 to about 6.8, from about 5.6 to about 6.6, from about 5.8 to about 6.6, from about 5.9 to about 6.5, from about 6.0 to about 6.4, from about 6.1 to about 6.3, or about 6.2. The pH of the buffer may be about 5.0, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, or about 7.0.

The conductivity target of the equilibration (mS/cm) is preferably from about 1 mS/cm to about 4 mS/cm. The conductivity target may be from about 1 mS/cm to about 3.6 mS/cm, from about 1 mS/cm to about 3 mS/cm, from about 1.5 mS/cm to about 3.5 mS/cm, from about 2 mS/cm to about 3 mS/cm, or from about 2 mS/cm to about 2.5 mS/cm, or about 2.3 mS/cm.

Loading of the flow-through pool comprising the monoclonal antibody onto the CEX support is carried out at a temperature, in a volume, and for a time suitable to allow for maximal adsorption of the monoclonal antibodies to the ligand support. Undesired materials that do not adsorb to the ligand support flow through the support during chromatography.

To further remove undesired materials that adhere to the ligand, the antibody-adsorbed support is preferably washed. The washing removes a significant percentage of acid charge variants in the flow-through pool. Any suitable number of washes may be used, and the wash may comprise a buffer and sufficient stringency to remove acid charge variants, but not a substantial portion of non-variant antibodies from the ligand. It is preferable that the chromatography support be washed at least three times for acidic species removal.

The first wash for acidic species removal preferably comprises the same buffer used to equilibrate the CEX support. Thus, for example, the antibody-adsorbed CEX support may be washed with a buffer comprising a pH and a conductivity target as in the column equilibration.

The second wash for acidic species removal may optionally additionally comprise a salt, such as sodium chloride. Thus, the second wash solution may comprise sodium phosphate and sodium chloride. The wash may comprise sodium phosphate at any concentration (mM) described or exemplified herein. As an alternative to sodium phosphate, the wash may comprise a citrate salt, a succinate salt, MES, Bis-Tris, HEPES, or histidine. If sodium chloride is included, the wash may comprise from about 1 mM to about 100 mM of sodium chloride, from about 30 mM to about 60 mM of sodium chloride, from about 35 mM to about 55 mM sodium chloride, from about 40 mM to about 50 mM sodium chloride, from about 41 mM to about 49 mM sodium chloride, from about 42 mM to about 48 mM sodium chloride, from about 43 mM to about 47 mM sodium chloride, from about 43 mM to about 46 mM sodium chloride, from about 43 mM to about 45 mM sodium chloride, from about 42 mM to about 45 mM sodium chloride, from about 42 mM to about 44 mM sodium chloride, or from about 43 mM to about 44 mM sodium chloride. The wash may comprise about 40 mM sodium chloride, about 41 mM sodium chloride, about 42 mM sodium chloride, about 43 mM sodium chloride, about 44 mM sodium chloride, about 45 mM sodium chloride, about 46 mM sodium chloride, about 47 mM sodium chloride, or about 48 mM sodium chloride. About 44 mM sodium chloride is preferred. The pH of the wash may be from about 5.0 to about 7.0, from about 5.2 to about 6.8, from about 5.6 to about 6.8, from about 5.6 to about 6.6, from about 5.8 to about 6.6, from about 5.9 to about 6.5, from about 6.0 to about 6.4, from about 6.1 to about 6.3, or about 6.2. The pH may be about 5.0, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, or about 7.0.

The conductivity target of the second wash (mS/cm) is preferably from about 6.6 mS/cm to about 7.6 mS/cm. The conductivity target may be from about 3 mS/cm to about 5.6 mS/cm, from about 3.6 mS/cm to about 5.6 mS/cm, from about 4 mS/cm to about 6 mS/cm, from about 4 mS/cm to about 5.6 mS/cm, from about 4.2 mS/cm to about 5.8 mS/cm, from about 4.3 mS/cm to about 5.5 mS/cm, from about 4.4 mS/cm to about 4.6 mS/cm, from about 4.5 mS/cm to about 5.5 mS/cm, from about 5 to about 7, from about 6 to about 7, from about 6.7 mS/cm to about 7.5 mS/cm, from about 6.8 mS/cm to about 7.4 mS/cm, from about 6.9 mS/cm to about 7.3 mS/cm, or from about 7 mS/cm to about 7.2 mS/cm, about 7.1 mS/cm or about 7.2 mS/cm.

The third wash for acidic species removal preferably comprises the same buffer used to equilibrate the CEX support. Thus, for example, the antibody-adsorbed CEX support may be washed a third time with a buffer comprising a pH and a conductivity target as in the column equilibration. The third wash preferably does not include sodium chloride. The third wash may effectively quench the acidic species removal from the second wash, as the conductivity target is lowered.

Washing during the CEX polishing chromatography step preferably removes acid charge variants of the monoclonal antibodies. A balance is preferred, in which a desired amount of acid charge variants is removed from the antibody population, yet a maximal amount of desired (non-variant) monoclonal antibodies are retained on the support for subsequent elution. It was observed that a more stringent wash could remove additional acid charge variants, but such a more stringent wash also removed more desired (non-variant) monoclonal antibodies, and conversely, a less stringent wash could retain more of the desired population of non-variant antibodies, but would remove fewer acid charge variants. It was further observed that monitoring the UV absorbance (e.g., at UV A280) in the CEX chromatography system during the second wash can facilitate achievement of an appropriate balance between antibody (non-variant) yield and acid charge variant removal. Column volume measurements may be used in the alternative to UV absorbance. When this balance is achieved, the stringency in the second wash is quenched by the initiation of the third wash.

Thus, for acid charge variant removal, the polishing chromatography step preferably includes monitoring of UV absorbance, and determining the peak of absorbance during the second wash, then determining when the absorbance diminishes from about 5% to about 20%, and then quenching the salt (sodium chloride) stringency by washing the CEX support with the third wash (e.g., equilibration) buffer. Preferably, the third wash is initiated when the absorbance diminishes from about 5% to about 15%, or from about 5% to about 14%, or from about 5% to about 13%, or from about 5% to about 12%, or from about 5% to about 11%, or from about 5% to about 10%, or from about 6% to about 15%, or from about 6% to about 14%, or from about 6% to about 13%, or from about 6% to about 12%, or from about 6% to about 11%, or from about 6% to about 10%, or from about 7% to about 15%, or from about 7% to about 14%, or from about 7% to about 13%, or from about 7% to about 12%, or from about 8% to about 15%, or from about 8% to about 14%, or from about 8% to about 13%, or from about 9% to about 15%, or from about 9% to about 14%, or from about 9% to about 13%, or from about 10% to about 15%, or from about 10% to about 14% of the peak absorbance units.

The CEX polishing step may also remove basic charge variants. Steps for removal of basic charge variants may be in addition to the steps for removal of acid charge variants, or in the alternative to steps for removal of acid charge variants (e.g., CEX polishing may be employed to remove acidic species, basic species, or both acidic and basic species). In some preferred aspects, both acid and basic charge variants are removed by CEX chromatography polishing. Basic charge variants may be removed by a gradient or stepwise elution, and not via washing of the support.

Prior to gradient elution for basic species removal, the support may be washed using the same buffer used to equilibrate the CEX support. Thus, for example, the antibody-adsorbed CEX support may be washed with a buffer comprising from about 5 mM to about 50 mM of sodium phosphate at a pH of from about 6.4 to about 7.2, and a conductivity target of from about 1 mS/cm to about 4 mS/cm, as set forth above. The wash may comprise from about 1 mM to about 100 mM of sodium phosphate. The buffer may comprise from about 5 mM to about 50 mM of sodium phosphate. The buffer may comprise from about 10 mM to about 40 mM of sodium phosphate, from about 15 mM to about 35 mM of sodium phosphate, from about 15 mM to about 30 mM of sodium phosphate, from about 17 mM to about 28 mM of sodium phosphate, from about 10 mM to about 30 mM of sodium phosphate, from about 20 mM to about 30 mM of sodium phosphate, from about 20 mM to about 28 mM of sodium phosphate, from about 20 mM to about 25 mM of sodium phosphate, from about 15 mM to about 25 mM of sodium phosphate, or from about 24 mM to about 25 mM of sodium phosphate, or about 25 mM of sodium phosphate. As an alternative to sodium phosphate, the buffer may comprise a citrate salt, a succinate salt, MES, Bis-Tris, HEPES, or histidine. The pH of the buffer may be from about 6.4 to about 7.2, from about 6.4 to about 7.1, from about 6.5 to about 7.1, from about 6.5 to about 7.0, from about 6.5 to about 6.9, from about 6.6 to about 7.0, from about 6.6 to about 6.9, from about 6.7 to about 6.9, from about 6.8 to about 6.9, from about 6.6 to about 6.8, from about 6.5 to about 6.7, or from about 6.8 to about 7.0. The pH of the buffer may be about 6.4, about 6.5, about 6.6, about 6.7, about 6.8, about 6.9, about 7.0, about 7.1, or about 7.2.

The conductivity target of the wash (mS/cm) is preferably from about 1 mS/cm to about 4 mS/cm. The conductivity target may be from about 1 mS/cm to about 3.6 mS/cm, from about 1 mS/cm to about 3 mS/cm, from about 1.5 mS/cm to about 3.5 mS/cm, from about 2 mS/cm to about 3 mS/cm, or from about 2 mS/cm to about 2.5 mS/cm, or about 2.3 mS/cm.

Following washing (e.g., under an acidic species and/or basic species removal protocol), the monoclonal antibodies are eluted from the CEX support. Elution may be carried out at a temperature, in a volume, and for a time suitable to allow for maximal elution yield of the monoclonal antibodies from the ligand support.

The elution buffer may comprise sodium phosphate at any concentration (mM) described or exemplified herein. As an alternative to sodium phosphate, the elution buffer may comprise a citrate salt, a succinate salt, MES, Bis-Tris, HEPES, or histidine. The elution buffer also comprises from about 75 mM to about 500 mM sodium chloride, from about 100 mM to about 500 mM, from about 80 mM to about 120 mM of sodium chloride, from about 80 mM to about 110 mM sodium chloride, from about 80 mM to about 100 mM sodium chloride, from about 90 mM to about 120 mM sodium chloride, from about 90 mM to about 110 mM sodium chloride, from about 90 mM to about 105 mM sodium chloride, from about 95 mM to about 120 mM sodium chloride, from about 95 mM to about 115 mM sodium chloride, from about 95 mM to about 110 mM sodium chloride, from about 95 mM to about 105 mM sodium chloride, or from about 98 mM to about 102 mM sodium chloride. The elution buffer may comprise about 80 mM sodium chloride, about 85 mM sodium chloride, about 90 mM sodium chloride, about 95 mM sodium chloride, about 96 mM sodium chloride, about 97 mM sodium chloride, about 98 mM sodium chloride, about 99 mM sodium chloride, about 100 mM sodium chloride, about 101 mM sodium chloride, about 102 mM sodium chloride, about 103 mM sodium chloride, about 104 mM sodium chloride, or about 105 mM sodium chloride. About 100 mM sodium chloride is preferred. As an alternative to sodium chloride, ammonium sulfate or sodium sulfate may be used.

The pH of the elution buffer may be from about 5.0 to about 7.0, from about 5.8 to about 6.6, from about 5.9 to about 6.5, from about 6.0 to about 6.4, from about 6.1 to about 6.3, or about 6.2. The pH of the buffer may be about 5.8, about 5.9, about 6, about 6.1, about 6.2, about 6.3, about 6.4, about 6.5, or about 6.6. The conductivity target of the elution (mS/cm) is preferably from about 10 mS/cm to about 14 mS/cm. The conductivity target may be from about 11 mS/cm to about 14 mS/cm, from about 11 mS/cm to about 13 mS/cm, from about 12 mS/cm to about 14 mS/cm, from about 12 mS/cm to about 13 mS/cm, from about 12.3 mS/cm to about 13.3 mS/cm, from about 12.5 mS/cm to about 13.1 mS/cm, or from about 12.6 mS/cm to about 13 mS/cm, or about 12.8 mS/cm. Elution buffer where only basic charge variants of the antibody are removed may be run using a linear gradient or employing a step elution in an isocratic mode.

It is preferred that acidic species are removed via washing with a higher stringency as described above. While the column may be washed during a basic species removal, the washing is less stringent than for acidic species removal; instead, basic species are removed via increasing stringency in the elution buffer. If acidic species have been washed from the support and removal of basic species is not desired, the antibody is eluted from the CEX column with the elution buffer at a fixed concentration of sodium chloride. If removal of basic species is desired (whether or not acidic species have been washed from the support), the antibody is eluted from the CEX column using elution buffer with an increasing concentration of sodium chloride. The increase in sodium chloride may be achieved via a linear gradient, whereby the elution buffer at the inception of the elution stage has a lower concentration of sodium chloride, and as the elution stage progresses, sodium chloride is added to the elution buffer at a substantially constant rate in order to attain the highest desired concentration of sodium chloride for antibody elution. Alternatively, the increase in sodium chloride may be achieved in steps, whereby the elution buffer at the inception of the elution stage has a lower concentration of sodium chloride, and after a period of time elapses, the elution buffer is changed to include a buffer with a higher concentration of sodium chloride. Any suitable number of stepwise enhancements of the sodium chloride concentration may be used, with two or three step increases being preferred.

It is believed that about 25% to about 60% of the remaining acidic charge variants of the monoclonal antibodies are removed by the second wash during the CEX chromatography step. Thus, for example, if there are about 20-23% by weight of acid charge variants in the flow-through from the AEX/HIC column, there will remain about 8% to about 20% by weight of acid charge variants in the eluate from the CEX column. Preferably, about 10% to about 14% by weight of acid charge variants are in the eluate from the CEX column, as measured by CEX-HPLC. Preferably, about 15% to about 17% by weight of acid charge variants are in the eluate from the CEX column, as measured by icIEF. In some aspects, about 10% to about 12% by weight of acid charge variants are in the eluate from the CEX column, as measured by either CEX-HPLC or icIEF. In some aspects, about 11% to about 13% by weight of acid charge variants are in the eluate from the CEX column, as measured by either CEX-HPLC or icIEF. In some aspects, about 12% to about 14% by weight of acid charge variants are in the eluate from the CEX column, as measured by either CEX-HPLC or icIEF. In some aspects, about 14% to about 18% by weight of acid charge variants are in the eluate from the CEX column, as measured by either CEX-HPLC or icIEF. In some aspects, about 13% to about 19% by weight of acid charge variants are in the eluate from the CEX column, as measured by either CEX-HPLC or icIEF. In some aspects, about 14% to about 17% by weight of acid charge variants are in the eluate from the CEX column, as measured by either CEX-HPLC or icIEF. In some aspects, about 8%, about 9%, about 10%, about 11%, about 12%, about 13%, about 14%, about 15%, about 16%, or about 17% by weight of acid charge variants are in the eluate from the CEX column, as measured by either CEX-HPLC or icIEF.

It is believed that about 25% to about 60% of the remaining basic charge variants of the monoclonal antibodies are removed by using a linear gradient or step elution process to remove the tailing shoulder that is evident during the elution phase of the CEX chromatography step. Thus, for example, there will remain about 5% to about 35% by weight of basic charge variants in the eluate from the CEX column. Preferably, about 10% to about 30% by weight of basic charge variants are in the eluate from the CEX column, as measured by any suitable technique, for example, CEX-HPLC or icIEF. In some aspects, about 15% to about 25% by weight of basic charge variants are in the eluate from the CEX column, as measured by any suitable technique. In some aspects, about 15% to about 30% by weight of basic charge variants are in the eluate from the CEX column, as measured by any suitable technique. In some aspects, about 12% to about 27% by weight of basic charge variants are in the eluate from the CEX column, as measured by any suitable technique. In some aspects, about 18% to about 23% by weight of basic charge variants are in the eluate from the CEX column, as measured by any suitable technique. In some aspects, about 20% to about 25% by weight of basic charge variants are in the eluate from the CEX column, as measured by any suitable technique. In some aspects, about 19% to about 22% by weight of basic charge variants are in the eluate from the CEX column, as measured by any suitable technique. In some aspects, about 17% to about 21% by weight of basic charge variants are in the eluate from the CEX column, as measured by any suitable technique. In some aspects, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight of basic charge variants are in the eluate from the CEX column, as measured by any suitable technique.

The CEX-HPLC testing method monitors charge heterogeneity, including C-terminal variants, via weak cation exchange chromatography at a pH range of 5.6 to 8.0. The method may employ, for example, a Dionex ProPac™ WCX-10 column with a MES/sodium phosphate/sodium chloride gradient, with UV absorbance monitored at 280 nm. Distinct peaks eluting after the main peak are considered basic species, and peaks eluting prior to the main peak are considered acidic species.

Imaged capillary isoelectric focusing (icIEF) is a high-resolution imaging technique for protein separation and detection based on differences in their isoelectric points (pI). The icIEF method uses a Protein Simple iCE3 system, together with Alcott autosampler. Following addition of the protein sample to a mixture of ampholytes, stabilizers methylcellulose and pI markers, the solution is injected into a fluorocarbon (FC)-coated capillary. The protein sample is then separated and analyzed using two steps of focusing. The system first pre-focusing step mobilizes the samples in the mixture of ampholytes at 1,500 kV. Next, the system second focusing applies a higher voltage at 3,000 kV across the capillary forming a pH gradient through the introduction of hydronium ions from the anolyte and hydroxyl ions from the catholyte at the opposite end of the capillary. The pH gradient forms at the capillary ends and then progresses toward the center of the capillary where both anodic and cathodic sides merge. Bidirectional focusing of the protein sample occurs by allowing the test article proteins to migrate and finally settle at their specific pI values. As a result, the pH gradient is titrated from basic to acidic and the protein charge variants can be separated according to the differences in pI values and are then detected at 280 nm as the proteins obtain a positive charge and migrate toward the cathode by whole column imaging using a CCD camera.

The eluate from the CEX column contains purified monoclonal antibodies with a minimal amount of acid charge variants and/or a minimal amount of basic charge variants. The eluate may be further processed in order that the monoclonal antibodies may be in a form suitable for therapeutic administration, for example, to a human patient. The further processing may include any combination of nanofiltration, concentration, and diafiltration of the eluate.

Nanofiltration may comprise filtering the eluate from the CEX column (including the monoclonal antibodies and remaining charge variants) through a filter having an about 15 nm pore size, or about 20 nm pore size. Nanofiltration may remove viruses and precipitates present in the eluate.

Concentration may comprise ultrafiltration, using a membrane with an appropriate molecular weight cutoff. Both ultrafiltration and diafiltration may be carried out according to standard methodologies, using standard equipment as is practiced in the art.

The monoclonal antibodies, pooled and purified according to the chromatography, virus inactivation, filtration, and concentration modalities described above may be formulated for storage and therapeutic administration to patients. The monoclonal antibody formulation may be for subcutaneous administration to patients. In some aspects, the monoclonal antibody pool comprises about 51% to about 75% by weight of non-variant antibodies (not basic species or acid species), from about 10% to about 14% by weight of acid charge variants of the monoclonal antibody, and from about 15% to about 35% by weight of basic charge variants of the monoclonal antibody. This antibody pool may be formulated with an aqueous buffer and a non-ionic surfactant, and the formulation may comprise from about 30 mg to about 55 mg of the monoclonal antibody pool (to include the non-variant antibodies and the charge variants). In some aspects, the formulation comprises from about 35 mg to about 45 mg of the antibody pool. In some aspects, the formulation comprises from about 45 mg to about 55 mg of the antibody pool. In some preferred aspects, the formulation comprises from about 40 mg to about 50 mg of the antibody pool. In some preferred aspects, the formulation comprises about 40 mg of the antibody pool. In some preferred aspects, the formulation comprises about 45 mg of the antibody pool. In some highly preferred aspects, the formulation comprises about 50 mg of the antibody pool. The antibody is preferably dosed at a total of 40 mg and about 0.8 mg/mL of the antibody.

The buffer may comprise from about 0.8 mM to about 1.2 mM of sodium acetate trihydrate, or from about 0.9 mM to about 1.1 mM of sodium acetate trihydrate, or about 1 mM of sodium acetate trihydrate. The buffer may comprise from about 201 mM to about 205 mM of mannitol, or from about 202 mM to about 204 mM of mannitol, or about 203 mM of mannitol. The buffer may comprise from about 17 mM to about 21 mM of glacial acetic acid, or from about 18 mM to about 20 mM of glacial acetic acid, or about 19 mM of glacial acetic acid. The buffer may comprise from about 25 mM to about 27 mM of sodium chloride, or about 26 mM of sodium chloride, or about 27 mM of sodium chloride, or about 26.35 mM of sodium chloride.

The buffered antibody formulation may include polysorbate 80 as a non-ionic surfactant. In some aspects, the formulation comprises from about 0.08% (v/v) to about 0.12% (v/v) of polysorbate 80. In some aspects, the formulation comprises from about 0.09% (v/v) to about 0.11% (v/v) of polysorbate 80. In some aspects, the formulation comprises about 0.1% (v/v) of polysorbate 80.

In a detailed aspect, a buffered antibody formulation comprises (a) about 40 mg to about 60 mg, preferably about 50 mg of the monoclonal antibody pool (to include the non-variant antibodies and the charge variants), (b) a buffer comprising about 1 mM of an acetate salt, preferably sodium acetate trihydrate, about 203 mM of mannitol, about 19 mM of glacial acetic acid, and about 26.35 mM of sodium chloride, and (c) about 0.1% (by volume) of polysorbate 80. The buffered monoclonal antibody formulation has a pH of from about 5.1 to about 5.3, preferably about 5.2. In some aspects, the formulation comprises from about 35 mg to about 45 mg of the antibody pool. In some aspects, the formulation comprises from about 45 mg to about 55 mg of the antibody pool. In some preferred aspects, the formulation comprises from about 40 mg to about 50 mg of the antibody pool. In some preferred aspects, the formulation comprises about 40 mg of the antibody pool. In some preferred aspects, the formulation comprises about 45 mg of the antibody pool. In some highly preferred aspects, the formulation comprises about 50 mg of the antibody pool. The antibody is preferably dosed at a total of 40 mg and about 0.8 mg/mL of the antibody.

The following examples are provided to describe the invention in greater detail. They are intended to illustrate, not to limit, the invention.

Example 1

Affinity Capture

Protein-A affinity capture step is an inherently robust processing step, with a rich platform performance history. Process impurities such as host cell proteins (HCP) and DNA are removed during the flow-through and wash phases of the step. A low pH buffer eluted the bound adalimumab antibody from the resin and set up the low pH viral inactivation step described in Example 2. Four resins were screened for use using a base process (Tables 1 and 2).

TABLE 1

Protein A Resins Screened

| Resin | Supplier | Matrix | Bead Size (um) | Flow Rate (cm/h) | Theoretical DBC (g/L) |
|---|---|---|---|---|---|
| ABSELECT SURE ® | GE | Rigid Agarose | 85 | 100-500 | 30-35 |
| UNOsphere ™ SUPrA | Bio-Rad | Crosslinked Polymer | 57 | 100-600 (150 cm/h) | 30 |
| PROSEP ® Ultra Plus | Millipore | Glass | 60 | 500 | 50 |
| ABSOLUTE ® HiCap | Novasep | Silica | 35 | 500 | 55 |

TABLE 2

Protein A Screening Process

| Chromatography Step | Parameter |
|---|---|
| Equilibration | 20 mM sodium phosphate, 150 mM sodium chloride, pH 7.2 |
| Sample Loading | adalimumab (Residence time = 2 min) |
| Wash | 20 mM sodium phosphate, 150 mM sodium chloride, pH 7.2 |
| Elution | 80 mM acetic acid, pH 3.5 |
| CIP | 50 mM sodium hydroxide, 1M sodium chloride |
| Re-equilibration | 20 mM sodium phosphate, 150 mM sodium chloride, pH 7.2 |

During Protein A resin screening, assessment of purity measured by size exclusion chromatography (SEC) as well as product yield were taken into account. Additionally, flow characteristics of the resins (e.g., compressibility, bead matrix and maximum and recommended flow rates) were assessed as they impact resolution of the product and processing times. A summary of the resulting data from the resin screen is shown in Table 3. MabSelect SuRe™ (GE Healthcare) was selected based on an initial dynamic binding capacity (DBC) of 35 g/L as well as a purity of nearly 97% monomer. The product recovery following elution of the material was 99% monomer. The material can be used at flow rates up to 500 cm/h allowing favorable processing times and minimal bead compression.

TABLE 3

Summary of Protein A Resin Screen

| Resin | Measured DBC (g/L) | % Recovery | Purity % Monomer | Rank |
|---|---|---|---|---|
| MABSELECT SURE® | 35 | 99 | 96.9 | 1 |
| UNOsphere™ SUPrA | 28 | 97 | 95.0 | 2 |
| PROSEP® Ultra Plus | 39 | 88 | 96.8 | 3 |
| ABSOLUTE® HiCap | 58 τ = 3 min | 75 | 96.0 | 4 |

Figure 2:
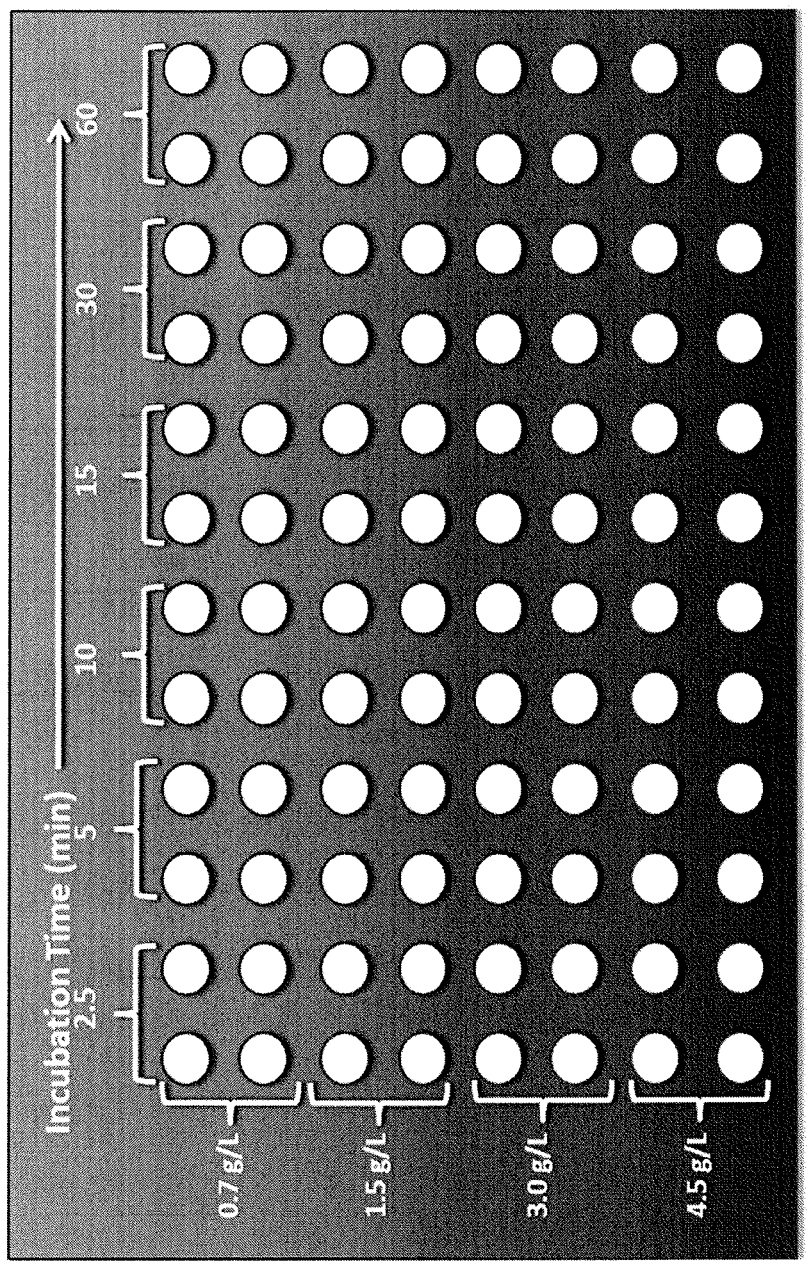
FIG. 2 shows a protein uptake study design based on the MABSELECT SURE® resin.

A protein uptake experiment was performed to enable a prediction of dynamic binding capacity at 10% breakthrough while varying residence times (τ) using a calculation of static binding capacity. The uptake study also enables the calculation of the adsorption isotherm for adalimumab with the selected chromatography resin. The design of the experiment is shown in FIG. 2. The base process was used previously described in Table 2. The protein uptake study was designed to utilize 96 well format to maximize product and buffer solutions.

Figure 3:
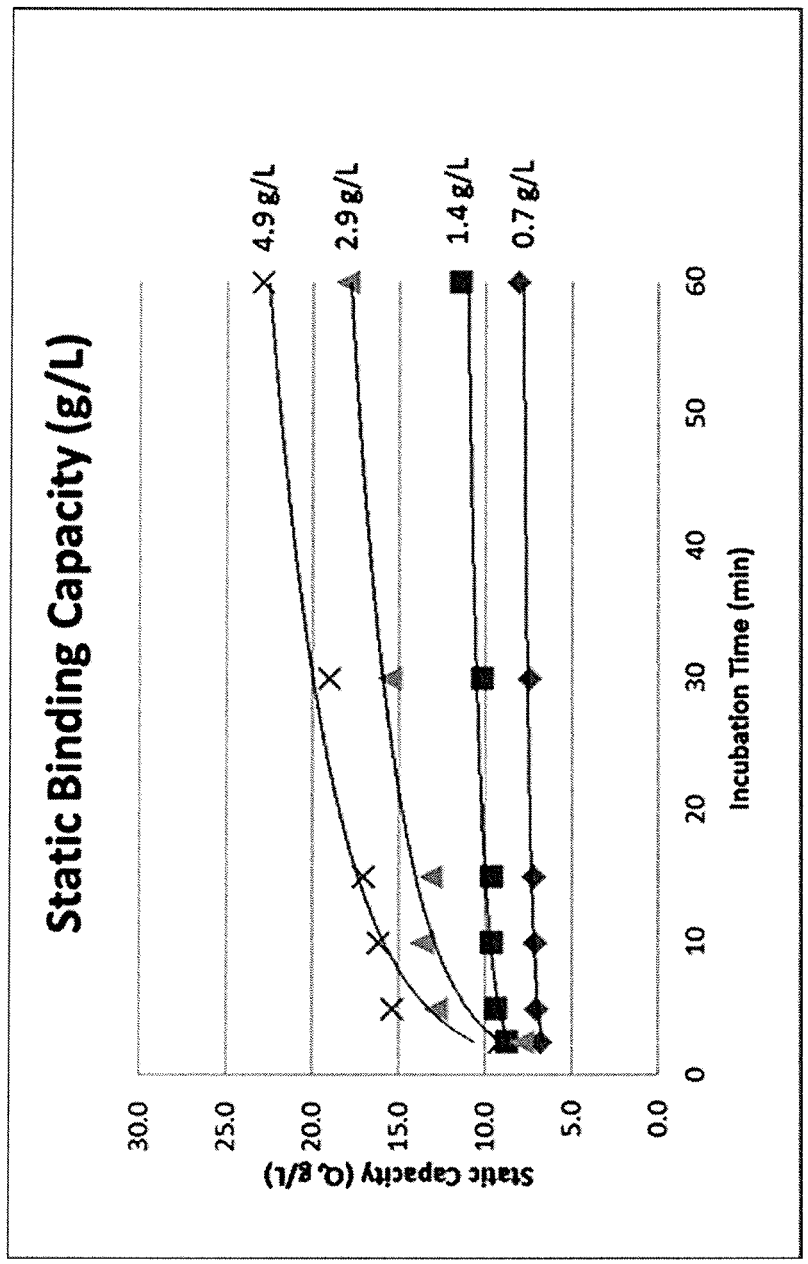
FIG. 3 shows static binding capacity (g/L).
Figure 4:
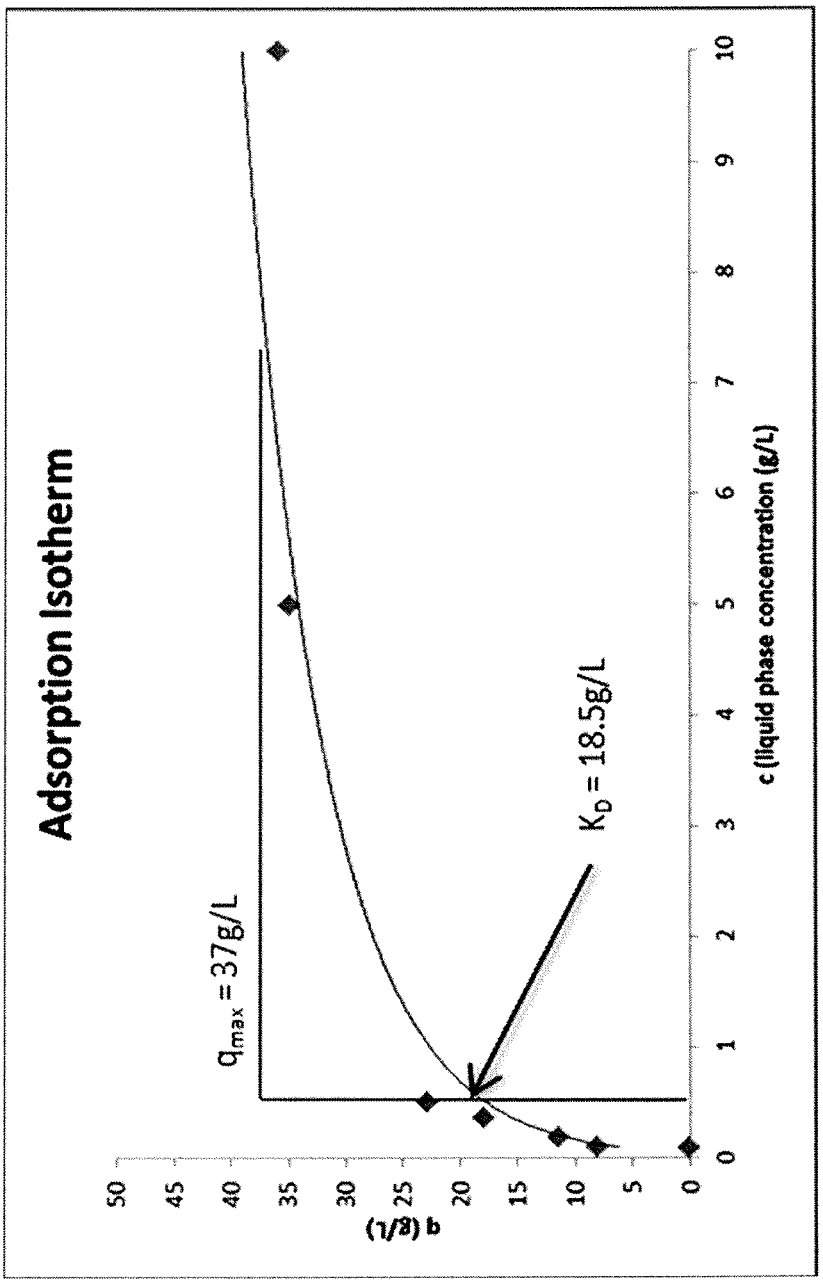
FIG. 4 shows MabSelect SuRe® adsorption isotherm for adalimumab.

Static binding (Q) capacity of adalimumab with MabSelect SuRe® was determined using the following Equation 1 and the data is shown in FIG. 3. The static binding capacity was then used to generate an adsorption isotherm (Equation 2) which predicts a dynamic binding capacity (qmax) shown in FIG. 4

$$Q = \frac{C_{elution} \times V_{elution}}{V_{media}}$$  Equation 1

Static binding capacity ($Q$)

$C_{elution}$ = adalimumab concentration in eluate pool (mg/mL)
$V_{elution}$ = elution volume (mL)
$V_{medium}$ = volume of resin in well (mL).

$$Q = (C_0 - C)\frac{V_{liquid}}{V_{media}}$$  Equation 2

Adsorption isotherm $C_0$ = adalimumab concentration (mg/mL)
$C$ = adalimumab concentration in the liquid phase after incubation (mg/mL)
$V_{liquid}$ = elution volume (mL)
$V_{medium}$ = volume of resin in well (mL).

The prediction of dynamic binding capacity from the derivation of the static binding capacity is in agreement with the data generated during the resin screen of 35 g/L binding capacity of adalimumab when using MabSelect SuRe® under the chromatographic conditions described. An effort to improve binding capacity was made focusing on the concentration of NaCl used in the equilibration or binding buffer used. Sodium chloride concentrations ranging from 0 to 150 mM were evaluated in the same 20 mM sodium phosphate buffer, pH 7.2 and a residence time of 4 minutes for their impact on binding capacity. The data are shown in Table 4.

TABLE 4

Impact of NaCl concentration on DBC for adalimumab - MabSelect SuRe®

| NaCl Concentration (mM) | Residence Time (min) | Linear Flow Rt (cm/h) | DBC @ 10% BT (g/L) | Operating DBC (g/L) |
|---|---|---|---|---|
| 0 | 4 | 300 | 51.5 | 60.6 |
| 50 | 4 | 300 | 50 | 59 |
| 100 | 4 | 300 | 46.7 | 54.9 |
| 150 | 4 | 300 | 37.1 | 43.6 |

Figure 5:
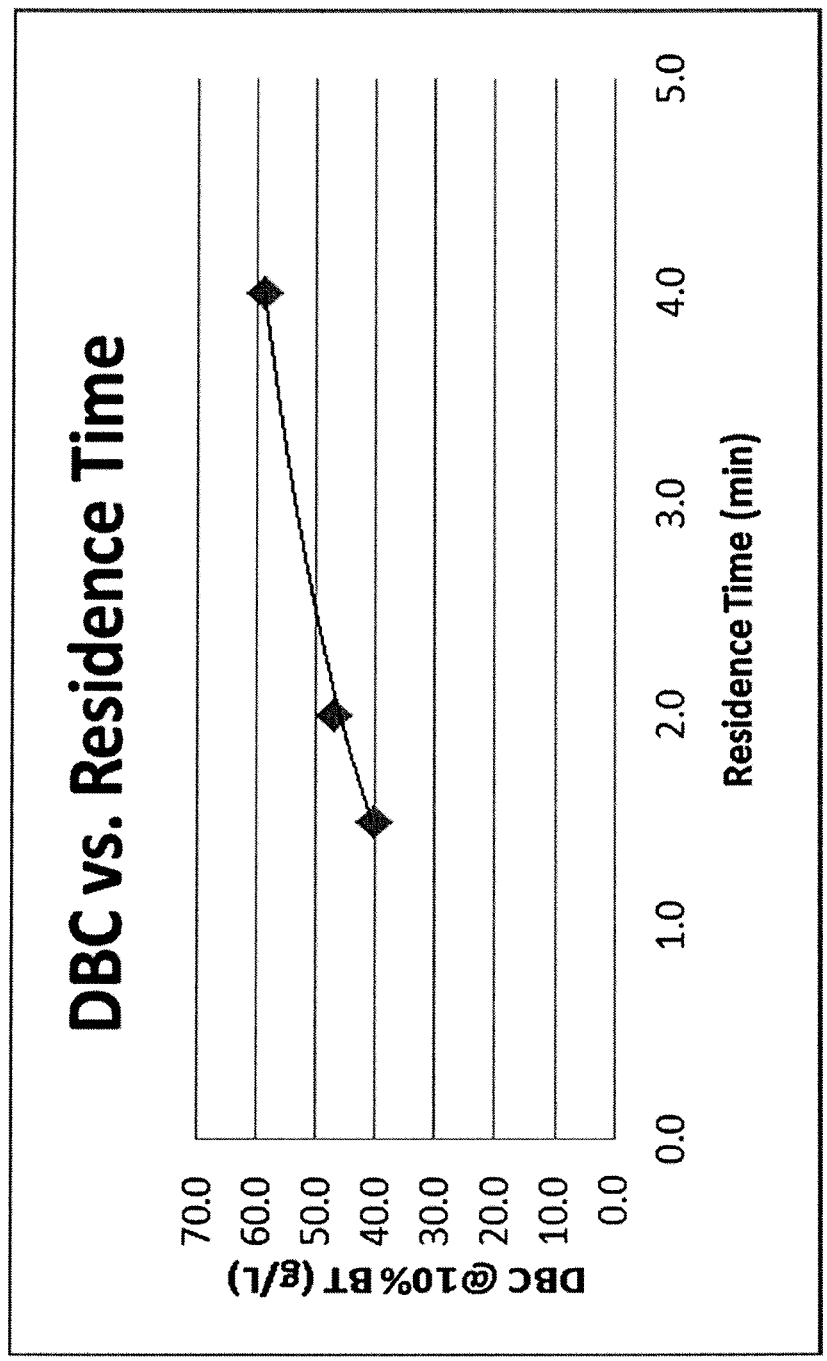
FIG. 5 shows a relationship between dynamic binding capacity and residence time.
Figure 6:
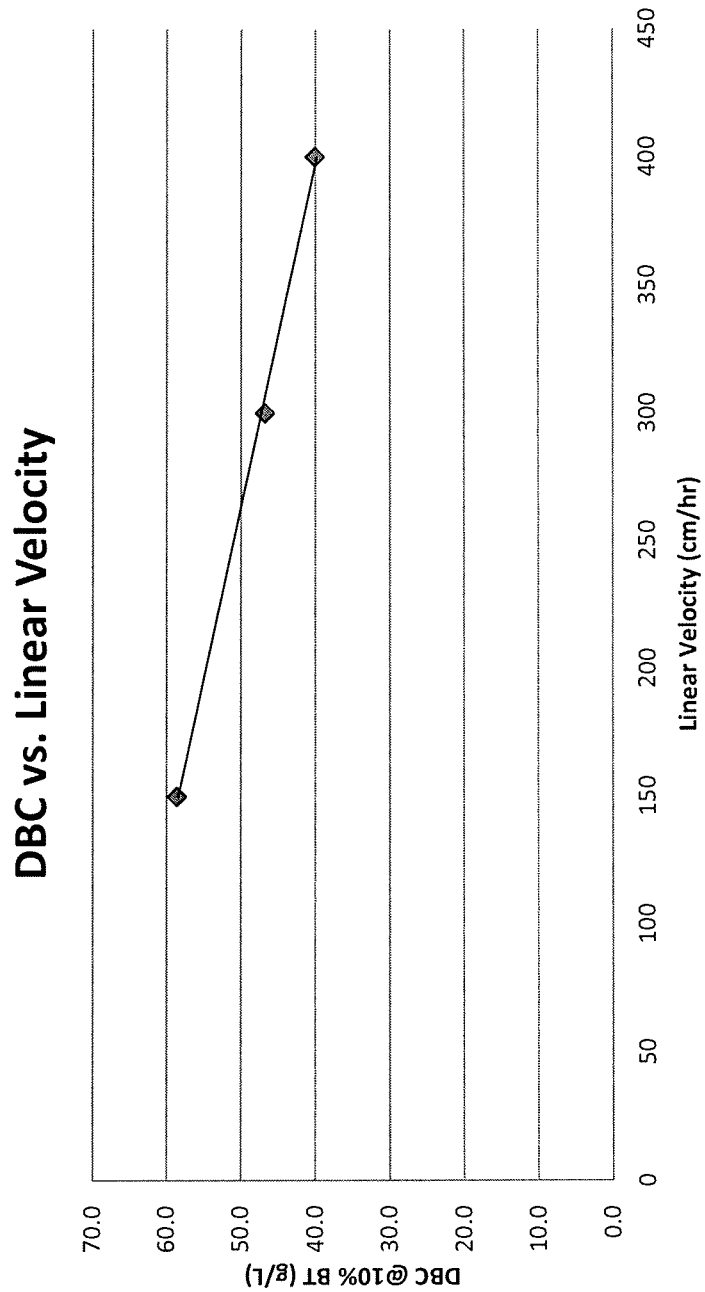
FIG. 6 shows a relationship between dynamic binding capacity and linear velocity.

A sodium chloride concentration of 50 mM was selected. Experiments to determine the relationship between DBC and residence time and linear velocity are summarized in FIG. 5 and FIG. 6.

Figure 7:
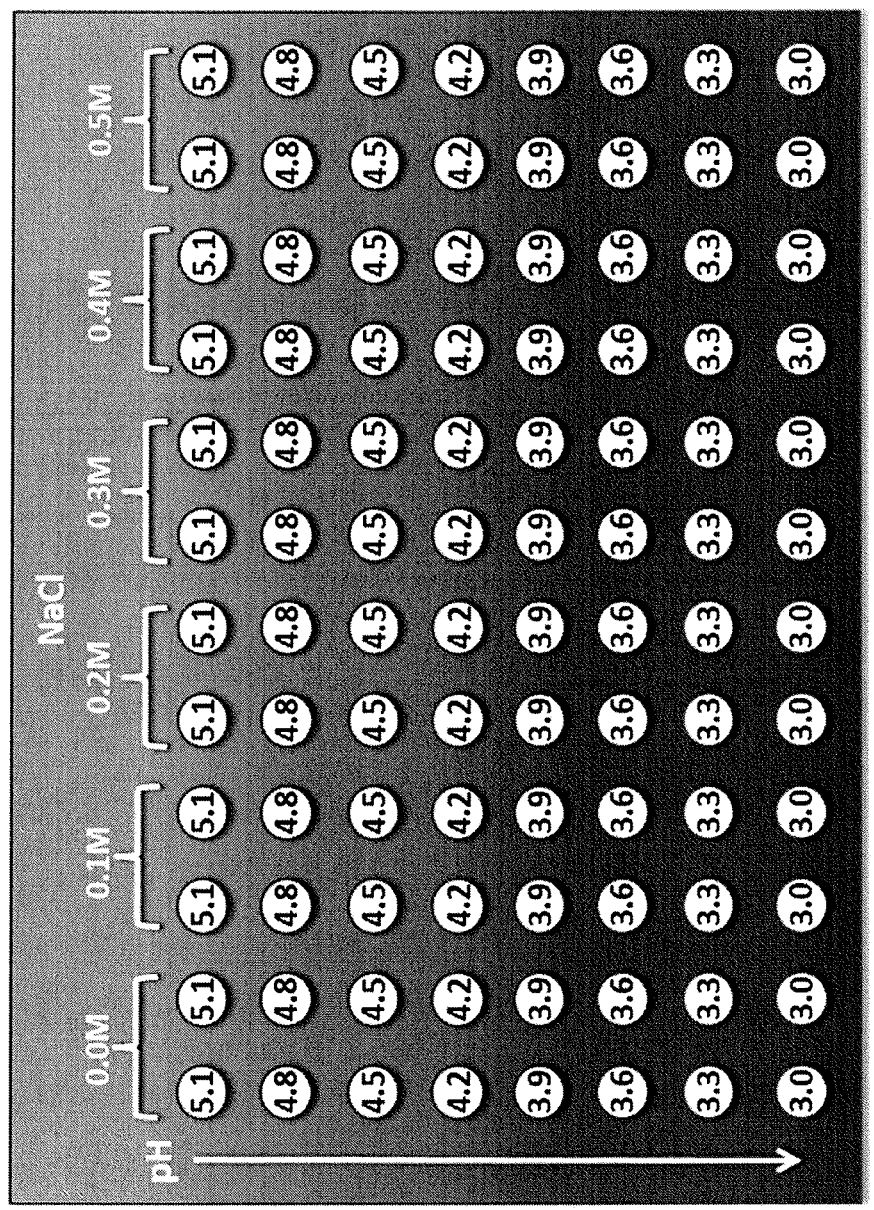
FIG. 7 shows an experimental design for Protein A elution conditions.
Figure 8:
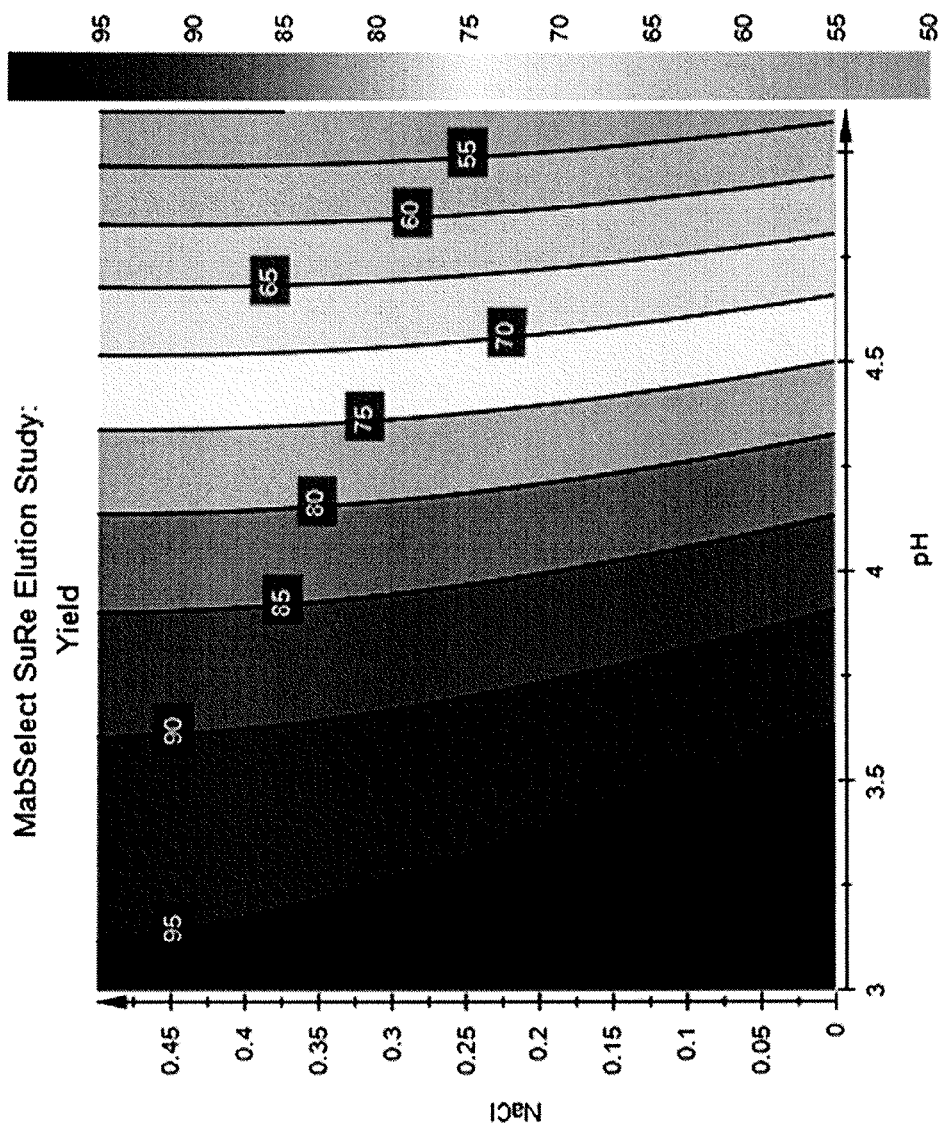
FIG. 8 shows MabSelect SuRe® elution study results.

Statistical design of experiments (DoE) was used to optimize all aspects of the Protein-A capture step. Initially forty-eight different elution conditions were evaluated. The experimental design is summarized in FIG. 7 with the resultant data represented in FIG. 8.

The results indicate that the elution pH range of 3.0 to 3.5 gives a maximum recovery of greater than 95% when the sodium chloride content of the elution matrix is less than 100 mM concentration. Finally, there were no reportable changes in high molecular weight content of the eluate within the pH and sodium chloride ranges tested in this study indicating a robust elution condition. Table 5 outlines the optimized adalimumab capture step. Table 6 summarizes the impurity clearances and product quality achieved using the capture step described above.

TABLE 5

MabSelect SuRe® Capture Step

| Chromatography Step | Parameter | pH Target (Range) | Conductivity Target - mS/cm (Range) |
|---|---|---|---|
| Equilibration | 20 mM sodium phosphate, 50 mM sodium chloride, pH 7.2 | 7.2 (7.0-7.4) | 8.0 (6.0-10.0) |
| Sample Loading | adalimumab (Residence time = 4 min) to a 20-50 g/L binding capacity | NA | NA |
| Wash | 20 mM sodium phosphate, 50 mM sodium chloride, pH 7.2 | 7.2 (7.0-7.4) | 8.0 (6.0-10.0) |
| Elution | 80 mM sodium acetate, pH 3.5 | 3.5 (3.3-3.7) | 0.5 (0.1-1.5) |
| Re-equilibration | 20 mM sodium phosphate, 50 mM sodium chloride, pH 7.2 | 7.2 (7.0-7.4) | 8.0 (6.0-10.0) |

TABLE 6

MabSelect SuRe ® Eluate Impurity Profile

| | | SEC | | | Cation Exchange | | | | | Step |
| | Conc. (g/L) | % HMW | % MON | % LMW | % Acidic | % Main | % Basic | HCP (ppm) | DNA (ppb) | rPA (ppm) | Yield (%) |
|---|---|---|---|---|---|---|---|---|---|---|---|
| Clarified Unprocessed Bulk | 0.56 | 1.0 | 97.0 | 2.0 | 24.9 | 55.0 | 20.1 | $2.3 \times 10^5$ | $2.8 \times 10^6$ | NA | NA |
| MabSelect SuRe Eluate | 21.0 | 1.6 | 98.1 | 0.3 | 25.4 | 55.1 | 19.5 | 663 | 4193 | 0.48 | 97.0 |

Example 2

Virus Inactivation

The potential for the introduction or presence of adventitious viruses exists when mammalian cell lines are employed in the production of monoclonal antibodies. Inactivation of these potential adventitious viruses is routinely addressed by the use of orthogonal steps during the purification process that are either specifically designed for or provide viral inactivation or removal as part of their general use.

The first of such steps in the process is the use of a low pH for an extended period of time to inactivate viruses. Changes in aggregation or high molecular weight species (HMW) that may form as a result of the low pH are monitored. The formation of HMW species should be avoided by the use of chemical agents and other parameters (e.g. agitation, duration, temperature) that promote the monomeric form of the mAb. The pH of the eluate collected from the affinity column following each cycle is lowered by the addition of 1 M citric acid, bringing the pH to 3.5±0.1, and holding the material at room temperature for 60 to 70 minutes. Following the inactivation hold period, the pH is raised to 7.5±0.2 by the addition of 3 M Tris. In the event of precipitation of some residual host cell impurities such as host cell proteins and genomic DNA, the inactivated material was depth-filtered to remove any precipitation, followed by a sterilizing grade 0.22 μm filter. Table 7 shows a summary of chemical agents and parameters for ensuring that the monomeric form of the protein ps well as virus inactivation are maximized.

TABLE 7

Development Parameters Tested for Low pH Virus Inactivation.

| Chemical Agent | pH Range | Temperature Range (° C.) | Agitation |
|---|---|---|---|
| Acetic Acid Citric Acid | 3.0-4.0 | 4-25 | Y/N |

Adalimumab showed no sensitivity specific to either acetic or citric acid relative to a change in percent monomer. During the process of lowering the pH, a significant amount of precipitation occurred and was determined to be a combination of residual host cell proteins as well as residual DNA. Additionally, the pH of the material had no impact on the aggregation state of the material. However, the pH of the material does have an impact on the viral log reduction value (LRV). The higher the pH during the hold period, the lower the LRV for the operation. Therefore, a pH of 3.5 was selected. Due to the relative stability of the monomer at low pH a hold period at ambient temperature (18-25° C.) was used to favor a faster inactivation reaction. Agitation is a parameter that can impact the LRV as well. Investigating a "worst case" included no agitation to simulate poor or no mixing during the hold period. The conditions selected are shown in Table 8 and were tested in duplicate in a viral spiking study performed to assess the LRV. The viral spiking study was performed with time points of 5, 30 and 60 minute low pH hold times. The data from spiking study is shown in Table 9.

TABLE 8

Low pH Hold Parameters

| Step | Solution | Parameter | Target (Range) |
|---|---|---|---|
| pH Decrease | 1M Citric Acid | pH | 3.5 (3.3-3.7) |
| Incubation | NA | Hold Time | 60 min (50-70 min) |
| | NA | Temperature | (18-25° C.) |
| | NA | Agitation | No |
| pH Increase | 3M Tris | pH | 7.5 (7.3-7.7) |

TABLE 9

Viral Spiking Study Results for Low pH Virus Inactivation

| Time Point (min) | LRV (Trial 1) | LRV (Trial 2) |
|---|---|---|
| 5 | >5.1 | >5.3 |
| 30 | >5.1 | >5.3 |
| 60 | >6.8 | >7.0 |

Example 3

Intermediate Purification

Intermediate purification of the adalimumab antibody was accomplished via mixed mode chromatography using CAPTO® Adhere resin as a stationary media. CAPTO® Adhere is a strong anion exchanger with multimodal functionality. The ligand, N-Benzyl-N-methyl ethanol amine exhibits ionic interactions. The most significant of these interactions are hydrogen bonding and hydrophobic interaction. The step was run in flow-through mode and had a dynamic binding capacity of 75-125 g adalimumab/L packed resin while clearing significant amounts of process-related impurities such as leached Protein A, host cell proteins, residual genomic host cell DNA; product variants such as high molecular weight species (antibody dimer and higher order aggregates) and acidic charge variants; as well as potential viruses.

The mixed mode resin was conducted in a flow-through mode whereby the adalimumab material will not interact with the stationary resin while process and product related impurities are retained, to varying degrees, by the resin thereby achieving additional purification. Loading conditions were screened initially to determine the optimal mobile phase conditions to facilitate maximum impurities clearance while achieving an acceptable yield. The base screening conditions are outlined in Table 10.

TABLE 10

Mixed mode loading conditions screening process.

| Chromatography Step | Parameter |
|---|---|
| Equilibration | 20 mM Bis-Tris, pH 8.5 |
| Sample Loading | adalimumab (Residence time = 4 min) |
| Elution | 20 mM Bis-Tris, pH gradient (8.5 to 4.0) |
| CIP | 1N sodium hydroxide, 2M sodium chloride |
| Re-equilibration | 20 mM Bis-Tris, pH 8.5 |

TABLE 11A

Mixed mode chromatography binding condition DoE parameters

| Run # | pH | Cond (mS/cm) |
|---|---|---|
| 1 | 6 | 16 |
| 2 | 6 | 4 |
| 3 | 6 | 30 |
| 4 | 8 | 16 |
| 5 | 8 | 30 |
| 6 | 7 | 4 |
| 7 | 7 | 16 |
| 8 | 7 | 16 |
| 9 | 7 | 30 |
| 10 | 8 | 4 |

Figure 9B:
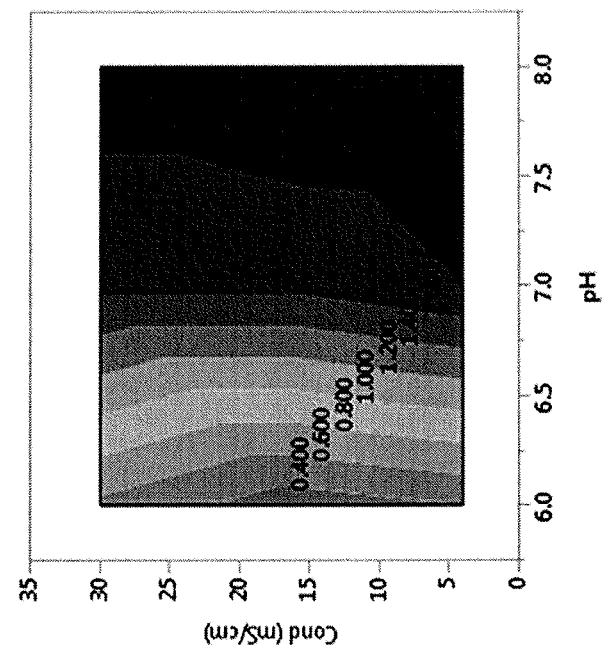
FIG. 9A and FIG. 9B show contour maps showing the effect of pH and conductivity on yield (FIG. 9A) and reduction of high molecular weight (FIG. 9B, shown in % change in HMW %) of CAPTO® Adhere for adalimumab.
Figure 9A:
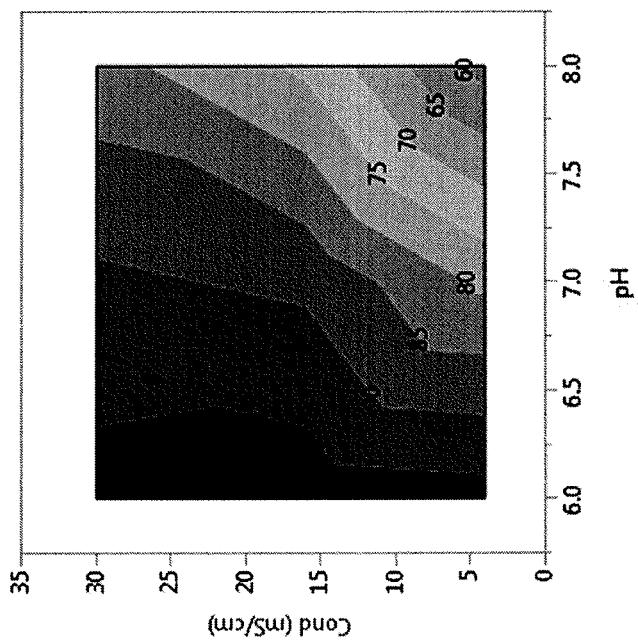
Figure 10B:
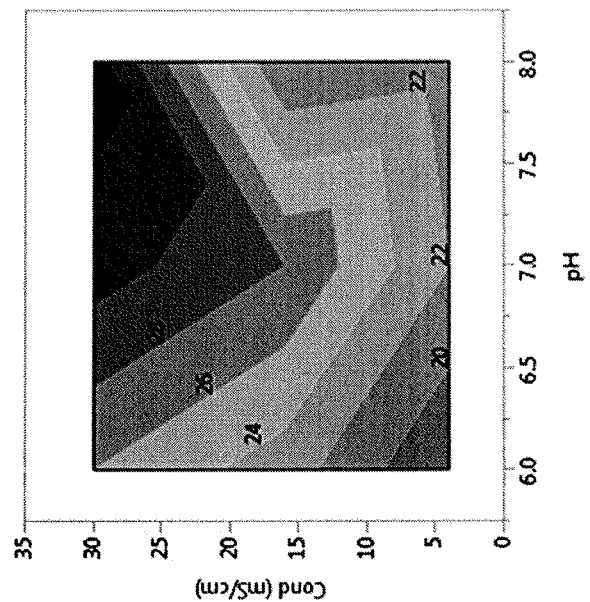
FIG. 10 shows contour maps showing the effect of pH and conductivity on acidic charge variants (A, left panel, shown in % change in acidic variants) and HCP (B, right panel) using CAPTO® Adhere for adalimumab.
Figure 10A:
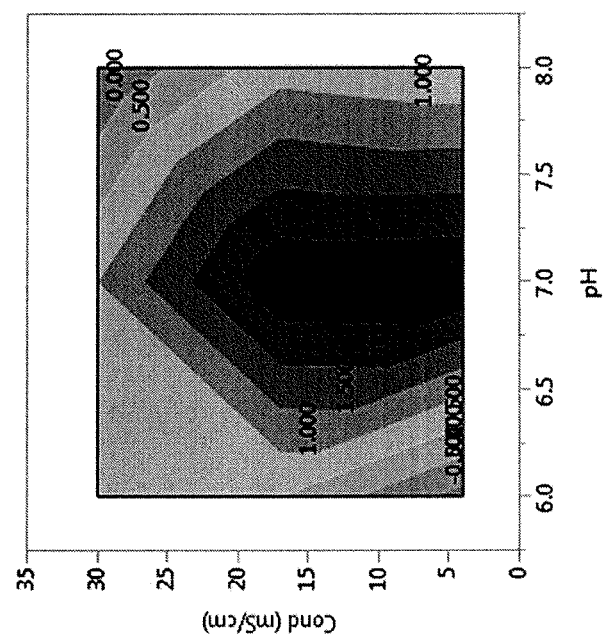

The results of the DoE are shown in Table 11B and FIGS. 9A and 9B. FIG. 9A shows the step yield resulting from relationship between pH and conductivity when adalimumab is loaded as previously described. FIG. 12B shows the reduction of high molecular weight species as a function of pH and conductivity relative to the starting material. FIG. 10 shows a similar contour plots related to both change in acidic charge variants as well as CHO host cell protein clearance. Data from this study also showed that the mixed mode chromatography step is capable of clearing residual host cell DNA to below the level of quantitation of the assay.

TABLE 11B

Effect of pH and Conductivity on adalimumab using CAPTO ® Adhere Chromatography.

| Run | pH | cond | % yield | (%) ACV* | Delta ACV (%) | (%) HMW | Delta HMW (%) | DNA (ppb) | HCP (ppm) |
|---|---|---|---|---|---|---|---|---|---|
| 1 | 8 | 4 | 58 | 25.5 | 0.6 | 0.2 | 2 | <LOQ | 21.2 |
| 2 | 8 | 30 | 97 | 26.6 | −0.5 | 0.3 | 1.9 | <LOQ | 32.5 |
| 3 | 7 | 16 | 89 | 23.9 | 2.2 | 0.6 | 1.6 | <LOQ | 28.6 |
| 4 | 6 | 4 | 97 | 26.8 | −0.7 | 1.8 | 0.4 | <LOQ | 17.6 |
| 5 | 7 | 4 | 79 | 23.4 | 3 | 0.4 | 1.8 | <LOQ | 22 |
| 6 | 8 | 16 | 74 | 25.3 | 0.8 | 0.22 | 1.98 | <LOQ | 20.2 |
| 7 | 7 | 16 | 89 | 22.4 | 3.7 | 0.52 | 1.68 | <LOQ | 26.9 |
| 8 | 6 | 30 | 82 | 25.6 | 0.5 | 1.65 | 0.55 | <LOQ | 25.8 |
| 9 | 6 | 16 | 98 | 25.6 | 0.5 | 1.92 | 0.28 | <LOQ | 23.2 |
| 10 | 7 | 30 | 91 | 25.1 | 1 | 0.55 | 1.65 | <LOQ | 30.7 |

The results of the initial scouting experiment were used to determine the parameters of subsequent DoE. The following DoE (Table 11) was designed to map the operating space and relationship between operating parameters (e.g., pH, conductivity mass loading) and responses (e.g., yield, impurity clearances).

The pH at the UV-280 nm elution peak apex can be used to define the pH minimum in the subsequent design. The pH maximum in the design can then be estimated to be approximately 2 pH units above the minimum. In this case, the pH at the UV apex is 6.3 thus the next series of experiments were set within a pH range of 6.0 to 8.0 (Table 11A). The design of experiments was executed at 100 g adalimumab/L resin.

Figure 11:
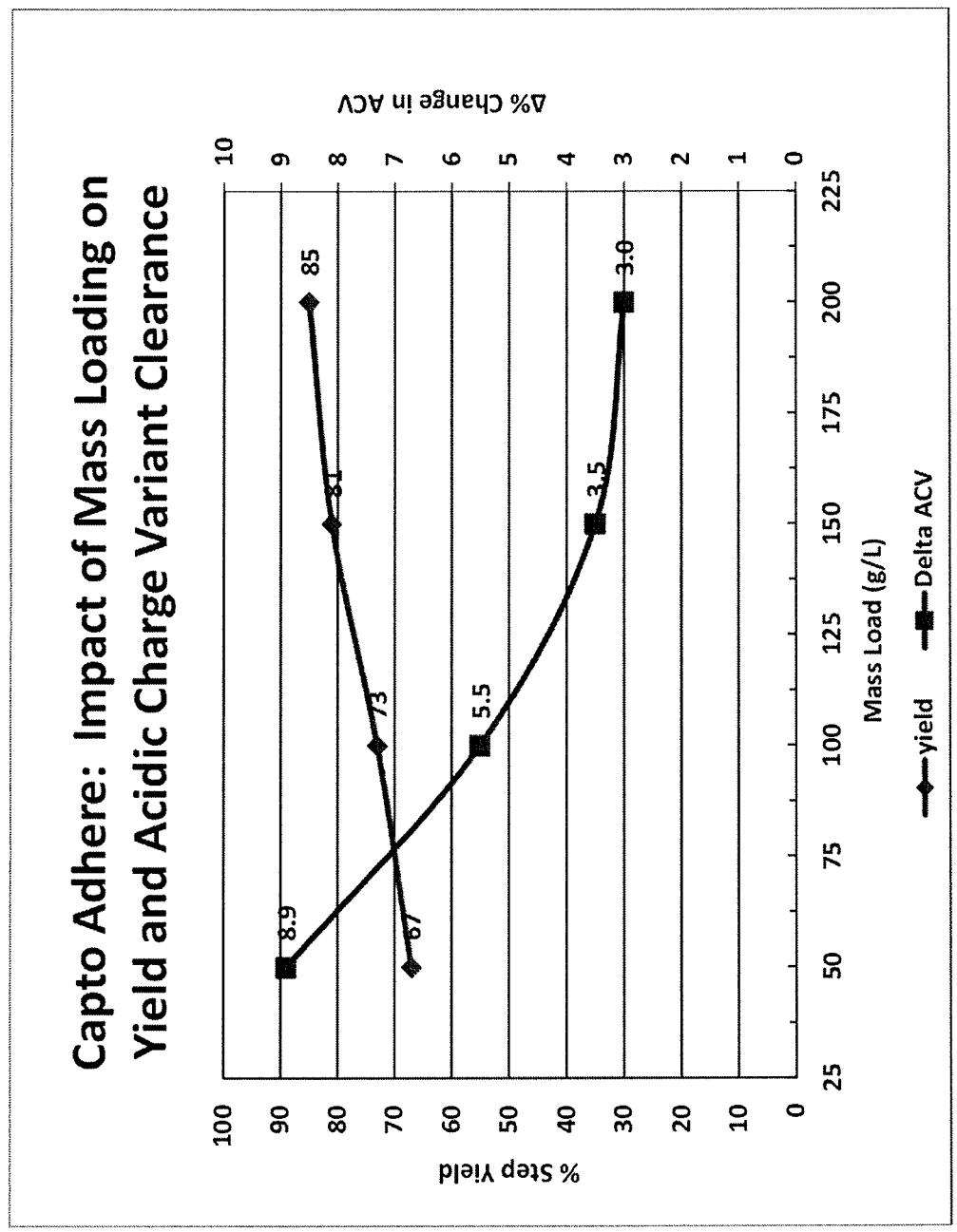
FIG. 11 shows a mixed mode acidic charge variant clearance and yield profile.
Figure 12:
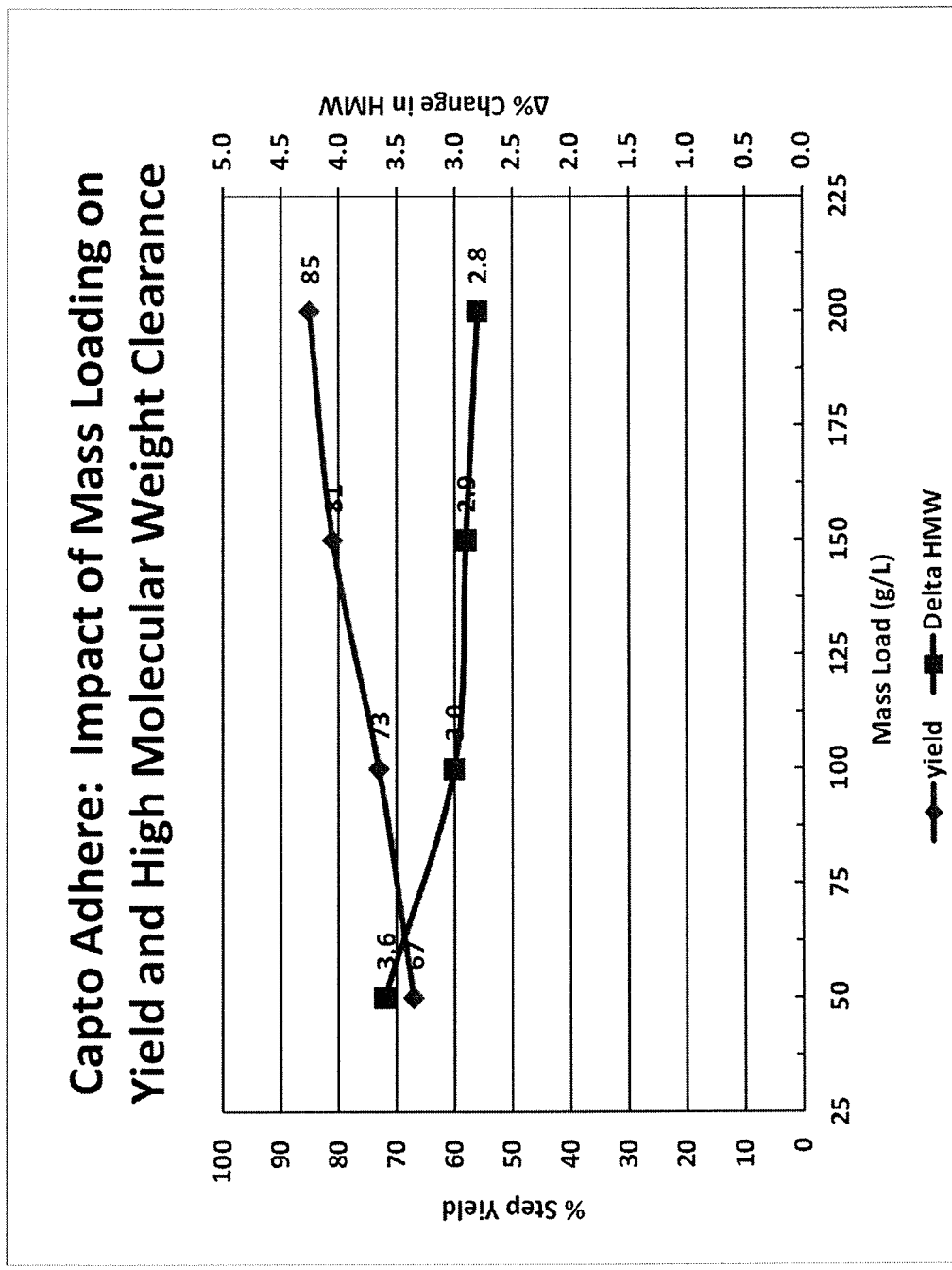
FIG. 12 shows a mixed mode high molecular weight clearance and yield profile.
Figure 13B:
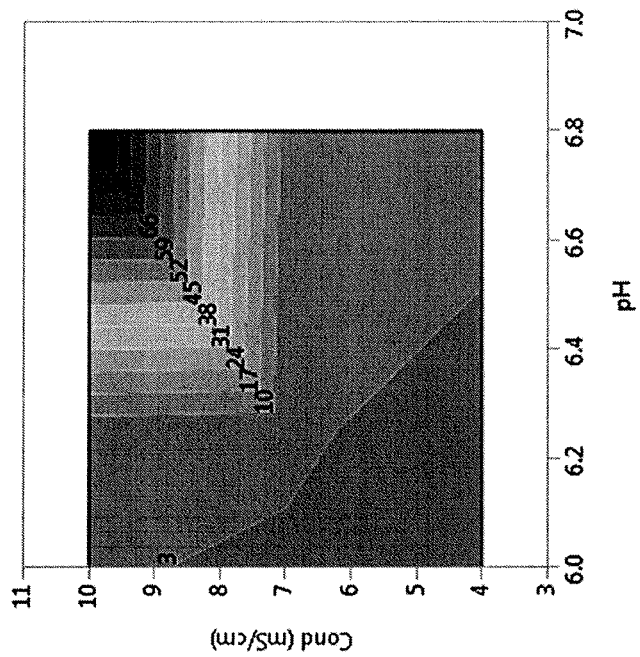
FIG. 13A and FIG. 13B show contour maps showing the effect of Wash 2 pH and conductivity on CAPTO® SP ImpRes eluate yield (FIG. 13A) and reduction of high molecular weight (FIG. 13B, shown in % change in HMW %) for adalimumab.
Figure 13A:
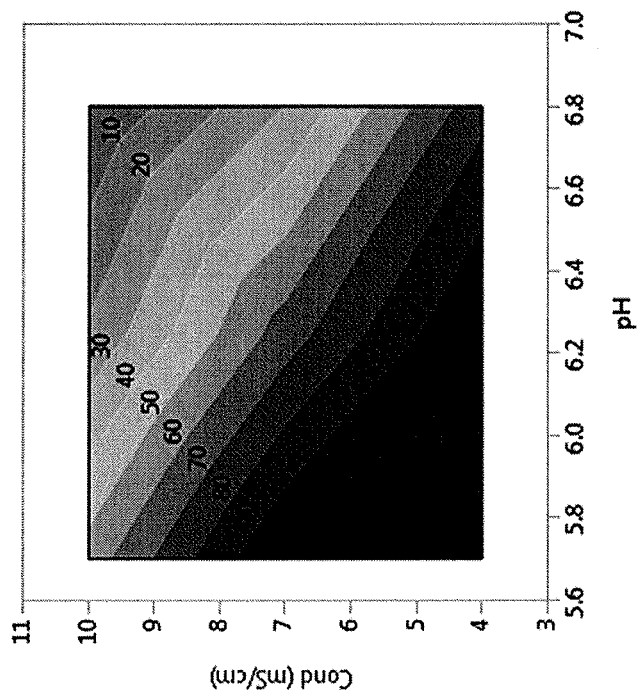

Using the process parameters in Table 12, acidic charge variant and high molecular weight clearance profiles over a range of binding capacities (50-200 $g_{adalimumab}/L_{resin}$) were generated in FIG. 11 and FIG. 12. Yields were also trended in both figures. Recoveries increased from 67-85% with increasing mass loads. In contrast, clearance of acidic species and high molecular weight decreased with increasing binding capacity.

TABLE 12

Mixed mode varying binding capacity process conditions

| Chromatography Step | Parameter |
|---|---|
| Equilibration | 50 mM Bis-Tris, pH 7.5 |
| Sample Loading | adalimumab (Residence time = 2 min) |
| Wash | 50 mM Bis-Tris, pH 7.5 |
| Regeneration | 1M sodium chloride |

TABLE 12-continued

Mixed mode varying binding capacity process conditions

| Chromatography Step | Parameter |
|---|---|
| Re-equilibration | 50 mM Bis-Tris, pH 7.5 |
| CIP | 1N sodium hydroxide |
| Re-equilibration | 50 mM Bis-Tris, pH 7.5 |

An additional study was conducted to determine the effectiveness of several buffer systems of the performance of chromatography step under optimal pH and conductivity. The data are shown in Table 13. Buffer systems including bis-tris, sodium phosphate and HEPES were tested side by side at common pH and conductivities of 7.5 and 8.5 mS/cm respectively. Recovery as well as aggregate and acidic charge variant clearances was of primary interest in the study. The data indicate that while there are only subtle differences (within the variability of the assays used to test) there is an unexpected and significant improvement in recovery of adalimumab when HEPES is employed as the mobile phase.

TABLE 13

Performance of buffer systems used on CAPTO ® Adhere purification of adalimumab.

| | Bis-Tris | Phosphate | HEPES |
|---|---|---|---|
| pH | | 7.5 | |
| Conductivity (mS/cm) | | 8.5 | |
| % Yield | 73 | 74 | 90 |
| ΔACV (%) | −3 | −3.2 | −2.1 |
| ΔHMW (%) | −2.2 | −2.3 | −2.1 |

The development and data described above regarding the intermediate chromatography step maps out a design space that shows the impact pH, conductivity and resin mass loading have on process (yield) and product parameters (HMW, HCP, rDNA and acidic charge species). The contour maps shown above are indicative of a process that is robust and will produce adalimumab with increased purity (Table 14) and can be further polished if necessary. Table 14 shows the preferred mobile phase conditions for the intermediate polishing of adalimumab.

TABLE 15

CAPTO ® Adhere Intermediate Chromatography Step

| Chromatography Step | Current Parameter | pH Target (Range) | Conductivity Target - mS/cm (Range) |
|---|---|---|---|
| Equilibration | 50 mM HEPES | 7.5 (7.3-7.7) | 8.5 (7.5-9.5) |
| Sample Loading | adalimumab (Residence time = 4 min) to a 50-150 g/L binding capacity | NA | NA |
| Wash | 50 mM HEPES | 7.5 (7.3-7.7) | 8.5 (7.5-9.5) |
| Re-equilibration | 50 mM HEPES | 7.5 (7.3-7.7) | 8.5 (7.5-9.5) |

Example 4

Polishing Purification—Acidic Species

The cation exchange chromatography is performed using CAPTO® SP ImpRes resin. This step is primarily for the reduction of acidic charge variants, leached Protein A, host cell proteins and potential viruses. The step is run in bind and elute mode and has a dynamic binding capacity of 25-50 g adalimumab/L packed resin (up to 60 g of binding has been achieved). Cation exchange chromatography is used primarily to reduce the remaining acidic charge species to within range of the reference product (HUMIRA® adalimumab, Abbvie Biotechnology Ltd. Corp.). Additional clearance of process and product related impurities (HMW, HCP, rPA, rDNA) as well as potential viruses can also be achieved during this step.

A series of experiments were performed to determine the most effective processing pH to bind and elute adalimumab. Six runs were conducted using pH values ranging from 7.5-5.0 in 0.5 unit increments with process conditions outlined in Table 16.

TABLE 14

CAPTO ® Adhere Flow-Through Impurity Profile

| | Conc. (g/L) | SEC | | | Cation Exchange | | | HCP (ppm) | DNA (ppb) | rPA (ppm) | Step Yield (%) |
|---|---|---|---|---|---|---|---|---|---|---|---|
| | | % HMW | % MON | % LMW | % Acidic | % Main | % Basic | | | | |
| Clarified Unprocessed Bulk | 0.56 | 1.0 | 97.0 | 2.0 | 24.9 | 55.0 | 20.1 | $2.3 \times 10^5$ | $2.8 \times 10^6$ | NA | NA |
| MabSelect SuRe ® Eluate | 21.0 | 1.6 | 98.1 | 0.3 | 25.4 | 55.1 | 19.5 | 663 | 4193 | 0.48 | 97.0 |
| CAPTO ® Adhere Flow-through | 5.44 | 0.3 | 99.4 | 0.3 | 21.3 | 57.0 | 21.7 | 130 | 3.5 | <0.04 | 74.0 |

TABLE 16

Initial Polishing Chromatography pH Conditions Screening Process

| Chromatography Step | Parameter |
|---|---|
| Equilibration | 10 mM sodium phosphate, pH 7.5/7.0/6.5/6.0/5.5/5.0 |
| Sample Loading | adalimumab (Residence time = 4 min, volume loaded = 5% CV) |
| Wash | 10 mM sodium phosphate, pH 7.5/7.0/6.5/6.0/5.5/5.0 |
| Elution | 10 mM sodium phosphate, conductivity gradient (0-0.5M sodium chloride) |
| Strip | 1M sodium chloride |
| Re-equilibration | 10 mM sodium phosphate, pH 7.5/7.0/6.5/6.0/5.5/5.0 |

As the pH of the processing conditions decrease, adalimumab drifts further from its pI into an increasingly acidic environment. Thus, the protein requires a greater salt content to elute, which causes the resulting shift in eluates as pH decreases. A pH value of 6.2 was determined to be the processing condition best suited to achieve efficient binding and elution of adalimumab.

A follow up experiment was performed using higher phosphate content in the mobile phase to attempt to minimize the pH drift during the salt addition when creating the conductivity gradient necessary for elution of adalimumab. The first run repeated the standard 10 mM sodium phosphate used in the pH screening study, while the second run implemented a stronger phosphate buffer of 25 mM. Processing conditions are in Table 17.

TABLE 17

Polishing Chromatography Mobile Phase Strength Processing Conditions

| Chromatography Step | Parameter |
|---|---|
| Equilibration | 10/25 mM sodium phosphate, pH 6.2 |
| Sample Loading | adalimumab (Residence time = 4 min, binding capacity = 57 g/L resin) |
| Wash | 10/25 mM sodium phosphate, pH 6.2 |
| Elution | 10/25 mM sodium phosphate, conductivity gradient (0-0.5M sodium chloride) |
| Strip | 1M sodium chloride |
| Re-equilibration | 10 mM sodium phosphate, pH 6.2 |

During the conductivity gradient elution, less than a 0.5 pH unit difference was observed when using the stronger phosphate buffer of 25 mM. The greater buffering capacity of the 25 mM sodium phosphate mobile phase was attributed to reducing the pH fluctuation during elution and used moving forward.

The following experiment was designed to evaluate how varying conductivities affect separation of the charge variant species in adalimumab. Protein will be bound and eluted in a stepwise fashion by pumping 1M sodium chloride at increasing increments to achieve salt environments of roughly 20, 40, 60, 80, and 100 mM sodium chloride. Each increment will last for 5 CVs. A final step of 350 mM sodium chloride will be targeted for 10 CVs to elute any remaining protein from the resin. Process parameters are outlined in Table 18.

TABLE 18

Polishing Chromatography Conductivity Step Elution Conditions

| Chromatography Step | Parameter |
|---|---|
| Equilibration | 25 mM sodium phosphate, pH 6.2 |
| Sample Loading | adalimumab (Residence time = 4 min, binding capacity = 57 g/L resin) |
| Wash | 25 mM sodium phosphate, pH 6.2 |
| Elution | 25 mM sodium phosphate, conductivity step elution (20, 40, 60, 80, 100, 350 mM sodium chloride) |
| Strip | 1M sodium chloride |
| Re-equilibration | 25 mM sodium phosphate, pH 6.2 |

Protein begins to elute during the 40 mM sodium chloride step and reaches a peak maximum. Upon its descent, the salt step increased to 60 mM sodium chloride, where we see another peak elute from the column. Two more additional peaks, although slightly smaller in area, elute during the 80 and 100 mM sodium chloride steps. When the final step of 350 mM sodium chloride was executed, the remainder of the protein eluted.

Samples were collected at each step and tested for charge variant species and polydispersity, with results in Table 19. Fractions A3 and A4, corresponding to salt contents of 40 and 60 mM sodium chloride, contained the highest percentage of acidic species (59.2 and 22.8%, respectively). As the salt content increased further, the acidic species consistently decreased to just 0.3% in the final fraction of 350 mM sodium chloride. SEC results showed an opposing trend, with aggregation formation occurring with increasing salt concentrations. The results were successful in demonstrating that the acidic species can be separated by slight increases in conductivity and allow the remaining protein, which is now significantly less rich in acidic character, to be eluted in a higher salt environment.

TABLE 19

Polishing Chromatography Conductivity Step Elution Impurity Profile

| | | Cation Exchange | | | SEC | | |
|---|---|---|---|---|---|---|---|
| | Conc. (g/L) | % Acidic | % Main | % Basic | % HMW | % MON | % LMW |
| Polishing Chromatography Load Material | 1.45 | 22.5 | 56.8 | 20.7 | 0.50 | 96.57 | 2.93 |
| Fraction A3, 40 mM NaCl | 1.82 | 59.2 | 37.1 | 3.8 | 0.14 | 96.59 | 3.27 |
| Fraction A4, 60 mM NaCl | 4.24 | 22.8 | 68.0 | 9.3 | 0.15 | 99.79 | 0.06 |
| Fraction A6, 80 mM NaCl | 2.94 | 12.7 | 70.6 | 16.7 | 0.27 | 99.67 | 0.06 |
| Fraction A7, 100 mM NaCl | 0.89 | 8.2 | 43.3 | 48.5 | 1.68 | 97.75 | 0.58 |
| Fraction A9, 350 mM NaCl | 1.11 | 0.3 | 1.1 | 98.6 | 3.16 | 96.02 | 0.82 |

A number of runs were performed to determine the most effective wash parameters to achieve sufficient acidic species removal while minimizing yield loss over the polishing chromatography step. Salt contents of 44 and 60 mM sodium chloride were tested based on the results of the conductivity step gradient elution study, and the duration of the wash was varied. The yield and acidic charge variant clearance (ΔACV) were calculated and tested for each run. Run conditions are shown in Table 20.

TABLE 20

Polishing Chromatography Varying Salt and Duration of Wash Step

| Chromatography Step | Parameter |
|---|---|
| Equilibration | 25 mM sodium phosphate, pH 6.2 |
| Sample Loading | adalimumab (Residence time = 7-8 min, binding capacity = 30 g/L resin) |
| Wash 1 | 25 mM sodium phosphate, pH 6.2 |
| Wash 2 | 25 mM sodium phosphate 44/60 mM sodium chloride, pH 6.2 |
| Wash 3 | 25 mM sodium phosphate, pH 6.2 |
| Elution | 25 mM sodium phosphate 100/350 mM sodium chloride, pH 6.2 |
| Strip | 1M sodium chloride |
| Re-equilibration | 25 mM sodium phosphate, pH 6.2 |
| CIP | 1N sodium hydroxide |
| Re-equilibration | 25 mM sodium phosphate, pH 6.2 |

Results of the varying salt and wash duration for acidic variant removal are shown in Table 21. High yields were attained using 60 mM sodium chloride for a 1.5 CV duration, but minimal acidic charge variant clearance was achieved. Greater clearance of acidic species was achieved by increasing the wash duration to 2 CVs (5.6-8.0), but the broad range of clearance with just a 0.5 CV increment in wash duration was not desirable to produce a consistent process. Decreasing the salt content to 44 mM sodium chloride allowed the wash to run for a broader duration (3-5 CVs) to achieve a tighter range of acidic clearance comparable to the 60 mM sodium chloride. Employing a wash duration of 3-5 CVs in 44 mM sodium chloride condition consistently cleared 5-7% of the acidic charge variant with yields ranging from approximately 60-70%.

TABLE 21

Polishing Mode Chromatography Varying Salt and Duration of Wash Step Results

| NaCl (mM) | Duration (CVs) | % Yield | % Δ ACV |
|---|---|---|---|
| 44 | 2 | 84 | 2.8 |
| 44 | 3 | 73 | 4.7 |
| 44 | 4 | 63 | 7.0 |
| 44 | 5 | 59 | 7.1 |
| 60 | 1.5 | 87-92 | 0.8-2.6 |
| 60 | 2 | 70-76 | 5.6-8.0 |

To create a more robust wash step, the duration of the wash was altered from a volume to UV based criteria. Rather than running the wash using a CV collection, it is more appropriate to standardize to a UV A280 value for the duration of the wash. This will help reduce variation between runs with regards to the amount of protein loaded. Process conditions are shown in Table 22.

TABLE 22

Polishing Chromatography Varying Salt and Duration of Wash Step

| Chromatography Step | Parameter |
|---|---|
| Equilibration | 25 mM sodium phosphate, pH 6.2 |
| Sample Loading | adalimumab (Residence time = 7-8 min, binding capacity = 30 g/L resin) |
| Wash 1 | 25 mM sodium phosphate, pH 6.2 |
| Wash 2 | 25 mM sodium phosphate 44/60 mM sodium chloride, pH 6.2 |
| Wash 3 | 25 mM sodium phosphate, pH 6.2 |
| Elution | 25 mM sodium phosphate 100/350 mM sodium chloride, pH 6.2 |
| Strip | 1M sodium chloride |
| Re-equilibration | 25 mM sodium phosphate, pH 6.2 |
| CIP | 1N sodium hydroxide |
| Re-equilibration | 25 mM sodium phosphate, pH 6.2 |

For the 44 mM sodium chloride wash 2 utilizing a 4 CV wash duration, adalimumab rich in acidic species began to elute, reached a UV A280 peak maximum of 1297 mAU, and decreased to 1151 mAU upon completing 4 CVs. The UV at which wash 2 concluded was calculated to be approximately 90% of the peak maximum. This value was used moving forward to standardize the end of wash 2 using 44 mM sodium chloride to reduce the acidic charge variant.

The current elution buffer, 25 mM sodium phosphate 350 mM sodium chloride, showed an increase in high molecular weight of the eluate over the polishing step. The high salt environment may be the contributing factor to increased aggregation and is also known to cause pressure issues during the viral filtration step, which occurs after the polishing chromatography in the adalimumab process. A series of experiments were conducted using 350, 150, and 100 mM sodium chloride in the elution buffer with yield and SEC being monitored. Process conditions are in Table 23.

TABLE 23

Polishing Chromatography Varying Salt Elution Buffer Conditions

| Chromatography Step | Parameter |
|---|---|
| Equilibration | 25 mM sodium phosphate, pH 6.2 |
| Sample Loading | adalimumab (Residence time = 7-8 min, binding capacity = 30 g/L resin) |
| Wash 1 | 25 mM sodium phosphate, pH 6.2 |
| Wash 2 | 25 mM sodium phosphate 60 mM sodium chloride, pH 6.2 |
| Wash 3 | 25 mM sodium phosphate, pH 6.2 |
| Elution | 25 mM sodium phosphate 350/150/100 mM sodium chloride, pH 6.2 |
| Strip | 1M sodium chloride |
| Re-equilibration | 25 mM sodium phosphate, pH 6.2 |
| CIP | 1N sodium hydroxide |
| Re-equilibration | 25 mM sodium phosphate, pH 6.2 |

Results from varying salt content in the elution buffer are in Table 24. As the molarity of salt decreases, aggregate was reduced. At the lowest salt condition tested, no high molecular weight was created over the polishing step.

TABLE 24

Polishing Chromatography Varying Salt Content of Elution Buffer Results

| Salt Elution Condition (mM) | Sample | Conc. (g/L) | % Yield | SEC % HMW | % MON | % LMW |
|---|---|---|---|---|---|---|
| 350 | Load Material | 1.91 | N/A | 0.46 | 96.76 | 2.78 |
|  | Eluate | 12.6 | 75 | 1.05 | 98.85 | 0.10 |
| 150 | Load Material | 1.06 | N/A | 0.09 | 94.02 | 5.89 |
|  | Eluate | 10.38 | 84 | 0.25 | 99.74 | 0.01 |
| 100 | Load Material | 1.07 | N/A | 0.13 | 97.24 | 2.63 |
|  | Eluate | 6.78 | 92 | 0.11 | 99.89 | 0.00 |

Wash 2 was designed to remove a significant portion of the acidic species inherent to adalimumab. Because of this, yields over this step range from just 60-70%. A DoE was designed over a range of pH and conductivities in attempt to minimize protein loss while retaining the high reduction of acidic variant. The ranges were attained by conducting two gradient elution runs, the first of which eluted adalimumab via a pH gradient, the second using conductivity. Using offline pH and conductivity meters to verify, the UV A280 peak max of the eluate occurred at a pH of 7.5 and conductivity of 13 mS/cm, respectively. From these results, the corresponding pH and conductivity ranges for the DoE are outlined in Table 25.

TABLE 25

Polishing mode chromatography wash 2 condition DoE parameters and Data

| Run # | PH | Cond (mS/cm) | Yield (%) | ΔHMW | ΔACV |
|---|---|---|---|---|---|
| 1 | 6.8 | 10 | 0.0 | 0.0 | 100 |
| 2 | 6.8 | 7 | 30.1 | 0.16 | 7.3 |
| 3 | 6.8 | 4 | 76.9 | 0.0 | 6.3 |
| 4 | 5.7 | 4 | 100.0 | 0.28 | 0.0 |
| 5 | 6.2 | 7 | 64.1 | 0.22 | 4.7 |
| 6 | 6.2 | 7 | 65.9 | 0.17 | 3.4 |
| 7 | 5.7 | 7 | 100.0 | 0.09 | 0.0 |
| 8 | 5.7 | 10 | 54.9 | 0.19 | 4.2 |
| 9 | 6.2 | 10 | 21.4 | 0.44 | 5.4 |
| 10 | 6.2 | 4 | 100.0 | 0.16 | 0.0 |

The DoE described above was designed to elucidate a set of robust parameters that a cation exchange chromatography step can be operated to provide maximum yield while reducing product and process related impurities. The product quality attributes monitored most closely during this step are the charge heterogeneity profile and high molecular weight species. Modulation of the pH and conductivity conditions in the second washing step is important for reducing the amount of acidic charge species in the monoclonal antibody material.

As with most chromatography conditions, a balance must be found between the required amount of impurity reduction and material recovery (yield) for the operation. This step has been designed to separate species of adalimumab with only very subtle changes in charge (acidic species) from the main species population. Table 25 shows the yield, high molecular weight, and acidic charge clearance data that have been generated. It is evident that even small variations in pH (5.0-6.8) and conductivity (4-10 mS/cm) may have a large impact on yield ranging from 21 to 100% while the reduction of high molecular weight is more subtle (0.0 to 0.45%). Charge heterogeneity data indicate that within this range of pH and conductivity the acidic charge species can be modulated greatly. Practically, the acidic charge variants can be reduce from as little as 3% to as much as 8%. The impact of mass loading on the resin also plays a role in the level of reduction that can be seen. Mass loading ranges tested included 30 to 60 g/L and showed a range of acidic charge variant reduction from 1% to 11%

The development and data described above regarding the polishing chromatography step maps out a design space that shows the impact pH and conductivity have on process (yield) and product parameters (acidic species and HMW). Table 26 shows the preferred mobile phase conditions for the polishing chromatography of adalimumab. The contour maps shown above are indicative of a process that is robust and will produce adalimumab with the required purity (Table 27).

TABLE 26

CAPTO ® SP ImpRes Polishing Chromatography Step

| Chromatography Step | Parameter | pH Target (Range) | Conductivity Target-mS/cm (Range) |
|---|---|---|---|
| Equilibration | 25 mM sodium phosphate | 6.2 (6.0-6.4) | 2.3 (1.0-3.6) |
| Sample Loading | adalimumab (Residence time = 8 min) to a 30-50 g/L binding capacity | NA | NA |
| Wash 1 | 25 mM sodium phosphate | 6.2 (6.0-6.4) | 2.3 (1.0-3.6) |
| Wash 2 | 25 mM sodium phosphate 44 mM sodium chloride | 6.2 (6.0-6.4) | 7.1 (6.6-7.6) |
| Wash 3 | 25 mM sodium phosphate | 6.2 (6.0-6.4) | 2.3 (1.0-3.6) |
| Elution | 25 mM sodium phosphate 100 mM sodium chloride | 6.2 (6.0-6.4) | 12.8 (10.0-14.0) |
| Re-equilibration | 25 mM sodium phosphate | 6.2 (6.0-6.4) | 2.3 (1.0-3.6) |

TABLE 27

CAPTO ® SP ImpRes Eluate Impurity Profile

| | Conc. (g/L) | SEC | | | Cation Exchange | | | HCP (ppm) | DNA (ppb) | rPA (ppm) |
| | | % HMW | % MON | % LMW | % Acidic | % Main | % Basic | | | |
|---|---|---|---|---|---|---|---|---|---|---|
| Clarified Unprocessed Bulk | 0.56 | 1.0 | 97.0 | 2.0 | 24.9 | 55.0 | 20.1 | $2.3 \times 10^5$ | $2.8 \times 10^6$ | NA |
| MABSELECT SURE ® Eluate | 21.0 | 1.6 | 98.1 | 0.3 | 25.4 | 55.1 | 19.5 | 663 | 4193 | 0.48 |
| CAPTO ® Adhere Flow-through | 5.44 | 0.3 | 99.4 | 0.3 | 21.3 | 57.0 | 21.7 | 130 | 3.5 | <0.04 |
| CAPTO ® SP ImpRes Eluate | 10.7 | 0.4 | 99.6 | 0.0 | 14.2 | 61.3 | 24.5 | <1.1 | <0.9 | <0.02 |

Example 5

Nanofiltration

Nanofiltration is a requirement in the production of small and large proteins when using mammalian cell culture. Evaluation of the nanofiltration process was conducted varying protein concentrations as well concentrations of sodium chloride and their impact on flux and capacity. The results are shown in Table 28.

TABLE 28

Nanofiltration Parameters

| Pore Size (nm) | Protein Concentration (g/L) | NaCl Concentration (mM) | Flux (LMH) | Flow Decay (%) | Throughput (L/m$^2$) |
|---|---|---|---|---|---|
| 15 | 12.0 | 350 | 10 | 74 | 1 |
|    | 4    | 0.0 | 36 | 3  | 218 |
|    | 4    | 350 | 28 | 57 | 116 |
| 20 | 12.0 | 350 | 38 | 38 | 153 |
|    | 4    | 0.0 | 61 | 21 | 208 |
|    | 4    | 350 | 60 | 12 | 202 |

The conditions selected are shown below in Table 29 and were tested in duplicate in a viral spiking study performed by a third party vendor to assess the LRV. The viral spiking study was performed with replicates of two model viruses. The data from the spiking study is shown in Table 30.

TABLE 29

Final adalimumab Nanofiltration Parameters

| Parameter | Target (Range) |
|---|---|
| Protein Concentration (g/L) | 8.0 (2-12) |
| Ionic Strength (mM) | 100 (0-250) |
| Flux (LMH) | 42 (35.0-60.0) |
| Capacity (g/m$^2$) | ≤5500 |

TABLE 30

Viral Spiking Study Results for adalimumab Nanofiltration

| Virus Type | LRV (Trial 1) | LRV (Trial 2) |
|---|---|---|
| Small, Non-enveloped | 4.9 | 5.6 |
| Retrovirus | >6.0 | >6.0 |

Example 6

Concentration and Diafiltration

The final step in the purification or downstream manufacturing process is the ultrafiltration or concentration and diafiltration of the product pool. This unit operation brings the product to its specified protein concentration during the ultrafiltration portion and buffer exchanged into the formulation vehicle that provides maximum product stability.

Figure 14:
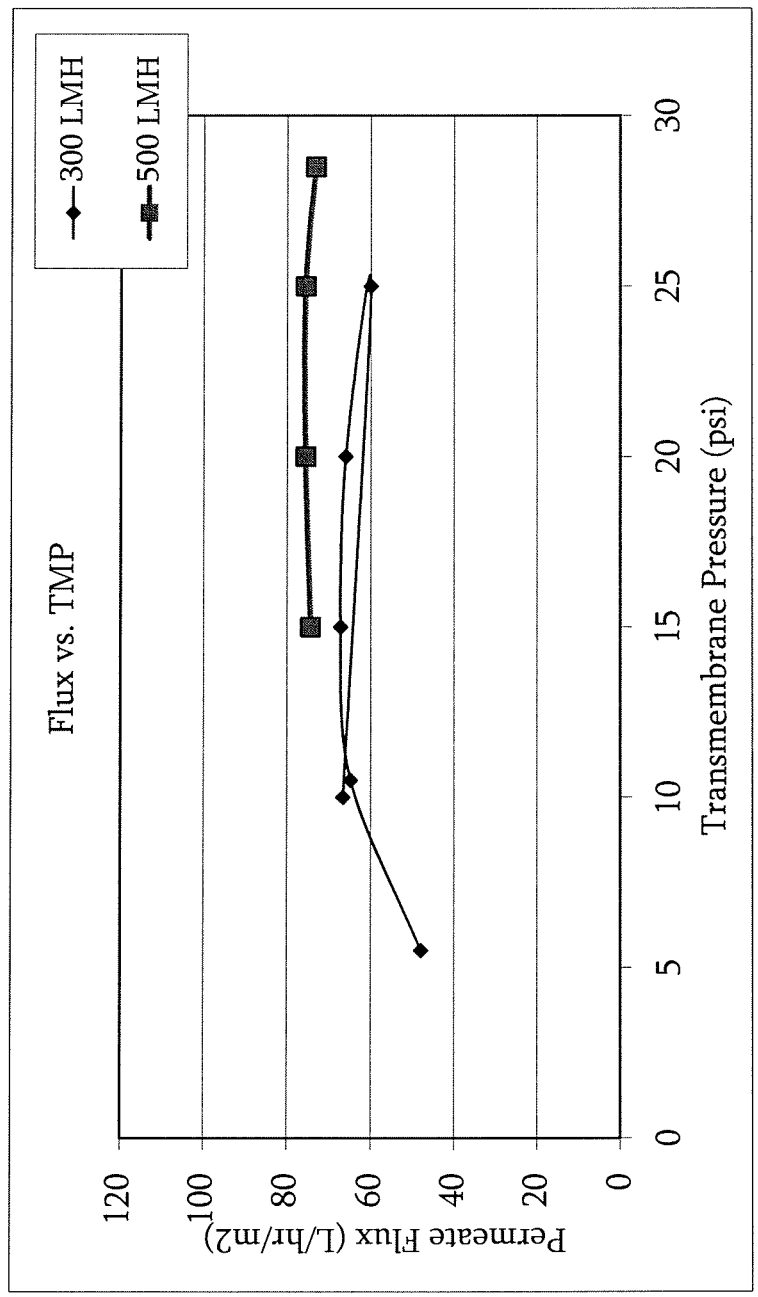
FIG. 14 shows flux vs. TMP at initial adalimumab concentration (10 g/L).
Figure 15:
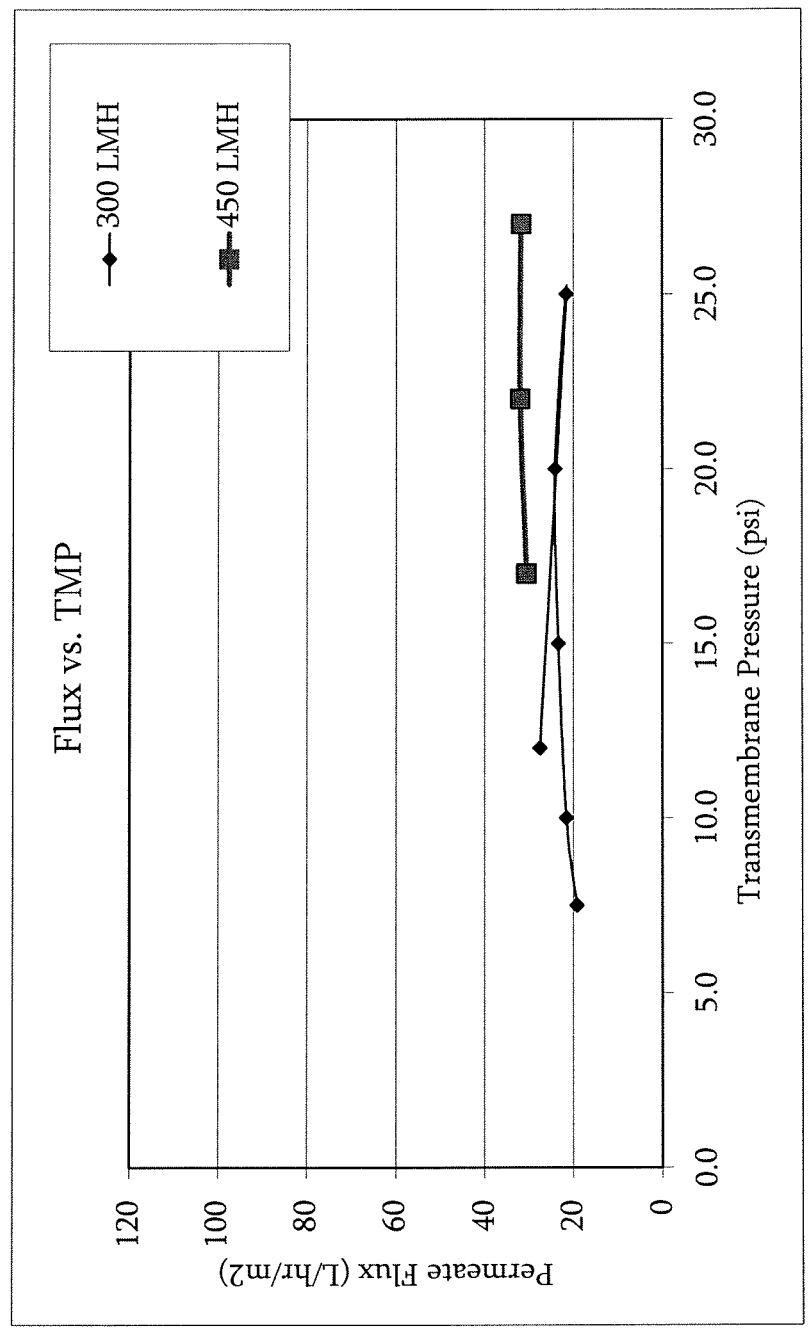
FIG. 15 shows flux vs. TMP at final adalimumab concentration (65 g/L).
Figure 16:
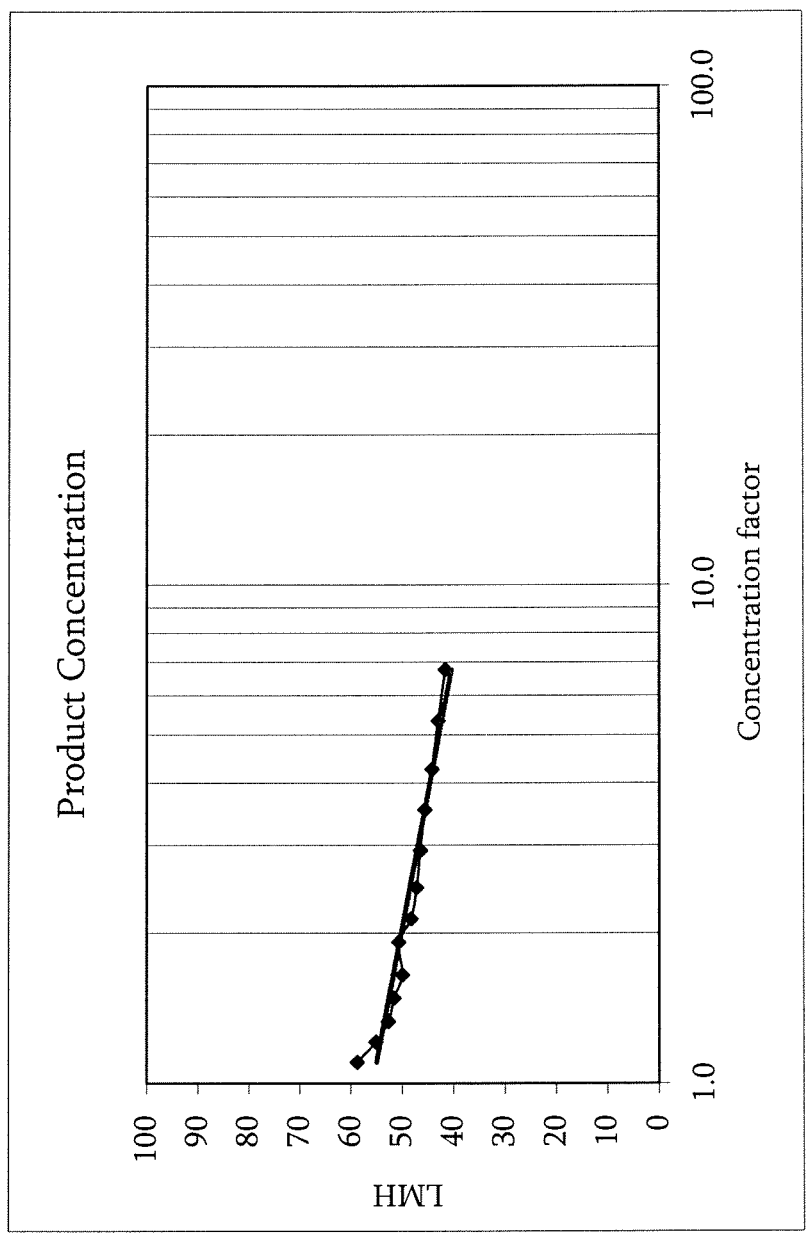
FIG. 16 shows concentration factor vs. flux of adalimumab during concentration.
Figure 17:
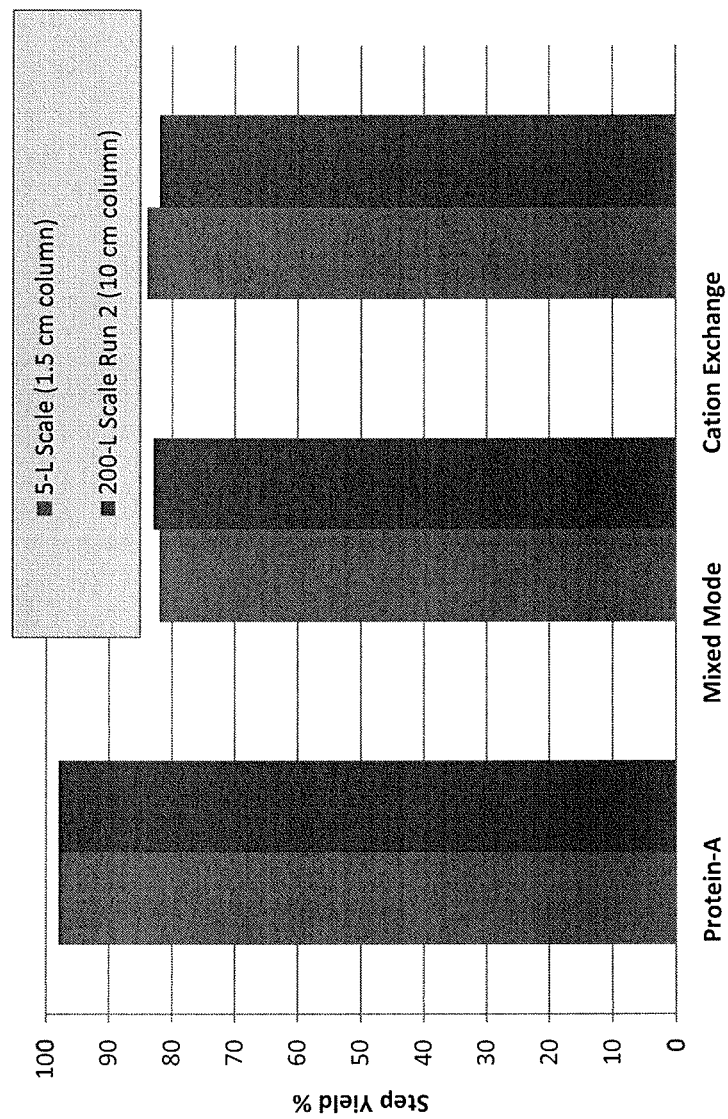
FIG. 17 shows a scalable purification process (5 L-200 L scale) for adalimumab.
Figure 18:
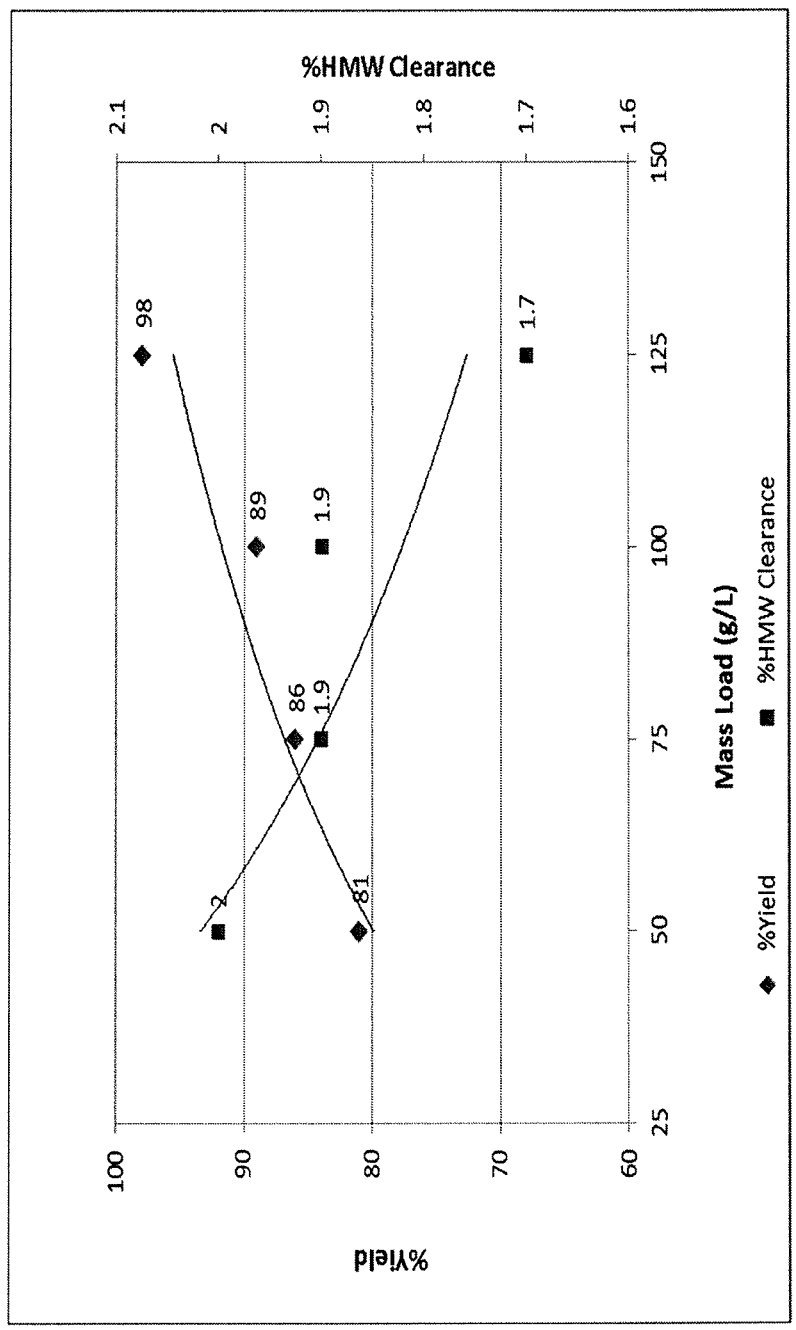
FIG. 18 shows the impact of mass load on yield and HMW using HEPES.
Figure 19:
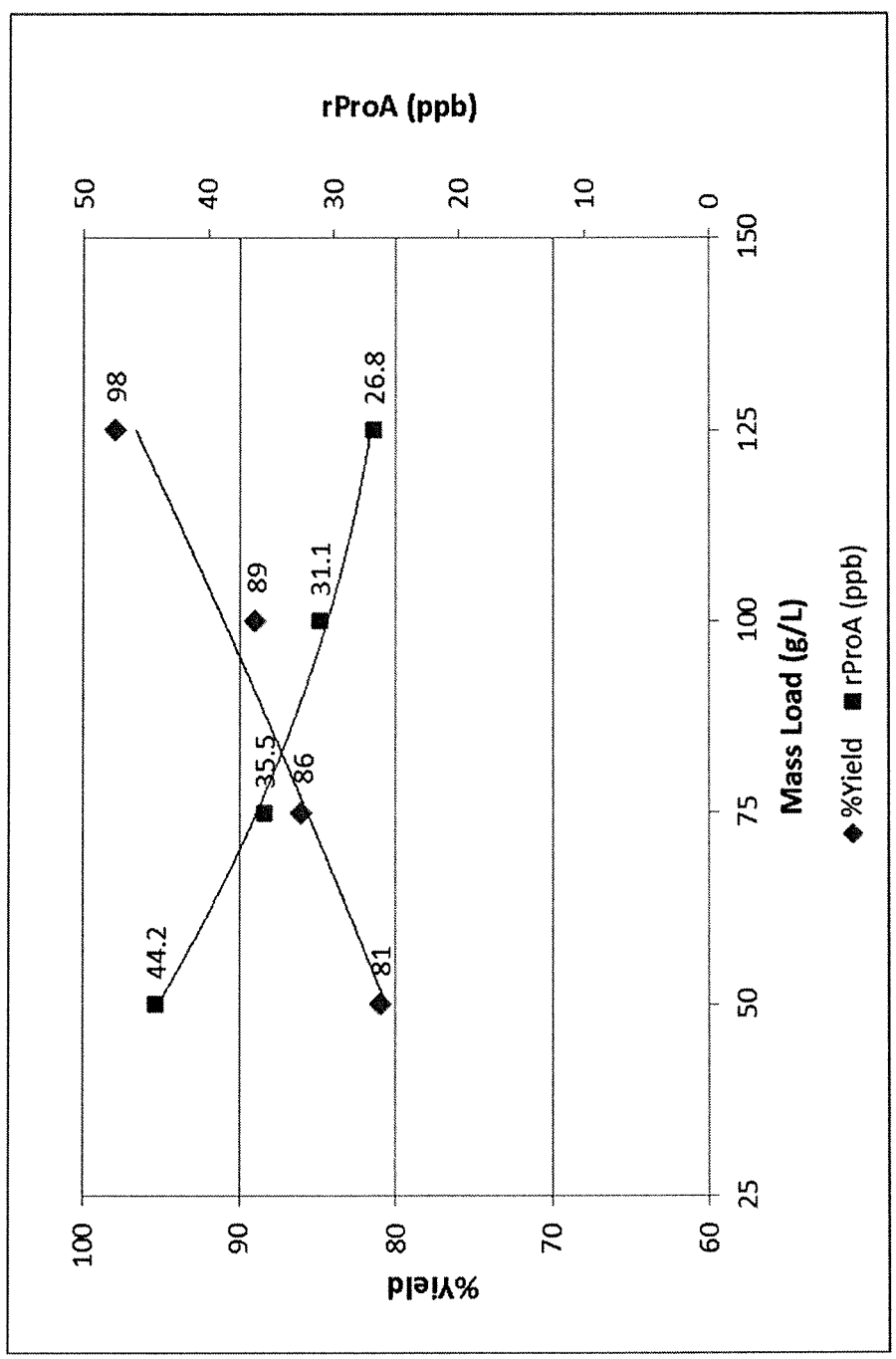
FIG. 19 shows the impact of mass load on residual Protein A clearance using HEPES.
Figure 20:
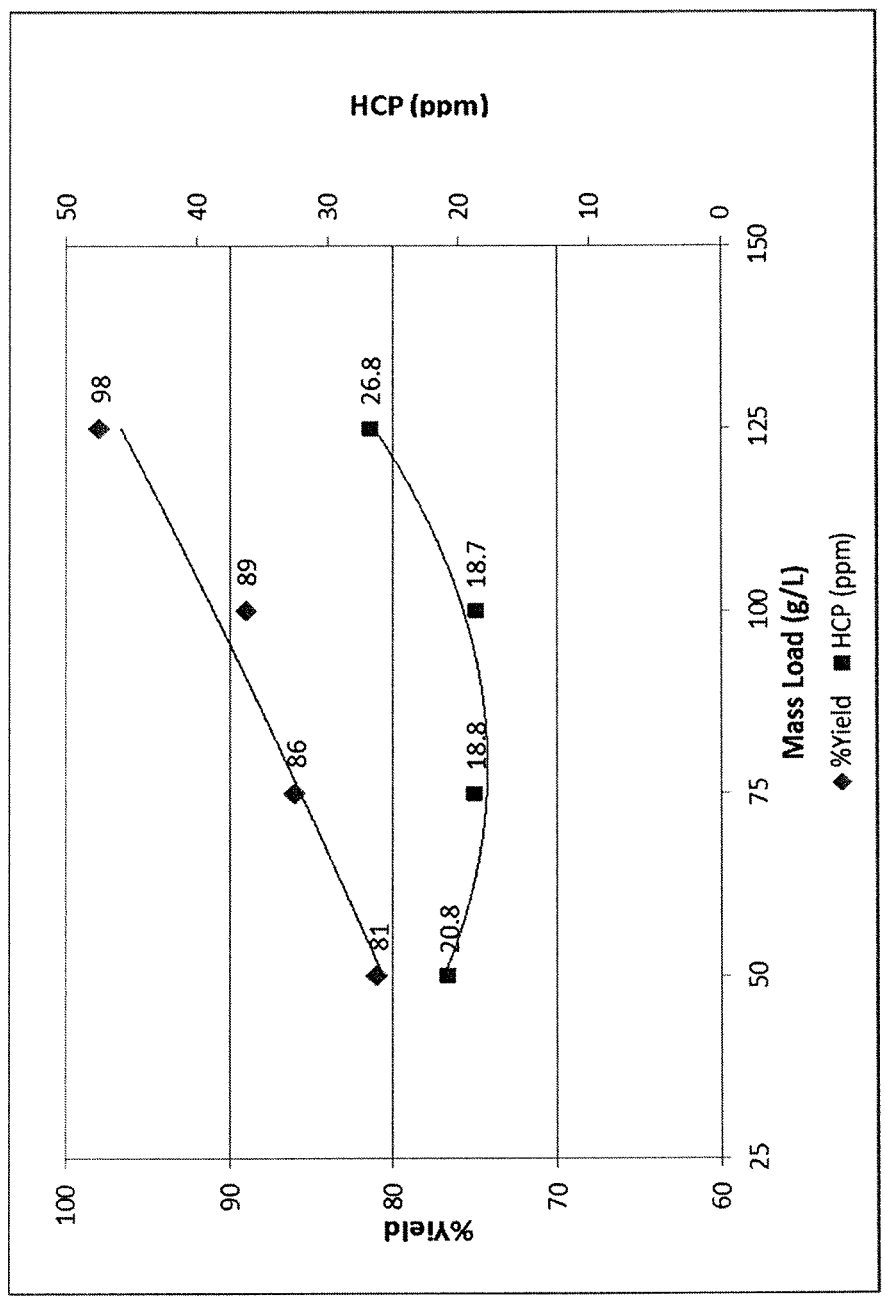
FIG. 20 shows the impact of mass load on HCP clearance using HEPES.
Figure 21:
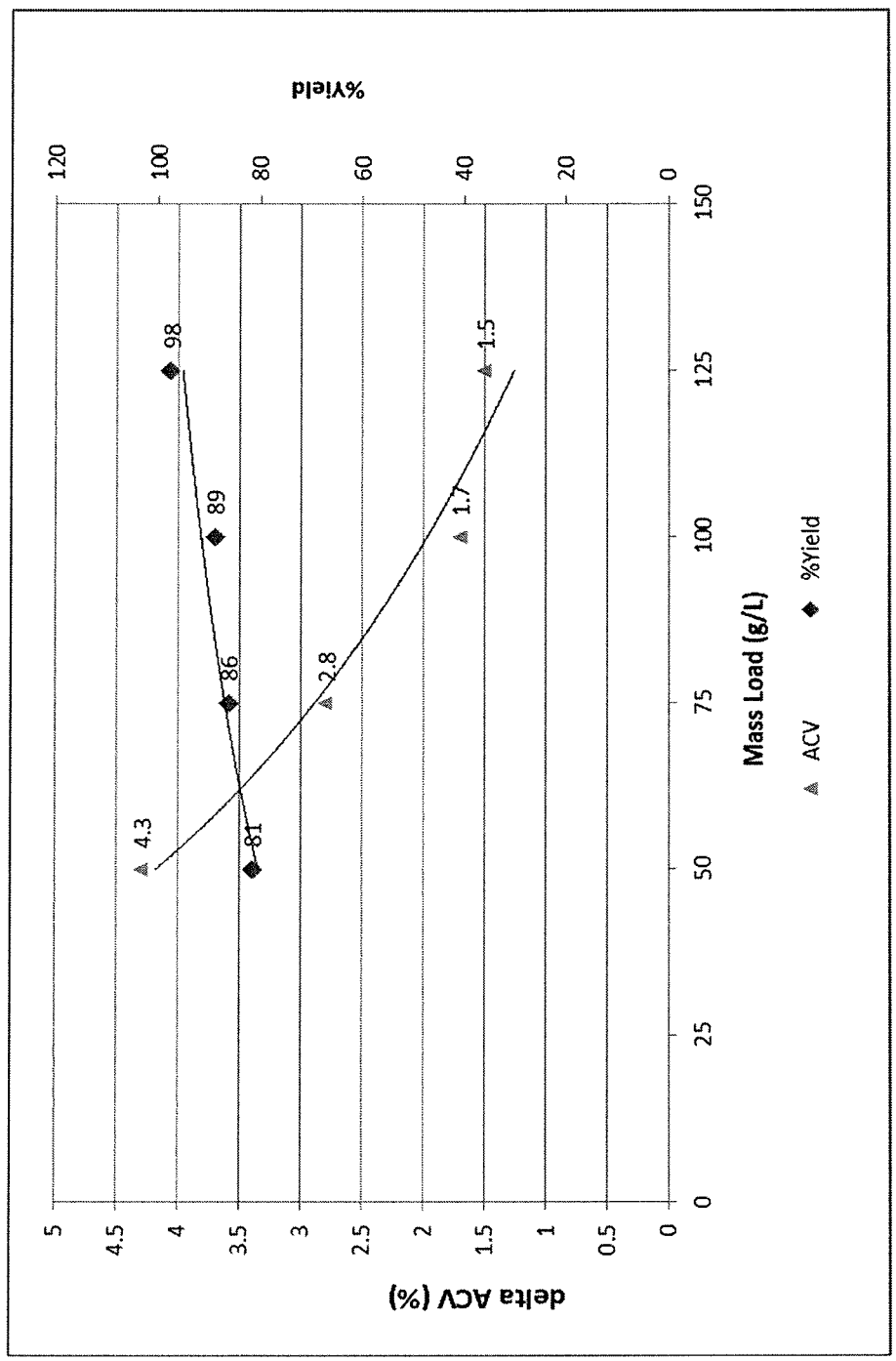
FIG. 21 shows the impact of mass load on acidic charge variant clearance using HEPES.

A polyethersulfone cassette with a 30 kDa molecular weight cutoff was evaluated for its performance with respect to the impact of TMP on permeate flux and product retention during ultrafiltration (UF) as well as performance on buffer exchange and contaminant removal during diafiltration. Ultrafiltration experiments were conducted bracketing a range of 10-65 g/L including process flux versus both transmembrane pressure (TMP) and time (FIGS. 14 and 15). Feed flow was tested from 300-500 L/m2/hr during UF experiments at both the initial product concentration (10 g/L) as well as the final concentration (60 g/L). TMP was evaluated with respect to time and process flux in the range of 2-30 psi. It was concluded that the optimum conditions to operate the UF portion of the step were with a feed flow rate of 450 L/m2/hr and a TMP of 10 psi. The membrane was challenged to a ratio of 500 g of adalimumab/m2 of filter area (FIG. 16).

Diafiltration (DF) of adalimumab was evaluated by examining pH and conductivity changes in the permeate effluent over a range of diavolumes exchanges (0-10 diavolumes) as well as changes in process flux over time. The initial pH and conductivity of the DF starting material were 6.2 and 12.9 mS/cm respectively while the target pH and conductivity of the formulation vehicle was 5.2 and 4.0 mS/cm. Following only four diavolume exchanges the pH and conductivity of the material were 3.99 and 4.0 mS/cm. Process impurity levels such as Chinese Hamster Ovary host cell proteins, residual DNA and residual leached Protein A levels were also evaluated for additional clearance. Only residual DNA levels were reduced beyond initial levels. While the diafiltration is essentially complete following four diavolumes exchanges, the process may utilize five diavolumes to ensure complete diafiltration of adalimumab. Table 31 represents the impurity profile resulting from the complete adalimumab downstream process (the bulk drug substance).

TABLE 31

Bulk Drug Substance Impurity Profile

| | Conc. (g/L) | SEC | | | Cation Exchange | | | HCP (ppm) | DNA (ppb) | rPA (ppm) | Step Yield (%) |
| | | % HMW | % MON | % LMW | % Acidic | % Main | % Basic | | | | |
|---|---|---|---|---|---|---|---|---|---|---|---|
| Clarified Unprocessed Bulk | 0.56 | 1.0 | 97.0 | 2.0 | 24.9 | 55.0 | 20.1 | 2.3 × 10$^5$ | 2.8 × 10$^6$ | NA | NA |
| MABSELECT SURE ® Eluate | 21.0 | 1.6 | 98.1 | 0.3 | 25.4 | 55.1 | 19.5 | 663 | 4193 | 0.48 | 97.0 |
| CAPTO Adhere Flow-through | 5.44 | 0.3 | 99.4 | 0.3 | 21.3 | 57.0 | 21.7 | 130 | 3.5 | <0.04 | 74.0 |

TABLE 31-continued

| | Bulk Drug Substance Impurity Profile | | | | | | | | | |
|---|---|---|---|---|---|---|---|---|---|---|
| | | SEC | | | Cation Exchange | | | | | Step |
| | Conc. (g/L) | % HMW | % MON | % LMW | % Acidic | % Main | % Basic | HCP (ppm) | DNA (ppb) | rPA (ppm) | Yield (%) |
| CAPTO SP ImpRes Eluate | 10.7 | 0.4 | 99.6 | 0.0 | 14.2 | 61.3 | 24.5 | <1.1 | <0.9 | <0.02 | 70.0 |
| Bulk Drug Substance | 50.0 | 0.4 | 99.6 | 0.0 | 14.3 | 59.7 | 26.0 | 1.0 | <0.9 | <0.02 | 98.0 |

Example 7

Summary

Results to date are indicative of a purification process that is robust and capable of reducing even the most subtle product related impurities (acidic species) resulting in adalimumab bulk drug substance that is highly similar to the HUMIRA® (Abbvie Biotechnology Ltd. Corp.) adalimumab reference product.

Example 8

Polishing Purification—Basic Species

The cation exchange chromatography in this Example is performed using a resin with a sulfonate or sulfopropyl chemistry. A series of experiments were performed to determine the most effective pH and conductivity to bind and elute adalimumab. The initial screening process is outlined in Table 32. The step as outlined and described here is primarily for the reduction of basic charge variants, leached Protein A, host cell proteins and potential viruses. The step is run in a bind and elute mode, and has a dynamic binding capacity of 30-70 g antibody per liter of packed resin. Cation exchange chromatography is used primarily to reduce the remaining basic charge species to within range of the reference product (HUMIRA® adalimumab). Additional clearance of process and product related impurities (HMW, HCP, rPA, rDNA) as well as potential viruses can also be achieved during this step.

TABLE 32

Initial cation exchange chromatography pH conditions screening process

| Chromatography Step | Parameter |
|---|---|
| Equilibration | 40 mM sodium phosphate, pH 5.8 |
| Sample Loading | adalimumab (Residence time = 2.5 min) |
| Wash | 40 mM sodium phosphate, pH 6.5 |
| Elution | 40 mM sodium phosphate, conductivity gradient (0.025-0.5M sodium chloride), pH 5.8 |
| Strip | 1M sodium chloride |
| Re-equilibration | 40 mM sodium phosphate, pH 5.8 |

Material was loaded at an acidic pH of 5.0. The pH was gradually increased in increments of 0.5 units and the elution profile was monitored at each point. Binding of adalimumab to the cation exchange support was disrupted at pH 7.0. The conductivity inherent to the mobile phase at pH 7.0 is 4.7 mS/cm. No clear separation of monoclonal antibody species is evident when only the pH is changed.

Additional experiments were conducted to modify the conductivity of the mobile phase to increase the resolution of the chromatography step. An initial experiment conducted at a pH of 5.5 to promote strong affinity and binding was carried out using a conductivity range of 90-150 mS/cm in three chromatography runs. The chromatograms indicate no improvement in resolution as result of the conductivity changes alone. This is due most likely to the charge interaction of the monoclonal antibody to the resin being too strong.

A follow up experiment was run at a pH of 6.5 and at the same conductivities as previously tested. At 90 mM sodium chloride, a shoulder on the descending slope of the UV absorbance profile emerged. This new shoulder is evidence of a separation of charged species in an early stage of resolution.

In order to continue improving the resolution of the chromatography, further optimization of the pH of the binding buffer is required. Reduction of the ionic strength of the buffer from 40 mM to 25 mM as well as a small increase in the pH (6.5 to 6.8) to reduce the affinity of the different charge species of the antibody slightly was attempted. A significant improvement in the resolution of the separation was observed, where a second peak was evident.

This set of experiments outlines a chromatography step using cation exchange chromatography that allows separation of basic charge variants from the predominant charged form of the adalimumab monoclonal antibody. Processing conditions are in Table 33 below. Table 34 shows the stepwise clearance that is achieved through the downstream process.

TABLE 33

Cation exchange chromatography mobile phase strength processing conditions

| Chromatography Step | Parameter |
|---|---|
| Equilibration | 25 mM sodium phosphate, 25 mM sodium chloride, pH 6.8 |
| Sample Loading | adalimumab (Residence time = 2.5 min) |
| Wash | 25 mM sodium phosphate, 25 mM sodium chloride, pH 6.8 |
| Elution | 25 mM sodium phosphate, conductivity gradient (0-0.5M sodium chloride), pH 6.8 |
| Strip | 1M sodium chloride |
| Re-equilibration | 25 mM sodium phosphate, 25 mM sodium chloride, pH 6.8 |

TABLE 34

Cation exchange eluate impurity profile

|  | Conc. (g/L) | SEC | | | Cation Exchange | | | HCP (ppm) | DNA (ppb) | rPA (ppm) | Step Yield (%) |
|---|---|---|---|---|---|---|---|---|---|---|---|
|  |  | HMW (%) | MON (%) | LMW (%) | Acidic (%) | Main (%) | Basic (%) |  |  |  |  |
| Protein A | 8.2 | 0.1 | 98.5 | 1.4 | 15.8 | 57.2 | 27.2 | $2.25 \times 10^3$ | 9620 | $2.88 \times 10^3$ | 97 |
| Mixed Mode | 3.3 | 0.13 | 99.6 | 0.24 | 12.8 | 58.5 | 28.7 | <LOQ | 890 | 42.1 | 76 |
| Cation Exchange | 7.6 | 0.6 | 99.3 | 0.1 | 14.2 | 64.7 | 21.1 | <LOQ | 130 | <LOQ | 78 |

Example 9

Effects of Varying Mass Load on Intermediate Purification

The impact of varying mass load on the recovery and impurity clearance was evaluated. A study was performed under a range of binding capacities in which the flow through was collected and assessed based on product recovery, and acidic charge variant and high molecular weight species clearance. Table 35 shows the data from a mass loading study where the adalimumab Protein A eluate loaded onto the column varied from 50 g/L to 125 g/L. The relationship between mass loading and impurity clearances are shown in FIGS. 18-21.

The content of impurities that the feed-stream may have going on to the mixed mode resin and the clearance of any one or more the impurities that is required should dictate what mass loading is chosen. Hence, this provides a flexible chromatographic method for maintaining the desired impurity profile when the feed-stream may be variable.

TABLE 35

CAPTO® Adhere™ HEPES buffer impact on mass load vs. impurities clearances.

|  | Starting Material | pH and Conductivity Adjusted Load | | | | Flow-through | | | |
|---|---|---|---|---|---|---|---|---|---|
|  |  | 50 g/L | 75 g/L | 100 g/L | 125 g/L | 50 g/L | 75 g/L | 100 g/L | 125 g/L |
| % ACV | 23.3 | 24.6 | 24.5 | 24.6 | 24.4 | 19 | 20.5 | 21.6 | 21.8 |
| % ΔACV | NA | 1.3 | 1.2 | 1.3 | 1.1 | -4.3 | -2.8 | -1.7 | -1.5 |
| % HMW | 2.2 | 2.2 | 2.2 | 2.2 | 2.2 | 0.2 | 0.3 | 0.3 | 0.5 |
| % ΔHMW | NA | 0 | 0 | 0 | 0 | -2 | -1.9 | -1.9 | -1.7 |
| HCP (ppm) | 65.1 | 55.5 | 52.9 | 46.8 | 57.1 | 20.8 | 18.8 | 18.7 | 26.8 |
| rProA (ppb) | 256 | 217 | 193 | 227 | 208 | <44.2 | <35.5 | <31.1 | <26.8 |
| rDNA | <LOQ | <LOQ | <LOQ | <LOQ | <LOQ | <LOQ | <LOQ | <LOQ | <LOQ |
| % yield | NA | NA | NA | NA | NA | 81.48 | 86.12 | 88.89 | 97.6 |

Example 10

Effects of Varying Mass Load on Polishing Purification

The impact of mass loading on the resin also plays a role in the level of reduction that can be seen. A DoE was executed to map the design space when mass loading and conductivity are varied (pH is constant at 6.2). Table 36 shows the design and data from the study. Mass loading was tested from 30 to 60 g/L and showed a range of acidic charge variant reduction from 1 to 11% when the conductivity is varied by only from 5-7 mS/cm.

TABLE 36

CAPTO® SP ImpRes mass loading DoE

| Run # | Loading (g/L) | Cond (mS/cm) | Yield (%) | ΔHMW | ΔACV |
|---|---|---|---|---|---|
| 1 | 30 | 5 | 97.4 | 0.10 | -0.3 |
| 2 | 30 | 6 | 42.4 | 0.20 | -8.5 |
| 3 | 30 | 7 | 15.6 | 0.60 | -10.7 |
| 4 | 45 | 5 | 55.2 | 0.10 | -6.9 |
| 5 | 45 | 6 | 35.5 | 0.20 | -8.4 |
| 6 | 45 | 6 | 38.3 | 0.20 | -6.9 |
| 7 | 45 | 7 | 16.7 | 0.60 | -8.5 |
| 8 | 60 | 5 | 43.8 | 0.20 | -7.3 |
| 9 | 60 | 6 | 20.0 | 0.70 | -9.5 |
| 10 | 60 | 7 | 11.6 | 0.60 | -9.9 |

Figure 22:
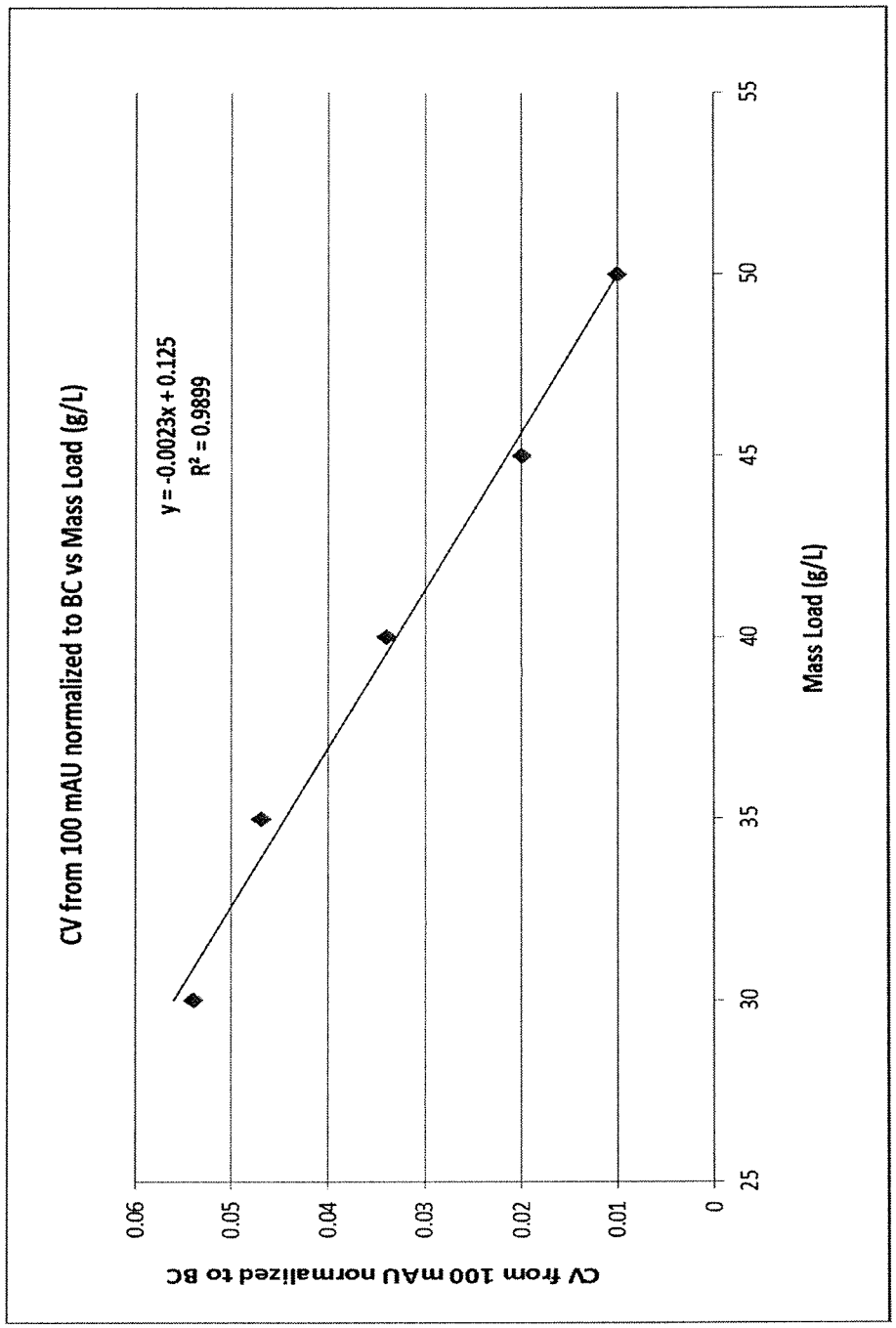
FIG. 22 shows the derivation of Wash-2 cutting criteria.

The development was focused on understanding the Wash-2 cutting/transition criteria. A correlation between mass loading and Wash-2 peak cutting was derived based on previous experiments varying mass loading on the CAPTO® SP ImpRes (FIG. 22). The line slope equation was used to predict the Wash-2 duration when initiated at 100 mAU on the ascending portion of the peak during the wash. The prediction was then tested using varied loading capacities and yield, HMW and acidic charge variant changes were monitored.

The data for mass loadings 30, 40 and 50 g/L are shown in Table 37, Table 38, and Table 39, respectively. The experiments described above were conducted at a scale suitable for screening (0.5 cm×10 cm column) and were subsequently repeated at a scale representative of manufacturing (1.6 cm×20 cm). The data showed a reduced amount of acidic charge variant clearance upon scale up. The reduced amount of clearance was subsequently tested at the pilot scale (10 cm×20 cm) with the same results. In order to provide a Wash-2 operation that would be flexible to a variable amount of acidic charge variants that may be present in the feed stock while maintaining an acceptable product recovery, a summary table (Table 40) was created from a series of chromatography runs (loaded to 30 g/L) at a column scale of 1.6 cm×20 cm. The data can be used by manufacturing to guide the operation of the polishing step as there may be variable levels of charge heterogeneity emanating from the bioreactor, which in turn requires different amounts of clearance from the CAPTO® SP ImpRes chromatography.

TABLE 37

Impact of peak cutting on HMW and acidic charge variant clearance at 30 g/L loading.

| Peak Cut Point | 30 g/L | | |
|---|---|---|---|
| (CV from 100 mAU) | % Yield | % HMW | Δ % ACV |
| 0.32 | 83.5 | 0.7 | 3.1 |
| 0.65 | 77.4 | 0.7 | 4.6 |
| 0.97 | 75.4 | 0.8 | 4.8 |
| 1.30 | 70.2 | 0.8 | 5.5 |
| 1.62 | 67.1 | 0.7 | 5.8 |

TABLE 38

Impact of peak cutting on HMW and acidic charge variant clearance at 40 g/L loading.

| Peak Cut Point | 40 g/L | | |
|---|---|---|---|
| (CV from 100 mAU) | % Yield | % HMW | Δ % ACV |
| 0.27 | 70.1 | 0.5 | 5.0 |
| 0.54 | 68.4 | 0.8 | 5.1 |
| 0.81 | 59.6 | 0.8 | 5.9 |
| 1.08 | 60.6 | 0.8 | 5.9 |
| 1.35 | 56.7 | 0.7 | 6.6 |

TABLE 39

Impact of peak cutting on HMW and acidic charge variant clearance at 50 g/L loading.

| Peak Cut Point | 50 g/L | | |
|---|---|---|---|
| (CV from 100 mAU) | % Yield | % HMW | Δ % ACV |
| 0.1 | 63.1 | 0.8 | 5.5 |
| 0.2 | 62.9 | 0.9 | 5.2 |
| 0.3 | 61.2 | 0.8 | 5.5 |
| 0.4 | 56.9 | 0.9 | 6.2 |
| 0.5 | 59.9 | 0.9 | 5.8 |

TABLE 40

CAPTO® SP ImpRes Wash-2 peak cutting summary (30 g/L Loading).

| Wash-2 Duration (CV) | % ACV Removed | % HMW Removed | % ONS-3010 Recovery |
|---|---|---|---|
| 0.16 | 2.50 | 0.19 | 93.6 |
| 0.32 | 2.70 | 0.16 | 91.7 |
| 0.65 | 4.00 | 0.11 | 88.1 |
| 0.97 | 4.10 | 0.12 | 83.3 |
| 1.30 | 5.40 | 0.14 | 79.6 |
| 1.62 | 5.90 | 0.16 | 76.7 |
| 90% of Wash-2 Peak Max | 5.9-7.5 | NA | ≥60.0 |

The invention is not limited to the embodiments described and exemplified above, but is capable of variation and modification within the scope of the appended claims.

---

We claim:

1. A process for removing acid charge variants from a monoclonal antibody, comprising
   (a) loading a mammalian cell-expressed monoclonal antibody preparation onto a Protein A support, and eluting the monoclonal antibody from the Protein A support, thereby producing a first eluate comprising the monoclonal antibody;
   (b) loading the first eluate from step (a) onto an anion exchange and hydrophobic interaction (AEX/HIC) chromatography support, and allowing the first eluate to flow through the support, thereby producing a flow-through pool comprising the monoclonal antibody;
   (c) loading the flow-through pool comprising the monoclonal antibody onto a cation exchange (CEX) chromatography support having an antibody binding capacity of from about 25 g/L to about 65 g/L and performing wash steps comprising;
      (i) performing a first wash step comprising a wash buffer having a pH from about 5.8 to about 6.6 and a conductivity target from about 1.0 mS/cm to about 3.6 mS/cm;

(ii) performing a second wash step comprising a wash buffer having a pH from about 5.8 to about 6.6, a conductivity target from about 6.6 mS/cm to about 7.6 mS/cm, and a sodium chloride concentration from about 30 mM to about 60 mM:

wherein the second wash step comprises determining when the absorbance units measured at UV A280 decrease from about 7% to about 14% from the peak absorbance units measured at UV A280; and (iii) performing a third wash step comprising a wash buffer having a pH from about 5.8 to about 6.6 and a conductivity target from about 1.0 mS/cm to about 3.6 mS/cm; and (d) eluting the monoclonal antibody from the CEX chromatography support in step with an elution buffer having a pH of from about 6.0 to about 6.4 and a conductivity target of from about 10 mS/cm to about 14 mS/cm, thereby producing a second eluate comprising the monoclonal antibody and from about 10% to about 20% by weight of acid charge variants of the monoclonal antibody.

2. The method of claim 1, wherein the monoclonal antibody specifically binds to tumor necrosis factor (TNF) alpha.

3. The method of claim 1, wherein the monoclonal antibody comprises a heavy chain comprising the amino acid sequence of SEQ ID NO: 1 and a light chain comprising the amino acid sequence of SEQ ID NO: 2.

4. The method of claim 1, wherein the the wash buffer of steps (c)(i), (c)(ii) and (c)(iii) comprises a pH of from about 5.9 to about 6.5.

5. The method of claim 1, wherein the the wash buffer of steps (c)(i), (c)(ii) and (c)(iii) comprises a pH of from about 6 to about 6.4.

6. The method of claim 1, wherein the the wash buffer of steps (c)(i), (c)(ii) and (c)(iii) comprises a pH of from about 6.1 to about 6.3.

7. The method of claim 1, wherein the the wash buffer of steps (c)(i), (c)(ii) and (c)(iii) comprises a pH of about 6.2.

8. The method of claim 1, wherein the wash buffer of wash step (c)(ii) comprises a conductivity target of from about 6.8 mS/cm to about 7.4 mS/cm.

9. The method of claim 1, wherein the wash buffer of wash step (c)(ii) comprises a conductivity target of from about 6.9 mS/cm to about 7.3 mS/cm.

10. The method of claim 1, wherein the wash buffer of wash step (c)(ii) comprises a conductivity target of from about 7 mS/cm to about 7.2 mS/cm.

11. The method of claim 1, wherein the wash buffer of wash step (c)(ii) comprises a conductivity target of about 7.2 mS/cm.

12. The method of claim 1, wherein the elution buffer comprises a pH of from about 6.1 to about 6.3.

13. The method of claim 1, wherein the elution buffer comprises a pH of about 6.2.

14. The method of claim 1, wherein the elution step comprises a conductivity target of from about 11 mS/cm to about 14 mS/cm.

15. The method of claim 1, wherein the elution step comprises a conductivity target of from about 12 mS/cm to about 14 mS/cm.

16. The method of claim 1, wherein the elution step comprises a conductivity target of from about 12 mS/cm to about 13 mS/cm.

17. The method of claim 1, wherein the elution step comprises a conductivity target of from about 12.3 mS/cm to about 13.3 mS/cm.

18. The method of claim 1, wherein the elution step comprises a conductivity target of from about 12.6 mS/cm to about 13 mS/cm.

19. The method of claim 1, wherein the elution step comprises a conductivity target of about 12.8 mS/cm.

20. The method of claim 1, wherein the second eluate comprises the monoclonal antibody and from about 9% to about 15% by weight of acid charge variants of the monoclonal antibody.

21. The method of claim 1, wherein the second eluate comprising the monoclonal antibody and from about 10% to about 14% by weight of acid charge variants of the monoclonal antibody.

22. The method of claim 1, wherein the antibody preparation loaded onto the Protein A support comprises from about 20% to about 30% by weight of acid charge variants of the monoclonal antibody.

23. The of claim 1, wherein the antibody preparation loaded onto the Protein A support comprises from about 22% to about 28% by weight of acid charge variants of the monoclonal antibody.

24. The method of claim 1, wherein the antibody preparation loaded onto the Protein A support comprises from about 24% to about 26% by weight of acid charge variants of the monoclonal antibody.

25. The method of claim 1, wherein the antibody preparation loaded onto the Protein A support comprises about 25% by weight of acid charge variants of the monoclonal antibody.

26. The method of claim 1, further comprising filtering the second eluate with a filter having a pore size of from about 15 nm to about 20 nm.

27. The method of claim 1, further comprising concentrating and diafiltrating the second eluate.

28. The method of claim 1, wherein the elution buffer comprises sodium chloride and step (d) comprises increasing the sodium chloride concentration of the elution buffer according to a linear gradient.

29. The method of claim 1, wherein the elution buffer comprises sodium chloride and step (d) comprises increasing the sodium chloride concentration of the elution buffer according to a step-wise gradient.

30. The method of claim 28, wherein the sodium chloride concentration is increased to about 100 mM.

* * * * *

UNITED STATES PATENT AND TRADEMARK OFFICE
CERTIFICATE OF CORRECTION

PATENT NO. : 10,696,735 B2
APPLICATION NO. : 15/545271
DATED : June 30, 2020
INVENTOR(S) : Chris Yonan et al.

It is certified that error appears in the above-identified patent and that said Letters Patent is hereby corrected as shown below:

In the Claims

At Column 51, Line number 30, Claim number 4:
"4. The method of claim 1, wherein the the wash buffer of"

Should read:
-- 4. The method of claim 1, wherein the wash buffer of --

At Column 51, Line number 33, Claim number 5:
"5. The method of claim 1, wherein the the wash buffer of"

Should read:
-- 5. The method of claim 1, wherein the wash buffer of --

At Column 51, Line number 36, Claim number 6:
"6. The method of claim 1, wherein the the wash buffer of"

Should read:
-- 6. The method of claim 1, wherein the wash buffer of --

At Column 51, Line number 39, Claim number 7:
"7. The method of claim 1, wherein the the wash buffer of"

Should read:
-- 7. The method of claim 1, wherein the wash buffer of --

Signed and Sealed this
Fourth Day of June, 2024

Katherine Kelly Vidal
*Director of the United States Patent and Trademark Office*

SEQUENCE LISTING

<160> NUMBER OF SEQ ID NOS: 9

<210> SEQ ID NO 1
<211> LENGTH: 451
<212> TYPE: PRT
<213> ORGANISM: Homo sapiens

<400> SEQUENCE: 1

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser

```
            115                 120                 125
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 2
<211> LENGTH: 214
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30
```

```
Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 121
<212> TYPE: PRT
<213> ORGANISM: Homo sapiens

<400> SEQUENCE: 3

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 4
<211> LENGTH: 98
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
 1               5                  10                  15
```

-continued

```
Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                      55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val

<210> SEQ ID NO 5
<211> LENGTH: 12
<212> TYPE: PRT
<213> ORGANISM: Homo sapiens

<400> SEQUENCE: 5

Glu Pro Lys Ser Cys Asp Lys Thr His Thr Cys Pro
1               5                   10

<210> SEQ ID NO 6
<211> LENGTH: 93
<212> TYPE: PRT
<213> ORGANISM: Homo sapiens

<400> SEQUENCE: 6

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
             20                  25                  30

Thr Cys Val Val Val Asp Val Ser His Glu Asp Pro Glu Val Lys Phe
         35                  40                  45

Asn Trp Tyr Val Asp Gly Val Glu Val His Asn Ala Lys Thr Lys Pro
 50                      55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys
                 85                  90

<210> SEQ ID NO 7
<211> LENGTH: 127
<212> TYPE: PRT
<213> ORGANISM: Homo sapiens

<400> SEQUENCE: 7

Cys Lys Val Ser Asn Lys Ala Leu Pro Ala Pro Ile Glu Lys Thr Ile
1               5                   10                  15

Ser Lys Ala Lys Gly Gln Pro Arg Glu Pro Gln Val Tyr Thr Leu Pro
             20                  25                  30

Pro Ser Arg Asp Glu Leu Thr Lys Asn Gln Val Ser Leu Thr Cys Leu
         35                  40                  45

Val Lys Gly Phe Tyr Pro Ser Asp Ile Ala Val Glu Trp Glu Ser Asn
 50                      55                  60

Gly Gln Pro Glu Asn Asn Tyr Lys Thr Thr Pro Pro Val Leu Asp Ser
65                  70                  75                  80

Asp Gly Ser Phe Phe Leu Tyr Ser Lys Leu Thr Val Asp Lys Ser Arg
                 85                  90                  95
```

```
Trp Gln Gln Gly Asn Val Phe Ser Cys Ser Val Met His Glu Ala Leu
                100                 105                 110

His Asn His Tyr Thr Gln Lys Ser Leu Ser Leu Ser Pro Gly Lys
            115                 120                 125

<210> SEQ ID NO 8
<211> LENGTH: 108
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg
            100                 105

<210> SEQ ID NO 9
<211> LENGTH: 106
<212> TYPE: PRT
<213> ORGANISM: Homo sapiens

<400> SEQUENCE: 9

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```